(12) United States Patent
Bathe et al.

(10) Patent No.: US 11,514,331 B2
(45) Date of Patent: Nov. 29, 2022

(54) SEQUENCE-CONTROLLED POLYMER RANDOM ACCESS MEMORY STORAGE

(71) Applicant: Massachusetts Institute of Technology, Cambridge, MA (US)

(72) Inventors: Mark Bathe, Cambridge, MA (US); Sakul Ratanalert, Cambridge, MA (US); Remi Veneziano, Allston, MA (US); James Banal, Cambridge, MA (US); Tyson Shepherd, Arlington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1067 days.

(21) Appl. No.: 16/097,594

(22) PCT Filed: Apr. 27, 2017

(86) PCT No.: PCT/US2017/029948
§ 371 (c)(1),
(2) Date: Oct. 29, 2018

(87) PCT Pub. No.: WO2017/189914
PCT Pub. Date: Nov. 2, 2017

(65) Prior Publication Data
US 2020/0327421 A1    Oct. 15, 2020

Related U.S. Application Data

(60) Provisional application No. 62/356,885, filed on Jun. 30, 2016, provisional application No. 62/328,455, filed on Apr. 27, 2016.

(51) Int. Cl.
*G06N 3/12* (2006.01)
*G06F 12/06* (2006.01)
(Continued)

(52) U.S. Cl.
CPC .............. *G06N 3/123* (2013.01); *B82Y 10/00* (2013.01); *G06F 12/0646* (2013.01);
(Continued)

(58) Field of Classification Search
CPC ........ G06N 3/123; G06N 3/002; B82Y 10/00; G06F 12/0646; G06F 2212/251
See application file for complete search history.

(56) References Cited

U.S. PATENT DOCUMENTS 4,816,567 A    3/1989  Cabilly
5,356,802 A   10/1994  Chandrasegaran
(Continued)

FOREIGN PATENT DOCUMENTS

CN     106119269    11/2016
WO       9853059    11/1998
(Continued)

OTHER PUBLICATIONS

Abramoff, et al., "Image processing with ImageJ", Biophotonics Int., 11(2):36-42 (2004).
(Continued)

*Primary Examiner* — Ajay Ojha
(74) *Attorney, Agent, or Firm* — Pabst Patent Group LLP

(57) ABSTRACT

Methods for controlled segregation of blocks of information encoded in the sequence of a biopolymer, such as nucleic acids and polypeptides, with rapid retrieval based on multiply addressing nanostructured data have been developed. In some embodiments, sequence controlled polymer memory objects include data-encoded biopolymers of any length or form encapsulated by natural or synthetic polymers and including one or more address tags. The sequence address labels are used to associate or select memory objects for sequencing read-out, enabling organization and access of distinct memory objects or subsets of memory objects using
(Continued)

Boolean logic. In some embodiments, a memory object is a single-stranded nucleic acid scaffold strand encoding bit stream information that is folded into a nucleic acid nanostructure of arbitrary geometry, including one or more sequence address labels. Methods for controlled degradation of biopolymer-encoded blocks of information in the memory objects are also developed.

48 Claims, 21 Drawing Sheets

(51) Int. Cl.
   *G11C 13/02* (2006.01)
   *B82Y 10/00* (2011.01)
(52) U.S. Cl.
   CPC ........ *G11C 13/02* (2013.01); *C12Q 2563/149* (2013.01); *C12Q 2563/185* (2013.01); *G06F 2212/251* (2013.01)

(56) References Cited

U.S. PATENT DOCUMENTS

| | | | |
|---|---|---|---|
| 5,436,150 | A | 7/1995 | Chandrasegaran |
| 5,487,994 | A | 1/1996 | Chandrasegaran |
| 5,624,821 | A | 4/1997 | Winter |
| 6,140,081 | A | 10/2000 | Barbas |
| 6,194,551 | B1 | 2/2001 | Idusogie |
| 6,453,242 | B1 | 9/2002 | Eisenberg |
| 6,534,261 | B1 | 3/2003 | Cox |
| 6,610,512 | B1 | 8/2003 | Barbas |
| 6,746,838 | B1 | 6/2004 | Choo |
| 6,866,997 | B1 | 3/2005 | Choo |
| 7,067,617 | B2 | 6/2006 | Barbas |
| 8,227,242 | B2 | 7/2012 | Bradbury |
| 8,501,923 | B2 | 8/2013 | Rothemund |
| 9,545,452 | B2 * | 1/2017 | Wang ................ A61K 47/6911 |
| 2002/0165356 | A1 | 11/2002 | Barbas |
| 2003/0215914 | A1 | 11/2003 | Houtzager |
| 2004/0180422 | A1 | 9/2004 | Hoet |
| 2004/0197892 | A1 | 10/2004 | Moore |
| 2005/0147962 | A1 | 7/2005 | Wagstrom |
| 2007/0117109 | A1 | 5/2007 | Rothemund |
| 2007/0128728 | A1 | 6/2007 | Bradbury |
| 2007/0154989 | A1 | 7/2007 | Barbas |
| 2007/0213269 | A1 | 9/2007 | Barbas |
| 2012/0251583 | A1 | 10/2012 | Rothemund |
| 2013/0295614 | A1 | 11/2013 | Hareendran |
| 2019/0142882 | A1 | 5/2019 | Shepherd |
| 2019/0203242 | A1 | 7/2019 | Praetorius |
| 2020/0181602 | A1 | 6/2020 | Zobeck |

FOREIGN PATENT DOCUMENTS

| | | |
|---|---|---|
| WO | 9958572 | 11/1999 |
| WO | 2000071694 | 11/2000 |
| WO | 2003016496 | 2/2003 |
| WO | 2004048543 | 6/2004 |
| WO | 2007067818 | 6/2007 |
| WO | 2013176772 | 11/2013 |
| WO | 2014018423 | 6/2014 |
| WO | 2017089567 | 6/2017 |
| WO | 2017089570 | 6/2017 |
| WO | 2017189870 | 11/2017 |
| WO | 2017189914 | 11/2017 |
| WO | 2019094928 | 5/2019 |

OTHER PUBLICATIONS

Ailenberg, et al., "An improved Huffman coding method for archiving text, images, and music characters in DNA", BioTechniques., 47:747-754 (2009).

Amunts, et al., "Ribosome. The structure of the human mitochondrial ribosome", Science., 348(6230):95-98 (2015).
Angal, et al., "A single amino acid substitution abolishes the heterogeneity of chimeric mouse/human (IgG4) antibody", Mol. Immunol., 30:105-08 (1993).
Anonymous, et al., "M13mp18 (Cloning Vector)", New England BioLabs Catalog, http://international.neb.com/-/media/nebus/page-images/tools/dna-sequences-and-maps/m13mp18_map.pdf?la=en&hash+ABF432A1085CFA7CA7850D00B69ACBE654DFC580( 2002).
Arita, et al., "Chapter 368: DNA Memory", Handbook of Natural Compu, 1281-1318 (2012).
Arizona State University, "Top-down design brings new DNA structures to life", retrieved from the internet: URL:https://phys.org/news/2016-05-top-down-dna-life.html :1-4 (2016).
Babaei, "A novel text and image encryption method based on chaos theory and DNA computing", Nat Comput., 12:101-107 (2013).
Bai, et al., "Cryo-EM structure of a 3D DNA-origami object", Proc. Natl. Acad. Sci. 109, 20012-20017 (2012).
Benson, et al., "Computer-Aided Production of Scaffolded DNA Nanostructures from Flat Sheet Meshes", Angewandte Chemie, 55(31):8869-8872 (2016).
Benson, et al., "DNA rendering of polyhedral meshes at the nanoscale", Nature, 523:441-444 (2015).
Benson, et al., "Supplementary Information to DNA rendering of polyhedral meshes at the nanoscale", Nature, 523(7561):441-444 (2015).
Bent, et al., "On non-intersecting Eulerian circuits", Discrete Appl. Math. 18(1):87-94 (1987).
Bhatia, et al., "Icosahedral DNA nanocapsules by modular assembly", Angew. Chem. Int. Ed., 48(23):4134-4137 (2009).
Bornholt, et al., "A DNA-based Archival Storage System", 21th ACM International Conference on Architectural Support for Programming Languages and Operating Systems, 1-13, (2016).
Braasch, et al., "Locked nucleic acid (LNA): Fine-tuning the recognition of DNA and RNA", Chem. Biol., 8(1):1-7 (2001).
Brown, et al., "An easy-to-prepare mini-scaffold for DNA origami", Nanoscale, 7:16621-4 (2015).
Brudno, et al., "Recent progress toward the templated synthesis and directed evolution of sequence-defined synthetic polymers", Chem Biol., 16(3):265-276 (2009).
Castro, et al., "A primer to scaffolded DNA origami", Nat. Methods., 8(3):221-229 (2011).
Chandran, et al., "DNA origami: Folding DNA into Desired Shapes", Fourth Warft Workshop on Brain Modeling and Supercomputing, (2009).
Chasteen, et al., Eliminating helper phage from phage display Nucleic Acids Res., 34(21):e145 (2006).
Cho, "An unnatural biopolymer", Science, 261(5126): 1303-1305 (1993).
Church, et al. "Next-generation digital information storage in DNA", Science, 337(6102):1628 (2012).
Clelland, et al., "Hiding messages in DNA microdots", Nature, 399(673):533-534 (1999).
Cong, "Multiplex genome engineering using CRISPR/Cas systems-",Science, 15:339(6121):819-823 (2013).
Cui, et al., "An encryption scheme using DNA technology", 2008 Third International Conference on Bio-Inspired Computing: Theories and Applications., 37-41(2008).
Dietz, et al., "Folding DNA into twisted and curved nanoscale shapes", Science, 325(5941):725-730 (2009).
Dotto, et al., "Initiation and termination of phage f1 plus-strand synthesis", Proc. Natl. Acad. Sci. U.S.A., 79:7122-7126 (1982).
Douglas, et al., "Self-assembly of DNA into nanoscale three-dimensional shapes", Nature, 459(7425):414-418 (2009).
Douglas, et al., "A logic-gated nanorobot for targeted transport of molecular payloads", Science, 335(6070):831-834 (2012).
Douglas, et al., "Rapid prototyping of 3D DNA-origami shapes with caDNAno", Nucleic Acids Res., 37:5001-5006 (2009B).
Dunn, et al., "Guiding the folding pathway of DNA origami", Nature, 525(7567):82-86 (2015).

(56) References Cited

OTHER PUBLICATIONS

Dutta, et al., "DNA-directed artificial light-harvesting antenna", Journal of the American Chemical Society, 133(31):11985-11993 (2011).
Elbashir, et al., "Duplexes of 21-nucleotide RNAs mediate RNA interference in cultured mammalian cells", Nature, 411:494-498 (2001).
Elbaz, et al., "Genetic encoding of DNA nanostructures and their self-assembly in living bacteria", Nat Commun, 7:11179 (2016).
Ellis-Monaghan, et al., "DNA origami and the complexity of Eulerian circuits with turning costs", Nat. Comput., 14(3):491-503 (2015).
Ennifar, et al., "Targeting the dimerization initiation site of HIV-1 RNA with aminoglyocosides: from crystal to cell", Nucleic Acids Research. 34, 2328-2339 (2006).
Faber, et al., "Structural Rearrangements of HIV-1 Tat-responsive RNA upon Binding of Neomycin B*", The Journal of Biological Chemistry. 275:20660-20666 (2000).
Fan, et al., "Gating machinery of InsP3R channels revealed by electron cryomicroscopy", Nature, 527:336-341 (2015).
Fang, et al., "An unusual Toplogical Structure of the HIV-1 Rev Response Element" Cell, 155:594-605 (2013).
Fang, et al., "Small-angle X-ray scattering: a bridge between RNA secondary structures and three-dimensional topological structures" Current Opinion in Structural Biology. 30, 147-160 (2015).
Fire, et al. "Potent and specific genetic interference by double-stranded RNA in Caenorhabditis elegans", Nature, 391(6669):806-11 (1998).
Fu, et al., "Controlled drug release by a nanorobot", Nature Biotechnology, 30(5):407-408 (2012).
Fu, et al., "DNA double-crossover molecules", Biochemistry, 32(13):3211-3220 (1993).
Geary, et al., "RNA nanostructures. A single-stranded architecture for cotranscriptional folding of RNA nanostructures", Science, 345:799-804 (2014).
Gehani, et al., "DNA-based Cryptography", Leet Notes Comput Sc., 2950:167-188 (2004).
Gellman, "Foldamers: A Manifesto", Acc. Chem. Res., 31(4):173-180 (1998).
Goldman et al., "Towards practical, high-capacity, low-maintenance information storage in synthesized DNA", Nature, 494(7435):77-80 (2013).
Gradišar, et al., "Design of a single-chain polypeptide tetrahedron assembled from coiled-coil segments", Nat. Chem. Biol., 9(6):362-366 (2013).
Grass, et al., "Robust chemical preservation of digital information on DNA in silica with error-correcting codes", Angew. Chem. Int. Ed., 54(8):2552-2555 (2015).
Gruber, et al., "Efficient tumor cell lysis mediated by a bispecific single chain antibody expressed in *Escherichia coli.*", J. Immunol., 152(11):5368 (1994).
Gu, et al., "Dynamic patterning programmed by DNA tiles captured on a DNA origami substrate", Nature Nanotechnology, 4(4):245-248 (2009).
Han, et al., "DNA gridiron nanostructures based on four-arm junctions", Science. 339(6126):1412-1415 (2013).
Han, et al., "DNA origami with complex curvatures in three-dimensional space", Science, 332(6027):342-346 (2011).
Han, et al., "Single-stranded DNA and RNA origami", Science, 358(6369) (2017).
Hannon, "RNA interference", Nature, 418(6894):244-251 (2002).
He, et al., "Hierarchical self-assembly of DNA into symmetric supramolecular polyhedra", Nature, 452(7184): 198-201 (2008).
He, et al., "On the Chirality of Self-Assembled DNA Octahedra", Angew. Chem., 122(4):760-763 (2010).
Henderson, et al., "Outcome of the first electron microscopy validation task force meeting", Structure, 20(2):205-214 (2012).
Hollinger, et al., "Diabodies: small bivalent and bispecific antibody fragments", Proc. Natl. Acad. Sci. U.S.A., 90(14):6444-6448 (1993).
Howe, et al., "Seletive small-molecule inhibition of an RNA structural element", Nature, 526:672-677 (2015).
Iinuma et al., "Supplementary Material for Polyhedra self-assembled from tripods and Chracterized with 3D DNA-Paint", Science, 344(6179):65-69 (2014).
Iinuma, et al., "Polyhedra Self-Assembled from DNA-Paint", Science, 344(6179): 65-69 (2014).
International Search Report for corresponding PCT application PCT/US2017/029948 dated Aug. 2, 2017.
Irobalieva, et al., "Structural diversity of supercoiled DNA", Nat. Commun., 6:8440 (2015).
Jiang, et al., "DNA origami as a carrier for circumvention of drug resistance", Journal of the American Chemical Society 134(32): 13396-13403 (2012).
Jinek, et al., "A programmable dual-RNA-guided DNA endonuclease in adaptive bacterial immunity", Science, 337(6096):816-21 (2012).
Jones, et al., "Nanomaterials. Programmable materials and the nature of the DNA bond", Science, 347(6224): 1260901 (2015).
Jones, et al., "Small-angle X-ray scattering-derived structure of the HIV-1 5' UTR reveals 3D tRNA mimicry", Proceedings of the National Academy of Sciences of the United States of America. 111:3395-3400 (2014).
Kallenbach, et al., "An immobile nucleic acid junction constructed from oligonucleotides", Nature, 305:829-831 (1983).
Kazantsev, et al., Proceedings of the National Academy of Sciences of the United States of America. 100: 7497-7502 (2003).
Ke, et al. "Multilayer DNA Origami Packed on a Square Lattice", J. A. Chem. Soc., 131:15903-15908 (2009).
Ke, et al., "DNA brick crystals with prescribed depths", Nat. Chem., 6:994-1002 (2014).
Ke, et al., "Self-Asssembled Water-Soluble Nucleic Acid Probe Tiles for Label-Free RNA Hyrbidization Assays", Science, 319:180-183 (2008).
Ke, et al., "Three-dimensional structures self-assembled from DNA bricks", Science, 338(611): 1177-1183 (2012).
Ke, et al., "Two design strategies for enhancement of multilayer-DNA-origami folding: underwinding for specific intercalator rescue and staple-break positioning",Chem. Sci., 3(8):2587-2957 (2012B).
Keane, et al., "Structure of the HIV-1 RNA packaging signal", Science, 348(6237):917-921 (2015).
Kertesz, et al., "Genome-wide measurement of RNA secondary structure in yeast", Nature, 467:103-107 (2010).
Kick, et al., "Efficient Production of Single-Stranded Phage DNA as Scaffolds for DNA Origami", Nano Lett, 15:4672-6 (2015).
Kim et al., "Extending Lifetime of Flash Memory Using Strong Error Correction Coding", IEEE Trans. Consum. Electron., 61:206-214 (2015).
Kim, et al. "Insertion and deletion mutants of FokI restriction endonuclease", J. Biol. Chem., 269:31978-31982 (1994B).
Kim, et al., "Chimeric restriction endonuclease", Proc. Natl. Acad. Sci. USA., 91:883-887 (1994A).
Ko, et al., "Synergistic self-assembly of RNA and DNA molecules", Nature Chemistry, 2(12):1050-1055 (2010).
Kostelny, et al., "Formation of a bispecific antibody by the use of leucine zippers", J. Immunol., 148(5):1547-1553 (1992).
Krishnan, et al., "Designer nucleic acids to probe and program the cell", Trends in Cell Biology, 22(12):624-633 (2012).
Kurreck, et al., "Design of antisense oligonucleotides stabilized by locked nucleic acids", Nucleic Acids Res., 30(9):1911-1918 (2002).
Kuzyk, et al., "DNA-Based Self-Assembly of Chiral Plasmonic Nanostructures With Tailored Optical Response", Nature, 483(7389):311-314 (2012).
Leier, et al., "Cryptography with DNA binary strands", Biosystems, 57(1):13-22 (2000).
Li, et al., "Alteration of the cleavage distance of Fok I restriction endonuclease by insertion mutagenesis", Proc. Natl. Acad. Sci. USA, 90(7):2764-2768 (1993).
Li, et al., "Functional domains in Fok I restriction endonuclease", Proc., Natl. Acad. Sci. USA, 89(10):4275-4279 (1992).
Li, et al., "Nucleic-based nanoengineering: novel structures for biomedical applications", Interface Focus, 1(5): 702-724 (2011).

(56) References Cited

OTHER PUBLICATIONS

Li, et al., "Quantifying Absolute Protein Synthesis Rates Reveals Principles Underlying Allocation of Cellular Resources", Cell, 157(3):624-635 (2014).
Liedl, et al., "Self-assembly of 3D prestressed tensegrity structures from DNA", Nature Nanotechnology, 5:520-524 (2010).
Linko, et al., "Automated design of DNA origami", Nature Biotechnology, 34(8):826-827 (2016).
Liu et al., "Crystalline two-dimensional DNA-origami arrays", Angew. Chem. Int. Ed. Engl., 50(1):264-267 (2011).
Liu, et al., "Diamond family of nanoparticle superlattices", Science, 351(6273):582-586 (2016).
Liu, et al., "Quantifying Absolute Protein Synthesis Rates Reveals Principles Underlying Allocation of Cellular Responses", Nano Letters, 12:4254-4259 (2012).
Lutz, et al., "Sequence-controlled Polymers", Science, 341:1238149 (2013).
Marchi, et al., "Toward larger DNA origami", Nano Lett, 14:5740-7 (2014).
Martin, et al., "Magnesium-free self-assembly of multi-layer DNA objects", Nat. Commun., 3:1103 (2012).
Masanori, et al., "Chapter 368: DNA Memory", Handbook of Natural Compu, 1281-1318 (2012).
Maxam et al., "A new method for sequencing DNA", Proc. Nat. Acad. Sci. USA, 74(2):560-564 (1977).
Mercer, et al., "Structure and function of long noncoding RNAs in epigenetic regulation", Nature Structural & Molecular Biology. 20, 300-307 (2013).
Michelotti, et al., "Beyond DNA origami: A look on the bright future of nucleic acid nanotechnology", Wiley Interdiscip Rev Nanomed Nanobiotechnol., 4(2):139-152 (2012).
Morrison, et al., "Chimeric human antibody molecules: mouse antigen-binding domains with human constant region domains", Proc. Natl. Acad. Sci. USA, 81:6851-6855 (1984).
Nafisi, et al., Synthetic Biology, 3(1), ysy015 (8 pages) (2018).
Napoli, et al., Introduction of a Chimeric Chalcone Synthase Gene into Petunia Results in Reversible Co-Suppression of Homologous Genes in trans., Plant Cell, 2(4):279-289 (1990).
Nelson et al., "Droplet Actuation by Electrowetting-on-Dielectric (EWOD): A Review", Journal of Adhesion Science and Technology, 26:747-1771 (2012).
Nickels, et al., "DNA origami structures directly assembled from intact bacteriophages", Small, 10:1765-9 (2014).
Nielsen, et al., "Sequence-selective recognition of DNA by strand displacement with a thymine-substituted polyamide", Science, 254(5037): 1497-1500 (1991).
Nogales, et al., "Cryo-EM: A Uniquw Tool for the vizualization of Macromolecular Complexity", Molecular Cell, 58:677-689 (2015).
Olson, et al., "New Structue Sheds Light on Selective HIV-1 Genomic RNA Packaging", Viruses, 7:4826-4835 (2015).
Pan, et al., "Lattice-free prediction of three-dimensional structure of programmed DNA assemblies", Nature Communications., 5:5578 (2014A).
Pan, et al., "Structure-based model for light-harvesting properties of nucleic acid nanostructures", Nucleic Acids Research, 42(4):2159-2170 (2014B).
Pandey, et al., "Algorithmic design of self-folding polyhedral", Proc. Natl. Acad. Sci. 108(50):19885-19890 (2011).
Pardee, et al., "Paper-based synthetic gene networks", Cell, 159(4):940-954 (2015).
Pasqualini, et al., "Organ targeting in vivo using phage dislay peptide libraries", Nature, 380:364-366 (1996).
Peng, et al., "Bottom-up nanofabrication using DNA nanostructures", Chem Matter, 28(4):1012-1021 (2016).
Praetorius, et al., "Biotechnological mass production of DNA origami", Nature, 552(7683):84-7 (2017).
Prim, "Shortest connection networls and some generalizations", Bell Syst. Tech. J., 36(6):1389-1401 (1957).
Rich, "The rise of single-molecule DNA biochemistry", Proc. Natl. Acad. Sci. U. S. A., 95(24):13999-14000 (1998).
Rothemund, "Scaffolded DNA Origami: from Generalized Multicrossovers to Polygonal Networks", Nanotechnology: Science and Computation, 3-21 (2006b).
Rothemund, et al., "Algorithmic self-assembly of DNA Sierpinski Triangles", PLoS Biol., 2:2041-2053 (2004).
Rothemund, et al., "Folding DNA to create nanoscale shapes and patterns", Nature, 440(7082):297-302 (2006).
Rouskin, et al., "Genome-wide probing of RNA structure reveals active unfolding of mRNA strucutres in vivo", Nature. 505:701-705 (2014).
Said, et al., "M1.3—a small scaffold for DNA origami", Nanoscale, 5(1):284-290 (2013).
Sanger, et al., "DNA sequencing with chain-terminating inhibitors", Proc. Natl. Acad. Sci. U.S.A., 74(12):5463-5467(1977).
Santangelo, et al., "Nanostructred Probes for RNA Detection in Living Cells", Annals of Biomedical Engineering, 34:39-50 (2006).
Seeman, et al., "Design of immobile nucleic acid junctions", Biophys. J., 44(2):201-209 (1983).
Seeman, et al., "DNA nicks and nodes and nanotechnology", Nano Lett., 1:22-26 (2001).
Sharma, et al., "Control of self-assembly of DNA tubules through integration of gold nanoparticles", Science, 323:112-6 (2009).
Shaw, et al., "Purification of functionalized DNA origami nanostructures", ACS Nano, 9(5):4968-4975 (2015).
Shih, et al., "A 1.7-kilobase single-stranded DNA that folds into a nanoscale octahedron", Nature, 427(6975):618-621 (2004).
Siegfried, et al.," RNA motif discovery by SHAPE and mutational profiling (SHAPE-MaP)", Nature Methods, 11(9):959-965 (2014).
Sinclair, et al., "Generation of protein lattices by fusing proteins with matching rotational symmetry", Nat. Nanotechnol. 6(9):558-562 (2011).
Smola, et al., "Selective 2'-hydroxyl acylation analyzed by primer extension and mutational profiling (SHAPE-MaP) for direct, versatile and accurate RNA structure analysis", Nat Protoc.10(11):1643-1669 (2015).
Sobczak, et al., "Rapid folding of DNA into nanoscale shapes at constant temperature", Science, 338(6113):1458-1461 (2012).
Songsivilai, et al., "Bispecific antibody: a tool for diagnosis and treatment of disease", Clin. Exp. Immunol., 79(3):15-321 (1990).
Specthrie, et al., "Construction of a microphage variant of filamentous bacteriophage", Mol. Biol., 228:720-724(1992).
Spink, et al., "Thermodynamics of forming a parallel DNA crossover", Biophysical Journal, 97(2):528-538 (2009).
Staple, et al., "Solution structure and thermodynamic investigation of the HIV-1 frameshift inducing element", Journal of Molecular Biology, 349:1011-1023 (2005).
Stephenson, et al., "Three-Dimensional RNA Structure of the major HIV-1 Packaging Signal Region", Structure, 21:951-962 (2013).
Sun, et al., "Casting inorganic structures with DNA molds", Science, 346(6210):1258361 (2014).
Tintore, et al., "DNA origami as a DNA repair nanosensor at the single-molecule level", Angew Chem Int Ed Engl.,52(30):7747-7750 (2013).
Tomley, et al., "M13 Phage Growth and Single-Stranded DNA Preparation", Methods Mol. Biol., 58:359-362 (1996).
Torring, et al., "DNA origami: a quantum leap for self-assembly of complex structures", Chem. Soc. Rev., 40:5636-5646 (2011).
Tumpane, et al., "Triplex addressability as a Basis for Functional DNA Nanostructures", 7(12):3832-3839 (2007).
Ubaidurrahman, et al., "A Novel DNA Computing Based Encryption and Decryption Algorithm", Procedia Comput Sci., 46:463-475 (2015).
Ui-Tei, et al., "Sensitive assay of RNA interference in *Drosophila* and Chinese hamster cultured cells using firefly luciferase gene as target", FEBS Lett, 479(3):79-82 (2000).
Untergasser, et al., "Primer3—new capabilities and interfaces", Nucleic Acids Res. 40(15): e115-e115 (2012).
Veneziano, et al., "Designer nanoscale DNA assemblies programmed from the top down", Science, 352(6293):1534 (2016).
Veneziano, et al., "Designer nanoscale DNA assemblies programmed from the top down", Science, Supplementary Materials (2016).

(56) References Cited

OTHER PUBLICATIONS

Veneziano, et al., "Enzymatic Synthesis of gene-length single-stranded DNA", bioRxiv (2017).
Vogel, et al., Hfq and its constellation of RNA, Nature Reviews Microbiology. 9:578-589 (2011).
Wahlestedt, et al., "Potent and nontoxic antisense oligonucleotides containing locked nucleic acids", Proc. Natl Acad. Sci. USA, 97(10):5633-5638 (2000).
Wang, "Double-stranded DNA homology produces a physical signature", PNAS, 107(28):12547-12552 (2010).
Wang, et al., "An atomic model of brome mosaic virus using direct electron detection and reasl-space optimization", Nature Communications, 5(4808) (2014).
Watts, et al., "Architecture and secondary structure of an entire HIV-1 RNA genome", Nature, 460:711-716 (2009).
Wei, et al., "Complex shapes self-assembled from single-stranded DNA tiles", Nature, 485(7400): 623-626 (2012).
Wilkinson, et al., "Selective 2'-hydroxyl acylation analyzed by primer extension (SHAPE): quantitative RNA structure analysis at single nucleotide resolution", Nature Protocols, 1(3)1610-1616 (2006).
Winfree, et al., "Design and self-assembly of two-dimensional DNA crystals", Nature, 394(6693):539-544 (1998).
Winter, et al., "Making antibodies by Phage Display Technology", Annu Rev Immunol., 12:433-455 (1994).
Wong, et al., "Organic Data Memory Using the DNA Approach", Communications of the ACM, 46:95-98 (2003).
Woo, et al., "Programmable molecular recognition based on the geometry of DNA nanostructures", Nat. Chem., 3(8):620-627 (2011).
Wooddell, et al., "Use of asymmetric PCR to generate long primers and single-stranded DNA for incorporating cross-linking analogs into specific sites in a DNA probe", Genome Res. 6(9):886-892 (1996).
Wynn, et al., "HIV-1 drug discovery: targeting folded RNA structures with branched peptides", Organic & Biomolecular Chemistry, 13, 5848-5858 (2015).
Xu, et al., "Design of 240,000 orthogonal 25mer DNA barcode probes", PNAS., 106(7):2289-2294 (2009).
Xuan, "Ultrasound-responsive block copolymer micelles based on a new amplification mechanism", Langmuir, 28(47):16463-16468 (2012).
Yan, et al., "DNA-templated self-assembly of protein arrays and highly conductive nanowires", Science, 301:1882-1884 (2003).
Yang, et al., "Self-assembly of DNA rings from scaffold-free DNA tiles," Nano Letters, 13(4):1862-1866 (2013).
Yazdi, et al., "A Rewritable, Random-Access DNA-Based Storage System", Scientific reports, 5:14138 (2015).
Yim, et al., "The Essential Component in DNA-Based Information Storage System: Robust Error-Tolerating Module", Frontiers in bioengineering and biotechnology, 2:49 (2014).
Zhang, et al., "Complex wirefram DNA origami nanostructure with multi-arm junction vertices", Nature Nanotechnology, 10: 779-785 (2015).
Zhao, et al., "Organizing DNA origami tiles into larger structures using preformed scaffold frames", Nano Lett., 11(7):2997-3002 (2011).
Zhirnov, et al.," Nucleic acid memory", Nat Mater., 15(4):366-70 (2016).
Zuckermann, et al., "Efficient method for the preparation of peptoids [oligo(N-substituted glycines)] by submonomer solid-phase synthesis", J. Am. Chem. Soc., 114(26):10646-10647(1992).
Banal, et al., "Random access DNA memory in a scalable, archival file storage system", bioRxiv, 1-29 (2020).
Bee, et al., "Content-Based Similarity Search in Large-Scale DNA Data Storage Systems", bioRxiv, 1-19 (2020).
Irobalieva, et al., "Structural diversity of supercoiled DNA", Nat. Commun., 6(8440):1-10 (2015).
Jones, et al., "Nanomaterials. Programmable materials and the nature of the DNA bond", Science, 347(6224):840; 1260901-1-12060901-11 (2015).

Kuang, et al., "Nanoscale Superstructures Assembled by Polymerase Chain Reaction (PCR): Programmable Construction, Structural Diversity, and Emerging Applications", Accounts of Chemical Research, 46(11):2341-2354 (2013).
Ledsgaard et al., "Basics of Antibody Phage Display Technology," Toxins, 10(236), 15 pages (2018).
Li, et al., "Engineering nucleic acid structures for programmable molecular circuitry and intracellular biocomputation", Nature Chemistry, 9(11):1056-1067 (2017).
Lin, et al., "Dynamic and scalable DNA-based information storage", Nature Communications, 11(1):2981 (2020).
Lutz, et al., "Sequence-controlled Polymers", Science, 341(6146):628;1238149-1-1238149-8 (2013).
Martin, et al., "Magnesium-free self-assembly of multi-layer DNA objects", Nat. Commun., 3(1103):1-6 (2012).
Nayak, et al.. "Cas9-mediated genome editing in the methanogenic archaeon Methanosarcina acetivorans", PNAS, 114(11):2976-2981 (2017).
New England Biolabs: Catalog #N4018S, 8 pages (2007).
New England Biolabs: Catalog #N4040S, 13 pages (2007).
Norton, et al., "Templates for sequential Assembly of DNA Based Nanostructures", Proceedings of 2005 5th IEEE Conference on Nanotechnology, 3 pages (2005).
Pan, et al., "Lattice-free prediction of three-dimensional structure of programmed DNA assemblies", Nature Communications., 5(5578):1-7 (2014A).
PartBBa_K1445000, Registry of Standard Biological Parts, Group: IGEM14_CU-Boulder (2014).
Perrault and Shih, "Virus-inspired membrane encapsulation of DNA nanostructures to achieve in vivo stability," ACS Nano, 8(5):5132-5140 (2014).
Rashid, et al., "The strategies of DNA immobilization and hybridization detection mechanism in the construction of electrochemical DNA sensor: A review," Sensing and Bio-Sensing Research vol. 16, pp. 19-31,doi:10.1016/j.sbsr.2017.09.001 (2017).
Rhoads, et al., "PacBio Sequencing and Its Applications", Genomics, Proteomics and Bioinformatics, 13(5):278-289 (2015).
Sattar, et al. , "Ff-nano, short functionalized nanorods derived from Ff (f1, fd, or M13) filamentous bacteriophage", Front Microbiol., 6(316):1-13 (2015).
Seq ID No. 1-139 Alignment, 3 pages (Year: 2020).
Shaik, et al., "CySpanningTree: Minimal Spanning Tree computation in Cytoscape [version 1; peer review: 1 approved, 1 approved with reservations]", F1000 Research , 4(476) 11 pages (2015).
Shepherd, et al., "Bioreproduction of pure, kilobase-scale single-stranded DNA", Scientific Reports, 9(6121):1-9 (2019).
Shilling, et al., "Structure and Function of *Escherichia coli* Type 1 Pili: New Insight into the Pathogenesis of Urinary Tract Infections", The Journal of Infectious Diseases, 183(Suppl.1): S36-S40 (2001).
Sun, et al., "Casting inorganic structures with DNA molds", Science, 346(6210):1-24 (2014).
Veneziano, "Suoplementary Materials for designer nanoscale DNA assemblies programmed from the top down", Science, 352(6293):S1-S67 (2016).
Veneziano, et al., "Designer nanoscale DNA assemblies programmed from the top down", Science, 352(6293) 1534: 1-21 (2016).
Veneziano, et al., "Enzymatic Synthesis of gene-length single-stranded DNA", bioRxiv, 6 pages (2017).
Wang, et al., "An atomic model of brome mosaic virus using direct electron detection and real-space optimization", Nature Communications, 5(4808):1-12 (2014).
Yazdi, et al., "A Rewritable, Random-Access DNA-Based Storage System", Scientific reports, 5(14138): 1-10 (2015).
Yim, et al., "The Essential Component in DNA-Based Information Storage System: Robust Error-Tolerating Module", Frontiers in bioengineering and biotechnology, 2(49):1-5 (2014).
Yuan, et al., "Solid-State Nanopore", Nanoscale Res Lett., 13: 56 (2018).

(56) References Cited

OTHER PUBLICATIONS

Zhou, et. al., "A new biochromatography model based on DNA origami assembled PPARy: construction and evaluation", Anal. Bioanal. Chem., 409(12):3059-3065 (2017).

* cited by examiner

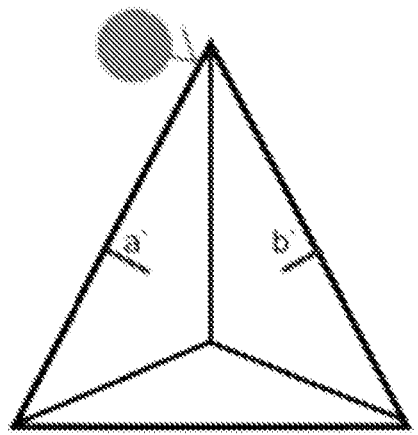
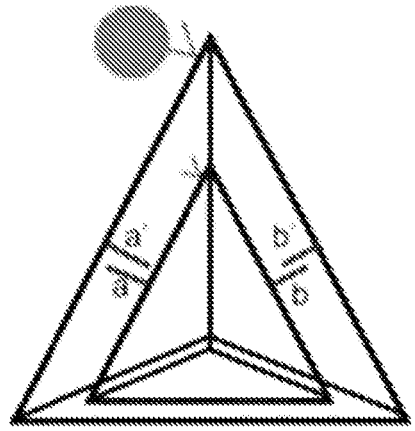
FIG. 7C  FIG. 7D
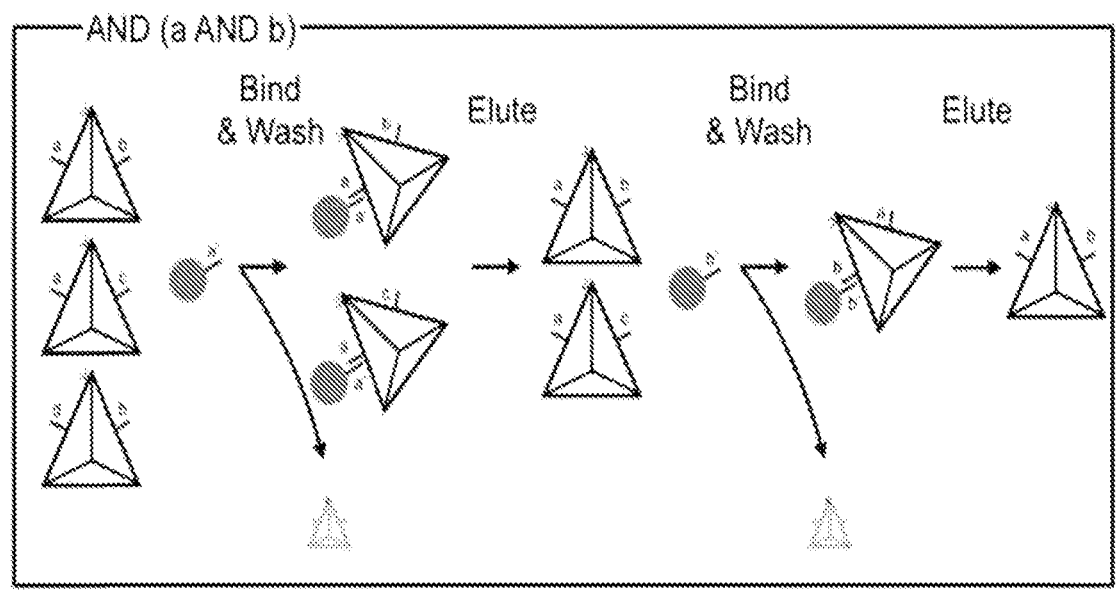
FIG. 8

| Element | Scheme | Feature |
|---|---|---|
| Structured Nucleic Acid Memory Block | | Avoid aggregation of ssDNA, using basepaired dsDNA |
| Scalable Memory Block Size | | Distinct Size and reusable memory blocks |
| Indices or File Handles | | ssDNA barcodes for multiple indices |
| Associative Memory | | Rapid retrieval and re-assortment of associated or categorized data |
| Logic | | Sequential Logic Operations for RAM |

FIG. 14

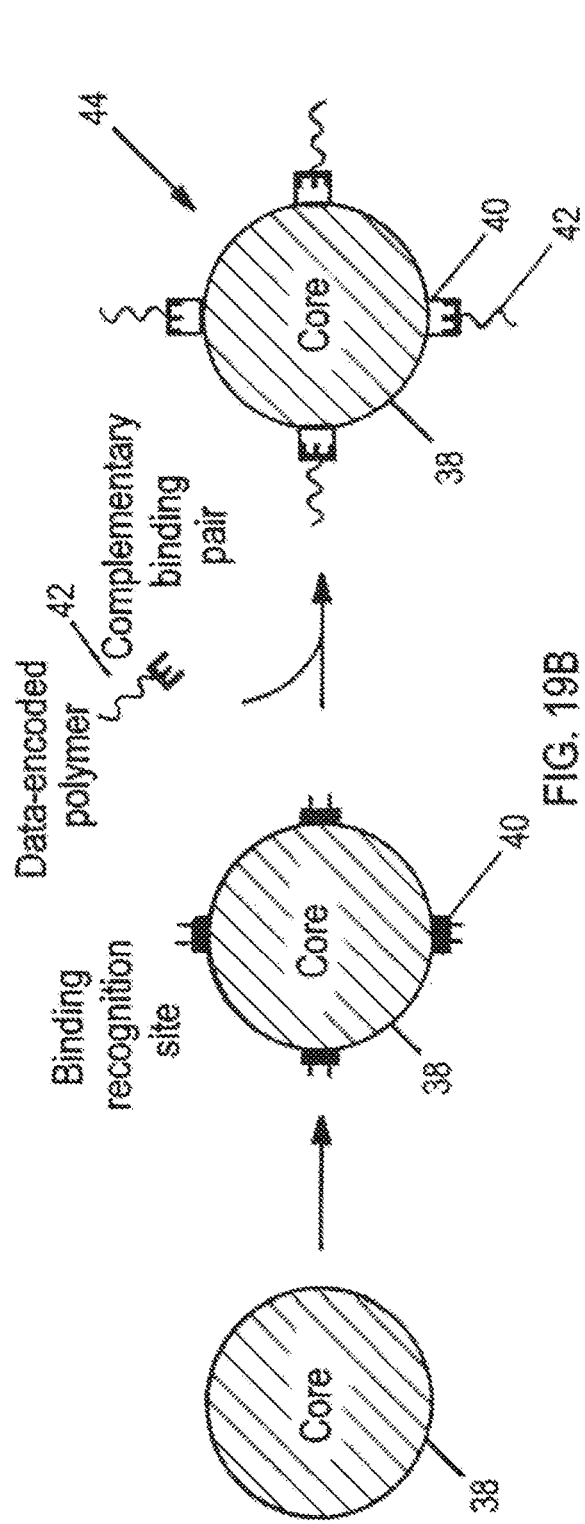
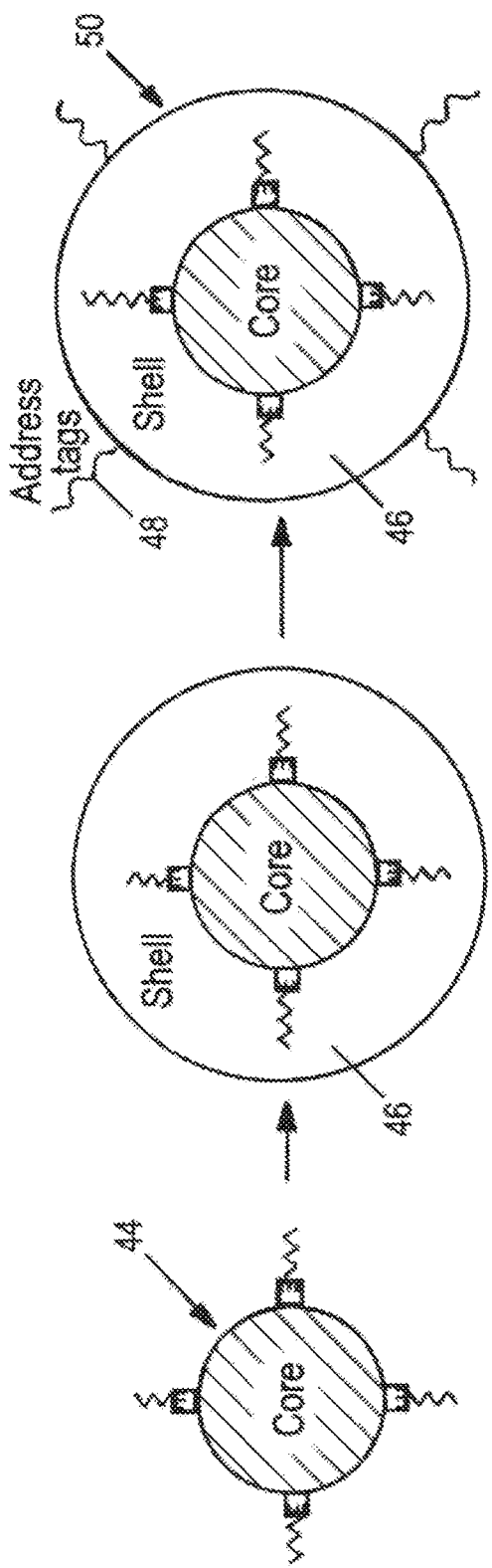
FIG. 19B
FIG. 19C

SEQUENCE-CONTROLLED POLYMER RANDOM ACCESS MEMORY STORAGE

CROSS-REFERENCE TO RELATED APPLICATIONS

This application is a National Phase application under 35 U.S.C. § 371 of PCT/US2017/029948 filed Apr. 27, 2017 entitled "SEQUENCE-CONTROLLED POLYMER RANDOM ACCESS MEMORY STORAGE," which claims the benefit of and priority to U.S. Ser. No. 62/328,455 filed Apr. 27, 2016 and U.S. Ser. No. 62/356,885 filed Jun. 30, 2016 the contents of which are incorporated by reference in their entirety.

STATEMENT REGARDING FEDERALLY SPONSORED RESEARCH

This invention was made with government support under Grant Nos. N00014-14-1-0609 and N00014-16-1-2181 awarded by the Office of Naval Research. The government has certain rights in the invention.

FIELD OF THE INVENTION

The present invention relates generally to methods of storing, processing, and selectively retrieving information encoded within sequence-controlled polymer barcoded nanoparticles.

BACKGROUND OF THE INVENTION

Information and communication technologies generate vast amounts of data that will far eclipse today's data storage capacity. Information storage has gone through many stages of growth during the course of modern civilization. Libraries acting as repositories of information and using an indexed approach were categorized by various methods such as the Dewey Decimal System. Physical storage of digital information was initiated by programming to punch-card-based readers. The storage and growth of computers in modern society has led to digitization of information archives, and a rapid search of that data. However, this growth is outpacing the ability to store all of the information that needs to be inventoried. Memory materials must therefore be suitable for high-volume manufacturing. At the same time, they must have elevated information stability and limit the energy consumption and trailing environmental impacts that such storage will demand. Analysts estimate that global memory demand—at $3 \times 10^{24}$ bits—will exceed projected silicon supply in 2040 (Zhimov V et al., *Nat Mater.* 23; 15(4):366-70 (2016)). To meet such requirements, flash-memory manufacturers would need $\sim 10^9$ kg of silicon wafers even though the total projected wafer supply is $\sim 10^7$-$10^8$ kg (Zhimov V et al., *Nat Mater.* 23; 15(4):366-70 (2016)). Such forecasts motivate an exploration of unconventional materials with cost-competitive performance attributes.

DNA has previously been shown to be an outstanding material for use in archival or long-term information storage. The data storage density of DNA is massive, implemented up to 2.2 PB/gram of DNA (Goldman, N et al., *Nature.* 494, 77-80 (2013)), and the long-term fidelity of the information can last for thousands of years in its dry state with very little energy required for maintenance (Zhimov, V et al., *Nature materials.* 15, 366-370 (2016)). Furthermore, the raw material is much more abundant than the ultra-pure wafer silicon required for the manufacture of the most prevalent current memory storage devices (Zhimov, V et al., *Nature materials.* 15, 366-370 (2016)). This information storage density compares with archival tape-based storage that is currently the highest density storage medium by 8 orders of magnitude, with tape-based storage having a life-time rating of only 10-30 years (Bornholt, J et al., 21th *ACM International Conference on Architectural Support for Programming Languages and Operating Systems.* (2016)).

Previous applications using DNA to store information have been implemented as the storage of books, sonnets, sound clips, images, and online webpages (Goldman, N et al., *Nature.* 494, 77-80 (2013); Church, G M et al., *Science.* 337, 1628 (2012); Yazdi, S M et al., *Scientific reports.* 5, 14138 (2015); Yim, A K et al., *Frontiers in bioengineering and biotechnology.* 2, 49 (2014)). In each case, DNA memory has been stored in either linear double-stranded (~700-1,000 nucleotides) or short single-stranded (~125 nucleotide) oligonucleotide sequences using a variety of encoding strategies. These coding strategies have been simple direct to base (Church, G M et al., *Science.* 337, 1628 (2012); Clelland, C T et al., *Nature.* 399, 533-534 (1999); Wong, P C et al., *Communications of the ACM.* 46, 95-98 (2003)), Huffman code (Goldman, N et al., *Nature.* 494, 77-80 (2013); Bornholt, J et al., 21th *ACM International Conference on Architectural Support for Programming Languages and Operating Systems.* (2016); Ailenberg, M et al., *BioTechniques.* 47, 747-754 (2009)), compressed (Yim, A K et al., *Frontiers in bioengineering and biotechnology.* 2, 49 (2014)), and encrypted (Babaei, M., *Nat Comput.* 12, 101-107 (2013); Cui, G Z et al., 2008 *Third International Conference on Bio-Inspired Computing: Theories and Applications.* 37-41(2008); Gehani, A et al., *Lect Notes Comput Sc.* 2950, 167-188 (2004); Leier, A et al., *Biosystems.* 57, 13-22 (2000); UbaidurRahman, N H et al., *Procedia Comput Sci.* 46, 463-475 (2015)). Random access of direct encoded memory has only been demonstrated by PCR methods using barcoding strategies and spatial segregation of information pools into distinct wells (Bornholt, J et al., 21th *ACM International Conference on Architectural Support for Programming Languages and Operating Systems.* (2016); Yazdi, S M et al., *Scientific reports.* 5, 14138 (2015)).

These approaches have major limitations for the implementation with large data sets. Specifically, with large data sets, the data need to be edited, to delete information rather than having to resynthesize the entire pool. The inherent limitations on specificity involved in barcoding DNA translates to the current requirement of separating data into separate containers to allow for specific reads. Adding and then directly computing on metadata added dynamically to the data is not allowable in current DNA memory proposals, as the single-stranded DNA causes non-specific interactions and large-scale aggregation. Yazdi et al. (Yazdi, S M et al., *Scientific reports.* 5, 14138 (2015)) reported on specific barcoding of encoded data, using mutagenesis with enzymes relying on polymerase chain reactions, which necessitates buffer exchanges and addition of unknown biological elements into the memory pool during editing, with all prior data fragments left in the pool and new data being added with new barcodes (Yazdi, S M et al., *Scientific reports.* 5, 14138 (2015)). Old defunct data is left in the memory pool. Bornholt, et al. (Bornholt, J et al., 21th *ACM International Conference on Architectural Support for Programming Languages and Operating Systems.* (2016)) also use a specific barcode approach, with an external database for storing the reference key to the primer for data selection. They implement two functions, PUT and GET, to add data to the pool and amplify a specific piece of data in the pool using PCR and downstream sequencing.

Thus several problems exist in all current implementations of random access of DNA-encoded memory. Methods relying on PCR are prone to off-target amplification, especially in the presence of many single-stranded sequences as in Bomholt, J et al., 21*th ACM International Conference on Architectural Support for Programming Languages and Operating Systems*. (2016). Therefore, any given pool of information requires many different primers to distinguish all keys, which increases the chance that two primers react poorly to each other. Further, a requirement for PCR for each block of information necessitates many PCR reactions to extract even a single page. For example, Bomholt, et al. encodes 1-2 words per block of information, implying 250-500 highly specific PCR reactions per written page, then implying that it would require up to 100,000 highly specific PCR reactions with a 200-page book. This would be both tedious and costly. Without additional selections, only a single level of data selection can be used, be it at the page, book, author, or section level, but no published scheme can satisfy selection with multiple conditions. Single, hard-coded addressing of the data does not allow for any additional computation on the data between synthesis and sequencing. Any selection of the data requires sequencing the whole block of information and then further computation on that sequenced, decoded data. For example, in the implementations in Bornholt, et al. and Yazdi, et al. (Bornholt, J et al., 21*th ACM International Conference on Architectural Support for Programming Languages and Operating Systems*. (2016); Yazdi, S M et al., *Scientific reports*. 5, 14138 (2015)), if the barcode tables were selected at the book level, one could sequence and read out all 464 pages of the book addressed as *The Grapes of Wrath*, but could not select out to just sequence and read page 394. Classical, linear DNA pools do not offer spatial isolation and so a pool contains data for many different keys which are irrelevant to a single read operation. Therefore, isolating only the molecule of interest is non-trivial, and so existing DNA storage techniques generally sequence the entire solution which incurs significant cost and time overheads. In addition, by hard-coding addresses into the data blocks, once the data is synthesized, any changes to the address space would require re-synthesis of the entire data pool. In any published work, no deletion operations on DNA-encoded data has been reported. Only Yadzi, et al. (Yazdi, S M et al., *Scientific reports*. 5, 14138 (2015)) proposes re-writability of the data, but old data remains in the pool for more and more accumulation of junk DNA in large data sets, without the ability to clean the pool. Use of PCR for amplification necessitates buffer exchanges and addition of biological components to the pool or subset of the pool. Introduction of biological components, even of extreme purity will lower the lifetime of the DNA, especially in the case of single-stranded DNA where many PCR polymerases have exonuclease activity. No specified nano-structuring of DNA-encoded data blocks have been reported. In contrast, DNA strands are typically stored in "pools" that have stochastic spatial organization and do not permit structured addressing, unlike electronic storage media. Beyond spatial segregation into distinct containers (Bomholt, J et al., 21*th ACM International Conference on Architectural Support for Programming Languages and Operating Systems*. (2016)), no methods to associate DNA-encoded data with other DNA-encoded data by spatial segregation in the same solution have been reported. Further, current systems that employ sequence address tags limit the address space to the barcode length ($4^n$, where n is the number of nucleotides).

Therefore, it is an objective of the current invention to provide a biopolymer-encoded memory structure, which may include peptides, nucleic acids, or other sequence-controlled polymers, that allows Boolean logic computations.

It is also an objective of the current invention to provide arbitrary nucleic acid origami nanostructures and other nucleic acids and biopolymers as memory blocks, which can be read out either using sequencing or mass spectrometry or other analytical chemical approach.

It is a further objective to provide nucleic acid memory blocks that are capable of forming stable and reconfigurable superstructures for association of memory block structures and position-based storage, as well as parallel computational processing.

It is also an objective to provide nucleic acid memory objects that are capable of accelerated degradation in response to specific external stimuli.

SUMMARY OF THE INVENTION

Methods of storing and organizing information encoded within sequence-controlled biopolymers formed into bar-coded nanoscale particles have been developed. Bio-polymers, such as nucleic acids, polypeptides, or other sequence-controlled polymer macromolecules containing encoded data are encapsulated or folded into nanoparticles that are barcoded and act as discrete memory blocks. The methods allow for controlled segregation of blocks of information encoded by a biopolymer sequence, such as a nucleic acid sequence, with rapid retrieval based on multiply addressing the nanoparticles.

The information encoded within the sequence-controlled polymer of each memory block corresponds to one or more labels or "barcodes" encoded within address tags present at the surface of the block.

Exemplary sequence controlled polymers that can be encoded with information include naturally occurring and non-naturally occurring nucleic acids, such as DNA, RNA, PNA, and LNA, amino-acid based sequences such as polypeptides, including alpha-peptides and beta-peptides, peptidomimetics, such as delta peptide and gamma-peptides, as well as block co-polymers, carbohydrates, and chemically-derived (synthetic) polymer sequences. Single-stranded overhang nucleic acid sequences with programmable high affinity and specificity are used for adding multiplexed addresses and/or purification tags to the memory blocks for data sorting, retrieval and molecular computation.

In some embodiments, memory blocks are formed by encapsulating one or more sequence-controlled polymers within one or more encapsulating agents. Exemplary encapsulating agents include proteins, lipids, saccharides, polysaccharides, nucleic acids, and any derivatives thereof, as well as hydrogel and synthetic polymers including polystyrene, or silica, glass, and paramagnetic materials. These encapsulated bio-polymers form discrete memory storage units that allow for controlled segregation of blocks of information. In some embodiments, memory blocks include sequence-controlled bio-polymers folded into a specific nano-structured form, such as a nucleic acid nanostructure. In some embodiments, a memory block includes one or more discrete units of information encoded within more than one type of sequence-controlled biopolymer. For example, in some embodiments, information is encoded within a nucleic acid sequence that is folded into a nucleic acid nanostructure, which contains or is associated with one or more polypeptides or other sequence-controlled bio-polymers into which information has been encoded. In some embodiments, a memory block includes a nucleic acid sequence into which information is encoded, encapsulated together with one or more polypeptides or other sequence-controlled bio-polymers into which information has been encoded.

In some embodiments, information is encoded within a nucleic acid "scaffold" sequence that is folded into a nucleic acid nanostructure. The nucleic acid scaffold sequences encoding information can be of any length, for example, from 100-1,000,000 nucleotides. Typically, nucleic acid scaffold sequences are between 300-500,000 nucleotides, for example, from about 300 nucleotides to about 51,000 nucleotides in length, inclusive. In some embodiments, the methods provide the sequences of short single-stranded oligonucleotides staple strands of approximately 14-1,000 nucleotides in length, for example, approximately 14-60 nucleotides, which fold a single-stranded nucleic acid scaffold sequence into a nucleic acid nanostructure (e.g., polyhedron or DNA brick) having user-defined arbitrary geometries. Typically, the assembly of a nucleic acid nanostructure includes scaffold routing, staple strand selection, geometry and scaffold sequence inputs, oligonucleotide synthesis, and folding ("nano-structuring"), as performed with either scaffolded nucleic acid origami or non-scaffolded nucleic acid origami. The staple strands have nicks as part of the formation of the nanostructure, where the 5' end of the staple meets the 3' end of itself or another staple. These nicks can then have single-stranded overhang nucleic acid sequences of arbitrary sequence ("tags").

The methods also provide nucleic acid encapsulation for memory storage, with nucleic acids encoding a format of data being encapsulated within a layer of natural, or synthetic material. A nucleic acid of any arbitrary form can be encapsulated, for example, a linear, a single-stranded, base-paired double stranded, or a scaffolded nucleic acid. Exemplary encapsulating agents include proteins, lipids, saccharides, polysaccharides, nucleic acids, and any derivatives thereof, as well as hydrogel and synthetic polymers including polystyrene, or silica, glass, and paramagnetic materials. These encapsulated nucleic acids form discrete memory storage units that allow for controlled segregation of blocks of information.

Therefore, methods for creating Sequence-controlled polymer Memory Objects ("SMOs") are provided. In some embodiments, the memory objects are nucleic acid nanostructures or nucleic acid encapsulated units that represent Nucleic acid Memory Objects ("NMOs"). The SMO memory "blocks" can be of variable size, are reconfigurable based on extrinsic cues, including buffer changes, enzymes, nucleic acid "keys," temperature, electrical signals or light, and present identity tags for physical identification and retrieval or selection. The methods include assembling SMOs together into larger supra-memory blocks for spatially associating SMOs for segregation and associative memory applications. The methods also include functionalizing the staple strands to have tags that can be used for capture, rapid purification, and computation on SMOs. The methods provide information as physical, structured units having arbitrary geometry and size that can be used to form supramolecular memory blocks. Selection of information is based on both sequences and geometries of the SMOs. Nano-structuring, or encapsulating the data blocks allows for a natural extension to spatial segregation of data based on input signals, associating related information into supra-block memory. The address space is multiplied by the number of tags in use, so $4^{(k*n)}$ where n is the number of nucleotides of the address per tag and k is the number of tags.

Selection and access of information can be achieved by capture of SMOs mediated by specific and orthogonal interaction of the single-strand overhang tags. Overhang tags available in primer libraries known in the art can be included (Xu, et a. *PNAS.*, V. 106, (7) pp. 2289-2294 (2009)).

Therefore, methods include selection of data at any user-defined level, depending upon the number of tags included in the design of the SMOs. For example, if multiple books are encoded using the described methods, selection criteria can include one or more elements specific for a single book or subset of books, such as author name, genre, or title, or even a single page of a single selected book, or even a single passage or phrase from a single page. Memory blocks may be re-used for different archival memory storage applications, for example, words in the English language are re-used, or any other fundamental memory unit of interest that is encoded in the structured nucleic acid memory block is re-used.

Tags from functionalized staple strands can be modified with a new addressing system, and the polymer encoding bitstream data can be refolded with the new set of tagged staples, and/or overhang sequences. This allows for a dynamic addressing system that does not require re-synthesis of all the data. Sequence-based polymers encapsulated in silica or paramagnetic or polymer-based nanoparticles can similarly be re-used, with display tags covalently or non-covalently attached through standard chemistries, specifying the number and stoichiometric ratios of specific overhang sequences. Methods for accessing information, or subsets of information from a pool of discrete SMOs are also provided. In some embodiments, accessing data is carried out to enable selection via Boolean logic. For example, Boolean NOT logic can be used to delete information from a data pool. In some embodiments deleted information is replaced, for example, with a new structure and set of addresses. In other embodiments, deleted data is omitted from future computations/selections.

In some embodiments, the methods also optionally include long-term storage of SMOs. For example, the methods can include storage of scaffolded nucleic acid, or encapsulated nucleic acid for up to one year, up to one decade, up to two decades, three decades, or more than three decades. Typically, the methods do not include steps or processes detrimental to the stability and long-term storage of SMOs. For example, only selected outputs are processed by either PCR or sequencing. There are no required additions of new buffers and biological materials that can degrade the data. In some embodiments, DNA is stored in dry state to maximize its lifetime. When DNA is stored in dry state, appropriate mechanisms and systems can be used to segregate, order store and rehydrate the dry SMOs, for example, lyophilization and/or freezing of NMOs. In some embodiments, paper-based storage is used. Paper-based storage offers segregation of numerous nucleic acid memory solutions, or compartments that can be hydrated for selection and sequencing only when needed for memory retrieval. In further embodiments, systems include digital droplet-based microfluidics, for example, on electromagnetically actuated surfaces or in solution. Digital droplet-based microfluidics offer practical means of performing the wet biochemistry needed for the selection and retrieval steps. Therefore, in some embodiments, the methods include the use of digital droplet-based microfluidics for performing selection and retrieval steps.

In some embodiments, the memory objects are scaffolded nucleic acid nanostructures having a desired polygon or polyhedral shape. Therefore, in some embodiments, the methods include providing a bitstream-encoded nucleic acid sequence; creating a nucleic acid nanostructure, or a nucleic acid encapsulation unit that contains the sequence; and storing the nucleic acid nanostructure, or a nucleic acid encapsulation unit that contains the sequence.

In some embodiments, the methods also optionally include organizing information within memory objects, such as nucleic acid nanostructures, or nucleic acid encapsulation units. In some embodiments, the methods also optionally include accessing the bitstream-encoded sequence. In further embodiments, the methods include retrieving the bitstream-encoded sequence from the memory object.

Biopolymer memory objects formed according to the methods for encoding information within one or more sequence-controlled bio-polymers are also described. Nucleic acid memory objects formed from nucleic acids including bit-stream data are also provided. In some embodiments, the nucleic acid memory objects include a scaffold single-stranded nucleic acid of arbitrary length that is folded around the entire structure. Theoretically there is no limit to the size of the nucleic acid scaffold strand that is folded around the entire structure, however, in practical terms, the single-stranded nucleic acid scaffold typically includes between about 100 and 1,000,000 nucleotides. In some embodiments, the nanostructures also include one or more staple strands including one or more overhang oligonucleotide sequences. The staple strands are custom-designed to anneal to the scaffold strand to form any desired three dimensional nanostructure containing the bit-stream data. In some embodiments, the one or more overhang oligonucleotide sequences are address tags. Exemplary address tags include barcode sequences of approximately 4 to at least 30 nucleotides in length (Xu, et al., *PNAS.*, V. 106, (7) pp. 2289-2294 (2009)). In some embodiments the nucleic acid nanostructure has a geometric shape of a regular or irregular wireframe polyhedron. Typically, the geometric shape offers accessibility to the internal memory blocks by nucleic acids and enzymes. Therefore, in some embodiments the shape of the structure enables selection, or retrieval, or reconfiguration of the memory block, for example, due to porosity of the overall supra-molecular memory structure. Therefore, in certain embodiments, the desired target structure is one that offers diffusion of small molecules throughout it, for example, to provide access to enzymes and/or other molecules, such as nucleic acids. In other embodiments, the desired target structure prevents access of enzymes and/or other molecules, such as nucleic acids. In some embodiments, the SMO consists of a hydrogel, polymer, glass, silica, or paramagnetic nanoparticle with specific overhang nucleic acid sequence or other high affinity and specificity tags that offer programmable interactions between distinct memory blocks encoded in SMOs. Therefore, in some embodiments, the shape of the structure itself can be used as a means to select different or similar functionalities amongst SMOs.

Sequence-controlled biopolymer memory objects including nucleic acids or other sequence-controlled biopolymers that encode a format of data, encapsulated within natural, or synthetic material, are also provided. In some embodiments, a nucleic acid or other biopolymer of any arbitrary form can be encapsulated. For example, in some embodiments a linear, a single-stranded, a base-paired double stranded, or a scaffolded nucleic acid is encapsulated. Exemplary encapsulating agents include proteins, lipids, saccharides, polysaccharides, nucleic acids, synthetic polymers, hydrogel polymers, silica, paramagnetic materials, and metals, as well as any derivatives thereof. These encapsulated nucleic acids or other biopolymer are associated with one or more overhang nucleic acid sequences that are used for adding addresses, and/or purification tags. In some embodiments, multiple layers of encapsulation and overhang nucleic acids are designed for additional sorting and tagging the format of information.

In some embodiments, the memory object has the geometric shape of a compact brick-like user-defined structure that can also stack end-to-end into long ribbons or into extended 2D or 3D crystalline-like arrays via either non-specific or specific stacking interactions that are controlled using buffer or nucleic acid overhangs or other physical association. In some embodiments, the one or more staple strands include "overhang" oligonucleotide sequences that are complementary to one or more staple strands from a different memory object, such as a different nucleic acid nanostructure, or to a bridging oligonucleotide. In some embodiments, one or more memory objects are organized into superstructures via complementarity of the nucleotide sequences from the one or more staple strands, or to the bridging nucleotide. For example, in some embodiments, nucleic acid nanostructures are organized into superstructures via complementarity of the nucleotide sequences from the one or more staple strands, or to the bridging nucleotide. In some embodiments, memory objects such as nucleic acid nanostructures or encapsulated nucleic acids are organized into superstructures based on user-defined associations between the memory blocks, noted above. The super-structured data can then be specifically manipulated by external signals including pH, temperature, salts, nucleic acids, enzymes, light, etc. as well as microfluidic operations that may be droplet-based on-chip using electro-wetting or traditional 2-phase flow-based microfluidics. Application of mixing and splitting operations on selective pools of SMOs as well as other beads or reagents including cutting enzymes such as Cas9 or restriction enzymes offers ability to perform both complex and selective computation as well as memory manipulation and retrieval.

BRIEF DESCRIPTION OF THE DRAWINGS

FIG. 1A depicts diversity in the size over several orders of magnitude of nanostructured memory objects that each have equivalent morphology (depicted as a closed cube), but which include between 0.5 kb to 100 kb of data, respectively. FIG. 1B is a schematic depicting several memory objects, each having diversity in geometry, including open wireframe polyhedra and compact brick-like geometries. FIG. 1C is a schematic depicting several memory objects having diversity in the number and orientation of single-stranded nucleic acid overhangs that are presented outwards at pre-defined geometric positions as one of several means of specifically associating multiple memory blocks into larger scale assemblies that can be stable or reconfigured or accessed in response to extrinsic cues.

FIG. 4A depicts single- or double-stranded DNA, RNA, PNA, LNA, or other nucleic acids or peptides or other sequence-controlled polymer encoding the bit stream data (2), either with known/characterized errors in polymer sequence, or high-fidelity sequence. The sequence-controlled polymers, such as nucleic acids, are "packaged", "encapsulated", "enveloped", or "encased" (4) in gel-based beads, protein viral packages (e.g., M13, adeno-associated virus, etc.), micelles, mineralized structures, siliconized structures, metals, paramagnetic materials, or designed polymers (6) that enclose or include one nucleic acid encoding data for multiplexed data storage using diverse polymers and polymer types (FIG. 4B) or more than one nucleic acid encoding data (2, and 3) (FIG. 4C). These packaged nucleic acids (10) carrying bitstream data have molecular identifiers such as single-stranded tag sequences, or any purification tags (8) to allow specific data selection and/or retrieval using Boolean logic (FIG. 4D).

FIGS. 7A-7D are schematic illustrations depicting selection of the NMO based on both sequence and geometry placement of the overhang. FIGS. 7A and 7B depict tetrahedral NMOs displaying a and b tags on specific edges; FIG. 7C depicts a complementary geometric DNA nanostructure on a capture support, displaying a' and b' at positions to capture NMOs with a and b tags at appropriate geometric locations; FIG. 7D depicts a NMO with complementary a and b tags displayed at specific edges are selected by the larger DNA nanostructures. In this way, a NMO is specifically selected based not just on sequence of the overhang tags, but also on the geometry of the NMO. Tetrahedra are representative of any memory objects, including encapsulated nucleic acids or other information-bearing biological or synthetic polymers.

FIG. 8 is a schematic illustration depicting the workflow for the method used to compute an AND logic operation on the NMO pool. A pool of differently addressed NMOs is depicted; a support is used to capture NMOs with overhang sequence a, resulting in a pool of NMOs having two different configurations of address tags (a,b; and a,c, respectively) captured NMOs having overhang sequence a are then released from the support; a support capturing NMOs further having overhang sequence b, released from the support; captured NMOs having overhang sequence b are then released from the support. Overall, this yields NMOs with overhang sequences a AND b by two-step capture purification. Tetrahedra are representative of any memory objects, including encapsulated nucleic acids or other information-bearing biological or synthetic polymers.

FIG. 14 is a schematic charts depicting the elements of an exemplary system for creating, storing and organizing information as re-useable "memory blocks" or computational molecular elements. A structured memory block, such as a cuboctahedron is shown as a square structured nucleic acid memory block. The memory blocks can be of many sizes, from small to as large, as needed to accommodate information. Each block can have multiple different file handles, or indices (depicted as a-d), allowing for multiple addressing of data for selections and operations. Specific modifications, such as overhang sequences, can be used to associate multiple blocks of information together into large super-blocks of memory, for rapid retrieval, re-assortment and computation with associated or categorized data. Modified overhangs also allow for use of Boolean logic AND, OR, and NOT operations on the memory blocks, for example, to select for purification of one or more memory blocks from a pool of memory blocks.

FIG. 15A demonstrates the work flow within one system for long-term storage of information in the form of molecular blocks of DNA. Any number of nucleic acid memory objects (e.g., 1-10's of millions) are blotted and freeze-dried to a long-term storage material ("paper") for segregation of data and for later retrieval. Dried memory blocks are selectively rehydrated by addition to blot with water or buffer. The process can be automated to selectively pull out the right spatially segregated memory pool, with the hydrated memory blocks being processed as described, and sequenced, for example by handheld devices, or bench-top sequencers. FIG. 15B is a flow chart describing the general approach towards molecular data storage and computation. Any digital files and folders from a computer. The digital files are encoded and/or converted to a molecular memory code (e.g., nucleotides, amino acids, polymers, atoms, surfaces. The code is written to the physical memory block used to store the data. The stored data is associated with a set of address codes to identify the memory block. The addresses are affixed to the memory block such that they can be used for subsequent reading, manipulation, selection, and computation, including physical tags, electrostatic or magnetic properties, chemical properties, or optical properties. The memory blocks with addresses are placed in a pool of other memory blocks for storage and computation. The pool is separated based on the physical properties, with some memory blocks satisfying the selection criteria and others not, and are sorted as such. Many cycles of this and other selection criteria can take place in parallel or in series. The sorted memory block(s) of interest are purified from the pool. The sorted memory block(s) are read out and decoded to digital format. The original digital file is retrieved from the pool.

FIG. 17A depicts a silica particle (18). FIG. 17B depicts the silica particle, modified (20) to allow adsorption of DNA particles. FIG. 17C depicts nucleic acid memory blocks (22) adsorbed to the surface-modified silica particles. FIG. 17D depicts a secondary silica shell (24) that is grown on the silica with the nucleic acid memory blocks adsorbed (26). This shell provides environmental protection for the nucleic acid memory blocks.

FIG. 18A depicts a single (monomer) NMO. FIGS. 18B-D each depict an exemplary "dimer" of two NMOs brought together at their vertices (FIG. 18B), along their edges (FIG. 18C), or at their faces (FIG. 18D), respectively, using overhang addressing. FIGS. 18E-18F each depict a "tetrahedra" of NMOs coming together in larger superstructures, as an extended tetramer addressed to come together along the edges via complementarity (FIG. 18E), and with different addresses, allowing assembly of a more compact configuration (FIG. 18F), respectively.

FIGS. 19A-19C are schematic illustrations depicting the molecular shelling of the memory objects. FIG. 19A is a scheme depicting the loading of a porous core (28) with multiple data-encoded polymers (30), shelling (32) and appending of address tags to the shelled memory object (36).

FIG. 19B is a scheme depicting the first stage in assembly of a memory object (44) from a core (38), to which recognition sites (40) are first bound, then data-encoded polymers (42) including one or more tags specific to the recognition sites bound to the core are complexed. FIG. 19C is a scheme depicting the final step of the assembly of the memory object (50) depicted in FIG. 19B. The core (44) and associated data-encoded polymers, are then encapsulated in a shell (46), to which the address tags (48) are then bound.

(FIG. 20B) data-encoded polymers (64) that are absorbed by a molecular core (62) are further surrounded by a molecular shell (68) and functionalized with addressing/specificity tags (66) for multiplexed computation (70). The shell or core has a readout based on optical, magnetic, electric, or physical properties of the shell/core.

FIG. 21A depicts a memory object formed from data streams encoded on a molecular core, which has a readout based on optical, magnetic, electric, or physical properties of the core. The molecular core contains address/specificity tags for molecular logic and data retrieval operations. FIG. 21B depicts a memory object formed from data streams encoded on a molecular shell surrounding a molecular core. The shell/core has readouts based on the optical, magnetic, electric, or physical properties of the shell/core. The shell is functionalized with addressing/specificity tags for molecular logic and data retrieval operations.

DETAILED DESCRIPTION OF THE INVENTION

I. Definitions

Figure 1A:
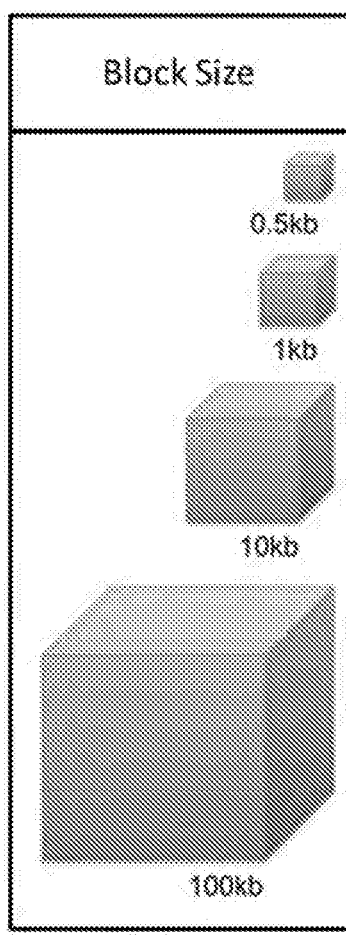
FIGS. 1A-1C are schematic representations of the data model described here, each showing different forms of diversity that can be generated within a pool of addressed memory objects.

The term "payload" refers to the actual body of data for transmission or for storage or computation. For example, in nucleic acid memory storage, the payload is encoded in the specified nucleotide sequence. The terms "desired data", "desired information" or "desired media" are used interchangeably to specify the payload information that is contained in the bit stream encoded sequence within a given memory object.

The term "bit stream encoded sequence" is any natural or synthetic sequence-controlled polymer sequence that encodes for data to be stored. For example, when nucleic acid is used to store data, the "bit stream encoded sequence" is the nucleic acid sequence that corresponds to the data that is encoded. Bit stream-encoded nucleic acid can be in the form of a linear nucleic acid sequence, a two-dimensional nucleic acid object or a three-dimensional nucleic acid object. Bit stream-encoded nucleic acid can include a sequence that is synthesized, or naturally occurring.

The term "bit" is a contraction of "binary digit". Commonly "bit" refers to a basic capacity of information in computing and telecommunications. A "bit" conventionally represents either 1 or 0 (one or zero) only, though other codes can be used with nucleic acids that contain 4 nucleotide possibilities (ATGC) at every position, and higher-order codecs including sequential 2-, 3-, 4-, etc. nucleotides can alternatively be employed to represent bits, letters, or words.

The terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs or modified nucleotides thereof, including, but not limited to locked nucleic acids (LNA) and peptide nucleic acids (PNA). An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides.

The terms "staple strands" or "helper strands" are used interchangeably. When used in the context of a nucleic acid nanostructure object, "Staple strands" or "helper strands" refer to oligonucleotides that work as glue to hold the scaffold nucleic acid in its three-dimensional geometry.

The terms "scaffolded origami", "origami" or "nucleic acid nanostructure" are used interchangeably. They can be one or more short single strands of nucleic acids (staple strands) (e.g., DNA) that fold a long, single strand of polynucleotide (scaffold strand) into desired shapes on the order of about 10 nm to a micron, or more. Alternatively, single-stranded synthetic nucleic acid can fold into an origami object without helper strands, for example, using parallel or paranemic crossover motifs. Alternatively, purely staple strands can form nucleic acid memory blocks of finite extent. The scaffolded origami or origami can be composed of deoxyribonucleotides (DNA) or ribonucleotides (RNA), or analogs or modified nucleotides thereof, including, but not limited to locked nucleic acids (LNA) and peptide nucleic acids (PNA). A scaffold or origami composed of DNA can be referred to as, for example a scaffolded DNA origami or DNA origami, etc. It will be appreciated that where compositions, methods, and systems herein are exemplified with DNA (e.g., DNA origami), other nucleic acid molecules can be substituted.

The terms "nucleic acid encapsulation", and "nucleic acid packages" are used interchangeably. They refer to the method of encapsulating nucleic acid of any length or geometry by a material to form discrete units. The encapsulating material can be of any appropriate natural or synthetic material, for example, proteins, lipids, saccharide, polysaccharides, natural polymers, synthetic polymers, or derivatives thereof. The encapsulated units are therefore in the form of gel-based beads, protein viral packages, micelles, mineralized structures, siliconized structures, polymer packaging, or any combinations thereof.

The terms "sequence-controlled polymer" or "sequence-controlled macromolecule" refer to a macro-molecule that is composed of two or more distinct monomer units sequentially arranged in a specific, non-random manner, as a polymer "chain". The arrangement of the two or more distinct monomer units constitutes a precise molecular "signature", or "code" within the polymer chain. Sequence controlled polymers can be biological polymers (i.e., biopolymers), or synthetic polymers. Exemplary sequence-controlled biopolymers include nucleic acids, polypeptides or proteins, linear or branched carbohydrate chains, or other sequence controlled polymers that encode a format of information. Exemplary sequence controlled polymers are described in Lutz, et al., *Science*, 341, 1238149 (2013).

The terms "sequence-controlled polymer memory object", or "SMO", or "block", or "memory block" are used interchangeably. They refer to an object that includes a bit stream-encoded sequence-controlled polymer, and one or more address tags or barcodes. The bit stream-encoded sequence includes a discrete piece of data, and the address tags enable selection, organization, and isolation of the memory object. In some embodiments, memory objects include bitstream-encoded sequence in the form of a continuous stretch of sequence-controlled polymer. In some embodiments, memory objects include discontinuous segments of sequence. In some embodiments, memory objects include a bitstream-encoded sequence-controlled polymer that is folded into a two or three dimensional shape. For example, sequence-controlled polymers can be folded into a nanostructure form that is the entire SMO, such as a nanostructured nucleic acid object. In some embodiments, the sequence-controlled polymer is combined with one or more additional materials to form a nanoparticle. SMOs can take any arbitrary form, for example, a linear sequence molecule, or a two-dimensional object, or a three-dimensional object. Sometimes, the memory objects are made from scaffold polymer sequence with or without staple nucleic acid sequences, or from sequence-controlled polymers of any arbitrary length/form, encapsulated within one or more encapsulating agents.

The terms "Nucleic acid memory object", or "NMO" are used interchangeably to refer to a SMO that includes nucleic acid as the bit stream encoded sequence. An NMO includes one or more segments of a nucleic acid sequence that encodes a format of information. In some embodiments, NMOs are in the form of a single-stranded nucleic acid scaffold that folds onto itself, or multiple single-stranded nucleic acid molecules that self-assemble into a programmed geometric block. NMOs can take any arbitrary form, for example, a linear nucleic acid sequence, a two-dimensional nucleic acid object or a three-dimensional nucleic acid object. Sometimes, the nucleic acid memory objects are nucleic acid objects made from scaffold nucleic acid with or without staple nucleic acid sequences, or from encapsulated nucleic acid of any arbitrary length/form, or any combinations thereof. The NMO can be composed of deoxyribonucleotides (DNA) or ribonucleotides (RNA), or analogs or modified nucleotides thereof, including, but not limited to locked nucleic acids (LNA) and peptide nucleic acids (PNA). An NMO composed of DNA can be referred to as a DNA memory object ("DMO"), etc. It will be appreciated that where compositions, methods, and systems herein are exemplified with DNA (e.g., DMOs), other nucleic acid molecules can be substituted.

The terms "splint strand" and "bridge strand" are used interchangeably to refer to a nucleic acid sequence that is complementary to two or more strands of nucleic acid sequences at distinct, non-overlapping locations. For example, a first region on a splint strand is complementary to a region on an overhang tag of a first NMO, whilst a second region on the same splint strand is complementary to a region of an overhang tag of a second NMO. The two regions of the splint strand are located so that the binding of the first NMO does not sterically hinder the binding of the second NMO. The splint or bridging strand therefore serves to bring the two NMOs into proximity with a fixed, predetermined distance.

The terms "address tag", "nucleic acid overhang", "DNA overhang tag", and "staple overhang tag" are used interchangeably to refer to nucleotides associated with SMOs that can be functionalized. In some instances, the overhang tag contains one or more nucleic acid sequences that encode metadata for the associated SMOs. In some embodiments, nucleotides are added to the staple strand of a NMO. In some embodiments, the overhang tag contains sequences designed to hybridize to other stationary-phase objects such as magnetic beads, surfaces, agarose or other polymer beads. In some instances, the overhang tag contains sequences designed to hybridize other nucleic acid sequences such as those on tags of other SMOs, or on splint strands. In other instances, the overhang contains one or more sites for conjugation to a molecule. For example, the overhang tag can be conjugated to a protein, or non-protein molecule, for example, to enable affinity-binding of the SMOs. Exemplary proteins for conjugating to overhang tags include biotin and antibodies, or antigen-binding fragments of antibodies. In some embodiments, overhang tags are designed and implemented within SMOs to enable programmable affinity and specificity between two interacting memory objects, whatever their implementation, for example, using since the principles of Boolean logic and computation.

The terms "encapsulating", "enveloping", "coating", "covering", and "shelling" are used interchangeably to refer to the process by which SMOs are completely or partially enclosed by an encapsulating agent. The term "encapsulating agent" refers to a molecular entity, such as a polymer or other matrix.

II. Methods and Systems for Sequence-Based Memory Storage

Sequence controlled polymers, such as nucleic acid molecules (e.g., DNA), represent an excellent information storage medium, having a very high potential for information density (e.g., up to $10^{24}$ bits/kg for DNA), long-term stability, and low cost of energy to maintain.

Methods for the storage of information using sequence controlled polymers formed into nanostructures have been developed. Sequence controlled polymers are folded into, or embedded within well-defined, discrete structures that serve as sequence-controlled polymer memory objects (SMO). Therefore, distinct packages of information are provided as three-dimensional structures with multiple faces that include one or more specific sequence tags. Through manipulation of SMO structures, the methods enable the partitioning, association, and re-assortment of information encoded in the polymer sequence within each SMO. Information retrieval is achieved rapidly by interpreting the sequence, structure or other physical or chemical property of the polymer. Therefore, the methods enable rapid and efficient organization and access of "memory" information stored within SMOs.

Methods for the storage of information using sequence-controlled polymers of any length, or any form have also been developed. Typically, polymers having a sequence of any desired length are packaged, encapsulated, enveloped, or encased in gel-based beads, protein viral packages, micelles, mineralized structures, siliconized structures, or polymer packaging, herein referred to as "sequence-controlled polymer memory package". In some embodiments, the synthetic polymers or biopolymers consist of a single, continuous polymer, contained within a nanoparticle. In some embodiments, the synthetic polymers or biopolymers consist or many such polymers that are combined to encode data contained within a single nanoparticle. These discrete biopolymer "packages" serve as Sequence controlled polymer Memory Objects (SMOs) and allow incorporation of one or more specific tags on the surface of the structures. Some exemplary tags include nucleic acid sequence tags, protein tags, carbohydrate tags, and any affinity tags.

In some embodiments, the sequence controlled polymer is a biopolymer, such as a nucleic acid sequence, a polypeptide amino acid sequence, a protein, a carbohydrate sequence, or combinations thereof.

1. Sequence-Controlled Polymer Memory Storage

Methods of storing memory/information polymers can include the assembly of Sequence controlled polymer Memory Objects (SMOs) including one or more bitstream encoded polymer sequences and one or more address tags. The one or more bitstream encoded polymer sequences can be present either within the particle core, or associated with one or more layers surrounding the core, for example, embedded within an encapsulating material. The indices/affinity tags are exposed and accessible. For example, the indices/affinity tags are to embedded within or otherwise attached to the external surface of the particles. The manner in which the indices/barcodes are attached to the external surface of the core particle and/or bitstream sequence can be varied according to the desired manner for pooling, sorting, organizing and accessing the information.

In some embodiments, the "shell" that is the product of "shelling" contains the encoded data.

i. Nucleic Acid Nanostructures

In exemplary embodiments, the sequence-controlled biopolymer is a nucleic acid. Methods for the storage of information using nucleic acid nanostructures have been developed. Nucleic acid nanostructures formed from single-stranded nucleic acid scaffolds of up to tens of kilobases (kb) are folded into well-defined, discrete structures that serve as nucleic acid memory objects (NMOs). Therefore, distinct packages of information are provided as three-dimensional nucleic acid structures with multiple faces that include one or more specific sequence tags. Through manipulation of NMO structures, the methods enable the partitioning, association, and re-assortment of information encoded in the single-stranded nucleic acid scaffold backbone of each NMO. Information retrieval is achieved rapidly by sequencing. Therefore, the methods enable rapid and efficient organization and access of "memory" information stored within NMOs.

Methods for the storage of information using nucleic acids of any length, or any form have also been developed. Typically, nucleic acids of any desired length are packaged, encapsulated, enveloped, or encased in gel-based beads, protein viral packages, micelles, mineralized structures, siliconized structures, or polymer packaging, herein referred to as "nucleic acid package". In some embodiments, linear nucleic acids, encoding a bitstream of information, are base-paired, double-stranded. In other embodiments, linear nucleic acids consist of a long continuous single-stranded nucleic acid polymer or many such polymers. These discrete nucleic acid packages serve as nucleic acid memory objects (NMOs) and allow incorporation of one or more specific tags on the surface of the structures. Some exemplary tags include nucleic acid sequence tags, protein tags, carbohydrate tags, and any affinity tags.

Figure 1B:
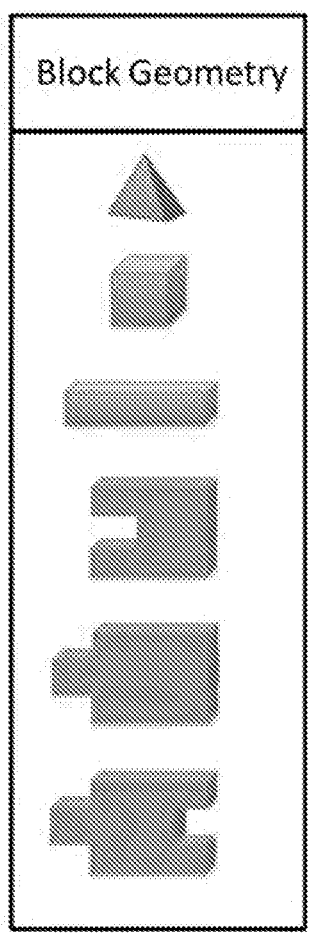
Figure 1C:
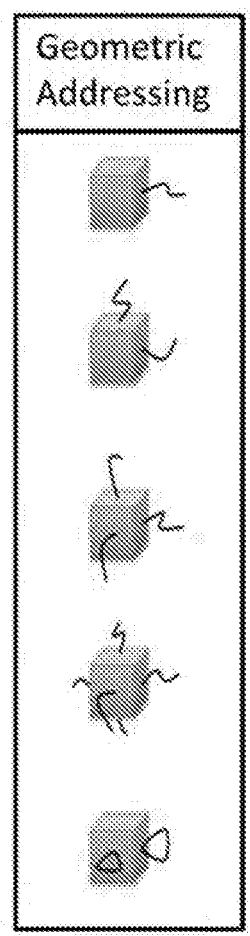

Therefore, methods for assembling bit stream sequences with bit stream information encoded in the sequence of the single-strand scaffold allows for natural spatial segregation of data into pre-defined pages or data blocks, tagging or addressing the data multiple times by functionalizing the staple strands used to fold the object, exchanging the staple strands with different overhangs to modify the address, and associating NMOs together to further spatially segregate data of interest. Data encoded on nucleic acids can be nanostructured into a diverse set of sizes and structures, and can be multiply addressed in geometrically specific positions (FIGS. 1A-1C). Nanostructured nucleic acid can fold over a wide range of scaffold sizes, from just a few hundred nucleotides up to hundreds of thousands of nucleotides in user-defined highly specific geometries that are theoretically unlimited in size. Single-stranded scaffolds, encoding a bit stream of information by conversion of digital bits to DNA bases, can be used as a scaffold that is routed through an object that is folded to a specific shape by complementary single-strand oligonucleotide staples, or alternatively by programming the single-stranded scaffold sequence to fold onto itself. These shapes can adopt any desired arbitrary form, for example, as defined by the user. In some embodiments the structures are closed tightly packed blocks. In other embodiments the structures have the form of an open wireframe mesh, for example, a polyhedral structure. In each case, the geometry of the structures can be prescribed in an arbitrary manner to suit overall memory block super-structuring and tag presentation/accessibility.

2. Sequence-Controlled Polymer Memory Access

Methods of sorting, organizing and accessing data encoded within SMOs amongst a pool of different SMOs are described. Typically, the methods select and sort SMOs based upon inter-molecular interactions between differently or equally addressed SMOs in the pool. Typically, the methods employ nucleic acid labels bound to specifically to one or more SMOs. In some embodiments each SMO contains a single tag. In other embodiments, each SMO contains more than a single tag. Therefore, in some embodiments the methods provide multiply-addressed SMOs. Multiply-addressed SMOs allow rapid selection of nucleic acid-encoded data using user-defined combinations of Boolean logics including AND, OR, and NOT logic. In some embodiments, the methods employ nucleic acid labels to physically associate distinct SMOs to one another. Therefore, in some embodiments the methods provide systems for rapid retrieval using the previous logic, and enable physical association in supra-memory blocks for networking and spatially segregating blocks of related information. In other embodiments, memory blocks are geometrically positioned in a specific location that allows for co-ordination of memory locations.

SMOS, including nanostructured NMOs, can be associated into larger super-structures based on signals to a pool of memory objects (FIGS. 2A-2D). In some embodiments a pool of SMOs contained in a solution is assembled based on specific geometries of overhang sequences in precise locations. Typically, assembly occurs through complementary sequences on overhangs, through a bridging oligonucleotide (splint strand), or through protein or chemical adducts to overhangs. The super-structured SMOs can be specifically dissociated and re-grouped by using external signals as desired by the user. Exemplary external signals used to control dissociation include changing the p, lowering the salt, increasing the temperature, application of electro-magnetic radiation, toe-hold strand displacement, complementary strand excess, or enzymatic release by restriction nucleases, nickases, helicases, resolvases, releasing using UV-sensitive linker, using CRISPR/Cas9 and guide RNAs, or any combination thereof.

Typically, the methods for assembling and storing a desired media as an SMO include one or more of the following steps:

(A) Providing a bitstream encoded sequence containing the desired media;

(B) Creating a sequence-controlled polymer memory object (SMO) including the bitstream encoded sequence; and (C) Storing the SMO including the bitstream encoded.

In some embodiments, the methods also include one or more of the following steps:

(D) Organizing or combining information within two or more SMOs;

(E) Retrieving the bit stream encoded sequence within one or more selected SMOs; and (F) Accessing the media encoded within the selected SMO.

Each of these steps is discussed in more detail, below.

A. Providing Information as a Polymer Sequence Methods for the storage, organization, access and retrieval of information as a sequence-controlled polymer, such as nucleic acid sequences, have been developed. The methods include the separation of the stored data in a protected or otherwise packaged format from overhang identifying tags that can be used for selecting or operating on the underlying stored data.

The methods include the storage, organization, access, and retrieval of information as a discrete memory object, such as a nucleic acid nanostructure. In an exemplary embodiment, information is provided in the form of a single-stranded nucleic acid that is used as a scaffolding sequence for a three-dimensional nanostructure. In some embodiments, the methods include the design of nanostructures, such as nucleic acid nanostructures, having unique structural and biochemical signatures that enable the organization and storage of information encoded within the nucleic acid forming the nanostructure. In an exemplary embodiment, the three-dimensional nanostructure is tagged with single-stranded DNA overhangs that act as unique nanostructure identifiers.

1. Information to be Stored

Methods of storing, organizing, manipulating and accessing information as physical memory "objects" can be used to store, access or record information encoded as sequence controlled polymers, such as nucleic acid sequences, or polypeptide or carbohydrate or other biopolymer sequences. The information can include any desired media in any format. In some embodiments, a desired media includes any kind of media useful to communicate information. The information or media can be obtained from any source known in the art, including exemplary print media, such as books, magazines, newspapers, etc.), televisual media, including movies, video games, televised news, cartoons, images, etc.), audible media, such as music, or radio broadcasts, cellular phone data, various kinds of software, and media available on the Internet, such as media in an html format, databases, government or private records documents, financial data or ledgers, or any other digital format, or databases of cDNA or natural DNA sequences. Internet data or other information storage data including data with properties that need to be classified automatically through machine learning or other classification strategies may also benefit from the proposed molecular memory approach. Monitoring or profiling data from flights, transportation, military, or other sources may also be of use, together with financial data, banking data, health records, patient data, and personnel-related data, and autonomous vehicle data. For example, in some embodiments, the desired media is the text of a book, or the text of one or more chapters of a book, or the text of one line of one page of a book.

2. Conversion of Data into Polymer Sequences

Typically, the methods require providing a polymer sequence that encodes a piece of desired information, such as bitstream data. Suitable polymers include sequence-controlled polymers, such as macromolecules composed of a non-random sequence of discrete monomers. An exemplary sequence-controlled polymer is a nucleic acid, such as single or double-stranded DNA, or RNA. For example, in some embodiments, a single-stranded nucleic acid sequence encoding bitstream data is input for the design of a nucleic acid nanostructure having a user-defined shape and size.

In some embodiments, a portion or portions of a digital format of information, such as an html format of information or any other digital format such as a book with text and/or images, audio, or movie data, is converted to bits, i.e. zeros and ones. In some embodiments, the information can be otherwise converted from one format (e.g., text) to other formats such as through compression by Lempel-Ziz-Markov chain algorithm (LZMA) or other methods of compression, or through encryption such as by Advanced Encryption Standard (AES) or other methods of encryption. Other formats of information that can be converted to bits are known to those of skill in the art.

Therefore, in some embodiments, the methods include converting a format of information into one or more bit sequences of a bit stream. One or more bit sequences can be converted into one or more corresponding polymer subunits. In some an exemplary embodiment, this bit sequences are converted to nucleic acid sequences. Therefore, when the desired information exists in one or more bit sequences, the methods include converting the one or more bit sequences into one or more corresponding nucleic acid sequences.

i. Sequence Controlled Polymers

Sequence controlled polymers encoding bitstream data can be biopolymers, such as DNA or polypeptides, or synthetic biopolymers, such as peptidomimetics.

A non-limiting list of suitable sequence-controlled polymers includes naturally occurring nucleic acids, non-naturally occurring nucleic acids, naturally occurring amino acids, non-naturally occurring amino acids, peptidomimetics, such as polypeptides formed from alpha peptides, beta peptides, delta peptides, gamma peptides and combinations, carbohydrates, block co-polymers, and combinations thereof. Sequence-defined unnatural polymers closely resemble biopolymers, such as polymers incorporating non-canonical amino acids. e.g., peptidomimetics, such as 0-peptides (Gellman, S H. Acc. Chem. Res., 31, 173-180 (1998)), peptide nucleic acids (PNA), peptoids or poly-N-substituted glycines (Zuckermann, et al., J. Am. Chem. Soc., 1 14, 10646-10647(1992)), Oligocarbamates (Cho, C Y et al., Science, 261, 1303-1305(1993), glycomacromolecules, Nylon-type polyamides, and vinyl copolymers.

Enzymatic and non-enzymatic synthesis of sequence-defined non-natural polymers xan be achieved through templated polymerization (reviewed in Brudno Y et al., Chem Biol.; 16(3): 265-276 (2009)). In some embodiments, higher densities of information can be achieved by increasing the chemical diversity of oligonucleotides by incorporating chemical functionalities that are not present in natural RNA and DNA into nucleotide triphosphates. In this manner, more than 100 functionalized nucleotides have been incorporated into DNA and RNA, including those containing nucleophilic groups such as amines and thiols, electrophilic groups such as acrylates and aldehydes, proton donors and acceptors such as imidazole, pyridine, and guanidinium groups, and reactive groups such as cyanoborohydride. A further exemplary polymer modification involves replacing or modifying the phosphate-ribose nucleic acid backbone. For example, modification of the 2'-hydroxyl group of RNA increases the stability of RNA and confers nuclease resistance. A number of different 2' groups have been successfully incorporated in a sequence-specific manner using polymerase enzymes including fluoro-, amino-, methoxy-, and amido-ribonucleotides. Modifications at the 4' position including azide, alkyne, and acyl moieties. The polymerase-mediated incorporation of backbones that do not contain a ribose group can also be used. In some embodiments, enzymatic polymerization of locked nucleic acid (LNA) triphosphates on DNA and RNA templates is also used. In addition to substituting the sugar group of the backbone, the phosphate group can also be modified to generate sequence-defined nonnatural polymers using polymerase enzymes. Phosphate-backbone substitutions, in which one of the non-bridging oxygen atoms is replaced, can confer greater nuclease resistance, lipophilicity, and polarizability. In a similar manner, an oxygen atom in the phosphate group can also be replaced with selenium to form phosphoroselenoate oligonucleotides.

a. Data Conversion

Methods for converting bit sequences into one or more sequence-controlled polymers are known in the art.

In exemplary embodiments, a digital file, encoded on a computer as a bit stream of 0's and 1's, is reversibly converted to a nucleic acid sequence sequence using any of the methods known in the art (FIGS. 1A-1C). In some embodiments, an oligonucleotide or DNA using a 1 bit per base encoding (A or C=0; T or G=1) to form a corresponding encoded oligonucleotide sequence, i.e. the oligonucleotide sequence corresponds to or encodes for the bit sequence. In some embodiments the choice of digital format, for example the encryption salt, and the choice of bitstream to equivalent nucleic acid sequence, for example choice of A rather than C, is optimized such that the sequence repetition and sequence self-complementarity are avoided, identified by methods known to the art.

The nucleic acid sequence generated from the bit stream data of a desired media is termed the "bit stream encoded sequence". The bit stream data encoded within the long scaffold sequence is typically "broken-up" into fragments. For example, data can be fragmented into any size range from about 100 to about 1,000,000 nucleotides, such as from about 375 to about 51,000 bases, inclusive, per object, for example, 500 bp up to 50,000 bp. In the digital storage field this is conceptually synonymous with "page" or "block". The bit stream-encoded nucleic acid sequence is synthesized by any known strategy, and is amplified or purified using a variety of known techniques (i.e., asymmetric PCR, bead-based purification and separation, cloning and purification). In some embodiments, the memory page will have identifying information as part of each sequence, including a file format signature, a sequence encoding an encryption salt, a unique identifying page number, a memory block length, and a sequence for DNA amplification.

In an exemplary embodiment, a digital file is compressed, for example, using the LZMA method, or the file is encrypted, for example, using AES128 encryption using a supplied password and salt. The compressed or encrypted bitstream of 0s and 1s is converted to a nucleic acid sequence that is chosen such that there are a minimum number of repeating or complementary sequences greater than 7 nucleotides. If such sequences exist, alternative sequences with equivalent bitstream data are chosen. The sequence is then prepended by a sequence encoding one or more of a forward primer for PCR, an identifier primer, a file-type indicating sequence, a length of the memory block stored, the size of the stored memory block, and an identifying sequence of which page of the total memory the sequence is storing. To the 3' end of the bitstream sequence, a message end signature sequence is appended. In some embodiments, the 3' end sequence also encodes slack or nonsense sequences, which are added to fill up the total needed length for the chosen geometry. The 3' end also includes a reverse identifier primer, and a reverse primer for PCR. This sequence is then synthesized. Methods to synthesize nucleic acids are known in the art. For example, in some embodiments, nucleic acids are synthesized using a GBlock from Integrated DNA Technologies, Inc., or using template-free synthesis by Molecular Assemblies, Inc., or by chip-based solid-state synthesis by Agilent, Inc., or Twist Bioscience, Inc. In some embodiments, Asymmetric polymerase chain reaction (aPCR) is used to generate the single stranded nucleic acid sequence that contains the sequence converted from the bitstream (i.e., the bit stream encoded sequence), or it may directly be encoded in and produced by living bacteria or phage.

In some embodiments, only one of the strands will be used for folding the objects, the reverse complement of the bit stream-encoding strand is used as an alternative for all applications. The bit stream data is retrievably encoded on a single-stranded long DNA scaffold. Alternatively, bit stream data is encoded within single stranded oligonucleotides that are used exclusively to fold the memory block, or within a single-stranded DNA molecule that folds onto itself without any helper strands.

In some embodiments, the methods include providing a nucleic acid sequence from a pool containing a multiplicity of similar or different sequences is provided. In some embodiments, the pool is a database of known sequences. For example, in certain embodiments a discrete "block" of information is contained within a pool of nucleic acid sequences ranging from about 100-1,000,000 bases in size, though this upper limit is theoretically unlimited. In some embodiments, the nucleic acid sequences within a pool of multiple nucleic acid sequences share one or more common sequences. When nucleic acids that are provided are selected from a pool of sequences, the selection process can be carried out manually, for example, by selection based on user-preference, or automatically.

In some embodiments, the bit stream encoded nucleic acid sequence is not the same sequence as chromosomal DNA, or mRNA, or prokaryotic DNA. For example, in some embodiments, the entire bit stream encoded sequence has less than 20% sequence identity to a naturally-occurring nucleic acid sequence, for example, less than 10% identity, or less than 5% identity, or less than 1% identity, up to 0.001% identity. Therefore, in some embodiments, bit stream encoded sequence of the desired media is not the nucleic acid sequence of an entire gene. For example, in some embodiments the bit stream encoded sequence of the desired media is not the same sequence as the open-reading frame (ORF) of a gene. In some embodiments, bit stream encoded sequence of the desired media is not the same nucleic acid sequence as a plasmid, such as a cloning vector. Therefore, in some embodiments, bit stream encoded sequence of the desired media does not include one or more sequence motifs associated with the start of transcription of a gene, such as a promoter sequence, an operator sequence, a response element, an activator, etc. In some embodiments, bit stream encoded sequence of the desired media is not a nucleic acid sequence of a viral genome, such as a single-stranded RNA or single-stranded DNA virus.

In other embodiments, the bitstream sequences are composed of the sequences of cDNAs, genes, protein sequences, protein coding open reading frames, or biological sequences that together in a pool form a database of biological sequences.

B. Constructing SMOs

Generally, the goal of generating individual SMOs is to segregate blocks of encoded information from other blocks and to separate the identifying tags from the underlying bitstream data and to allow large data-dense packages to be manipulated and selected as needed.

1. Custom Design of SMOs by Encapsulating Sequence-Controlled Polymers

Sequence-controlled polymers that encode bitstreams of information can be formed into SMOs by way of encapsulation (FIGS. 4A-4E, FIGS. 19A-19C, FIGS. 20A-20B, and FIGS. 21A-21B). For example, single- and or double-stranded DNA, or any other nucleic acid that encodes bitstreams of information can be used to generate NMOs by way of encapsulation. Sequence-controlled polymers to be encapsulated can take any arbitrary form, for example, a linear DNA sequence, a two-dimensional DNA object or a three-dimensional DNA object, a polypeptide, a protein, etc. In some forms, the linear polymers encoding a bit stream of information are nucleic acids that are base-paired and double stranded. In other forms, the linear nucleic acids consist of a long continuous single-stranded nucleic acid polymer or many such polymers. In further forms, nucleic acids encapsulated within the same particle are a mixture of linear, and non-linear nucleic acids. For example, one or more single-stranded nucleic acids and one or more scaffolded nucleic acid nanostructure can be encapsulated within the same particle.

In some forms, sequence-encoded polymers are packaged into discrete SMOs via encapsulation. Suitable encapsulating agents include gel-based beads, protein viral packages, micelles, mineralized structures, siliconized structures, or polymer packaging.

In some forms, the encapsulating agents are viral capsids or a functional part, derivative and/or analogue thereof. In some forms, the encapsulating agents are lipids forming micelles, or liposomes surrounding the nucleic acid encoding a format of information. In some forms, the encapsulating agents are natural or synthetic polymers. In some forms, the encapsulating agents are mineralized, for example, calcium phosphate mineralization of alginate beads, or polysaccharides. In other forms, the encapsulating agents are siliconized. Packaging of bitstream polymer sequences into memory blocks allows for selection and superstructuring by use of molecular identifiers, or "addresses". In addition to nucleic acid overhangs, other purification tags can be incorporated into the overhang nucleic acid sequence in any SMOs for purification (i.e. data retrieval). In some forms, the overhang contains one or more purification tags. In some forms, the overhang contains purification tags for affinity purification. In some forms, the overhang contains one or more sites for conjugation to a nucleic acid, or non-nucleic acid molecule. For example, the overhang tag can be conjugated to a protein, or non-protein molecule, for example, to enable affinity-binding of the SMOs. Exemplary proteins for conjugating to overhang tags include biotin, antibodies, or antigen-binding fragments of antibodies.

Assembly of memory objects by encapsulation, or direct assembly of sequence-encoded polymers and address tags can be carried out to produce memory objects having a range of different structures. For example, in some embodiments, memory objects include a core particle, onto which one or more sequence-encoded polymers is bound. Binding of sequence encoded polymers to a particle core can be achieved using covalent or non-covalent linkages. In some embodiments, a core molecule is coated or coupled to a molecule which is an intermediary receptor, for example, a binding site that is recognized by one or more ligands associated with the sequence encoded polymer (see FIG. 19B). Sequence-encoded polymers can be coupled or hybridized to the receptor-coated core molecule. In some embodiments, the polymer/core substructure is then coated with one or more encapsulating agents (i.e., "molecular shelling") to produce a coated polymer/core structure, which is then coupled to one or more address labels (see FIG. 19C). Binding of address labels to a coated polymer/core particle can be achieved using covalent or non-covalent linkages, or hybridization of complementary nucleic acids.

Figure 19A:
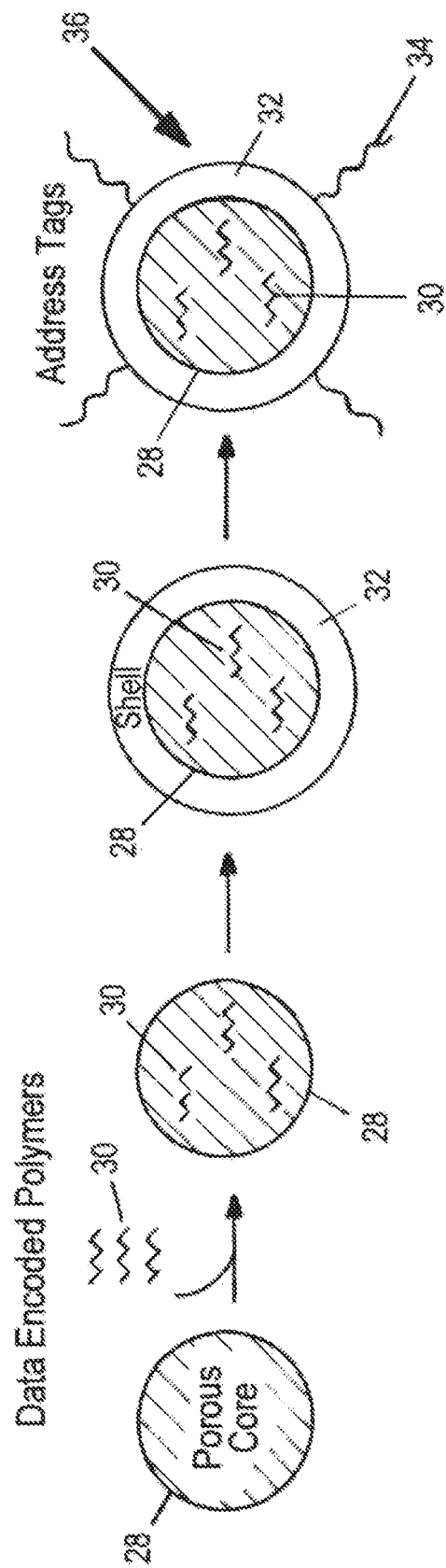

In some embodiments, assembly of a memory object includes loading or complexing one or more sequence-encoded polymers within the interior space(s) of a porous, or otherwise accessible polymer core molecule or structure (see FIG. 19A). In some embodiments, assembly of a memory object includes encapsulating, or shelling the polymer-loaded core to create an encapsulated polymer-loaded particle, which is then complexed with one or more address tags.

Figure 20A:
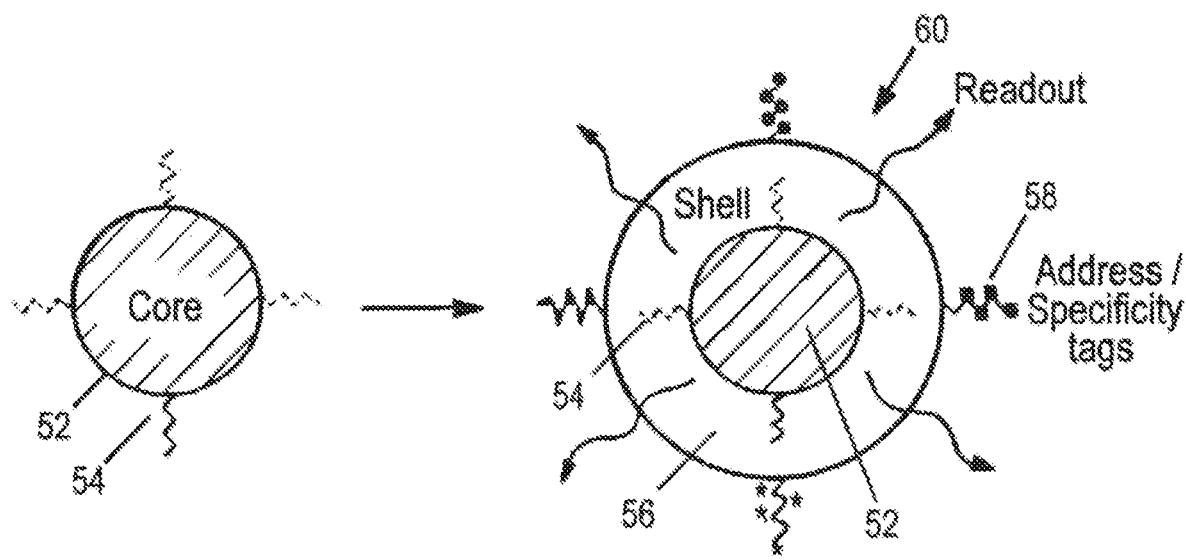
FIGS. 20A-20B are schematic illustrations depicting the molecular shelling of the memory objects including multiple data-encoded polymers and modification of the shell with affinity tags for multiplexed molecular logic operations and data selection. Data-encoded polymers (54) that are (FIG. 20A) attached to a molecular core (52) are further surrounded by a molecular shell (56) and functionalized with addressing/specificity tags (58) for multiplexed computation (60)
Figure 20B:
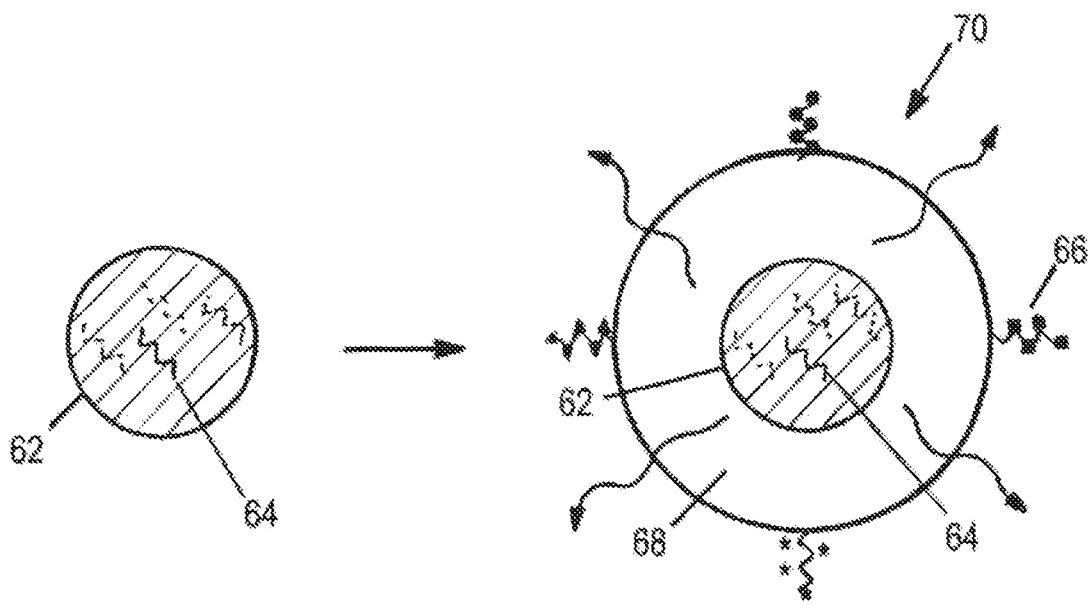

In some embodiments, memory objects include a sequence-encoded polymer, and optionally core molecules and/or encapsulating agents that are coated with multiple different types of address tags. For example, in some embodiments, memory objects are assembled to enable multiplexed molecular logic operations and data selection. For example, in some embodiments, encapsulation or molecular shelling of one or more sequence-encoded polymers, including multiple pieces of bit-stream encoded data are labelled with multiple address tags. The address tags can be attached directly to the molecular core, or absorbed by a molecular core are further surrounded by a molecular shell and functionalized with addressing/specificity tags for multiplexed computation (FIGS. 20A-20B).

Figure 21A:
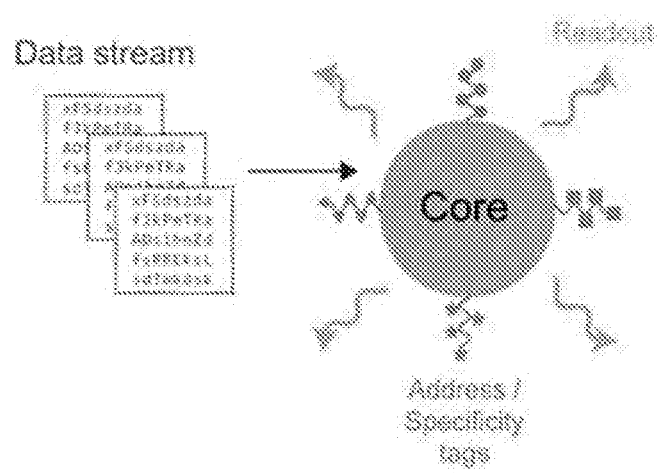
FIGS. 21A-21B are schematic illustrations depicting memory wherein data is encoded in the molecular core or shell.
Figure 21B:
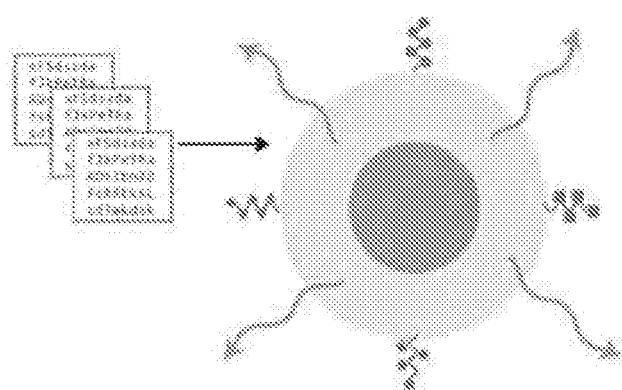

In some embodiments, memory objects include a sequence-encoded polymer, and optionally core molecules or encapsulating agents that are coated with address tags, which are then coated with a shell or core which itself produces a signal, or has another property that can be detected and measured to produce a readout. The outer "shell", or inner "core" of a memory particle can, therefore, be used to address or label the memory object. Exemplary physical or chemical properties that can be detected and measured include optical, magnetic, electric, or physical properties. Therefore, in some embodiments, the outer shell or inner core of a memory object produces a readout based on optical, magnetic, electric, or physical properties of the shell/core. FIGS. 21A-21B are schematic illustrations depicting memory wherein data is encoded in the molecular core or shell. Therefore, in some embodiments, data streams are encoded directly on a molecular core, which has a readout based on optical, magnetic, electric, or physical properties of the core. The molecular core also contains address/specificity tags for molecular logic and data retrieval operations. In some embodiments, the data stream is encoded on a molecular shell surrounding a molecular core. The shell/core has readouts based on the optical, magnetic, electric, or physical properties of the shell/core. The shell is functionalized with addressing/specificity tags for molecular logic and data retrieval operations. In some embodiments, the core structure of the particle is formed from the data encoded polymer folded into a 3D polyhedral or 2D polygon shape. For example, in some embodiments, the data encoded polymer is a nucleic acid, which is folded into a nucleic acid nanostructure having a 2D or 3D shape, which is appended with one or more address tags. Therefore, in some embodiments, the shape of a nucleic acid nanoparticle can be used to identify, sort or select the data encoded in the memory object. In some embodiments, the nucleic acid nanoparticle contains one or more additional core or encapsulating molecules that has a readout based on optical, magnetic, electric, or physical properties of the core.

i. Nucleic Acid Nanostructures

Two general approaches of constructing nucleic acid memory objects (NMOs) are described below: (1) using scaffolded nucleic acid(s) along with their associated staple strands; (2) using encapsulating material to encase a defined amount of nucleic acids (i.e., data) into a single NMO unit. Scaffolded nucleic acid nanostructures are therefore primarily made of nucleic acids, although additional non-nucleic acid component(s) can be added to the overhang sequence, for example, a protein tag for purification, or a nuclease for degradation of the bitstream-encoding nucleic acid. Encapsulated nucleic acid units can be made of any natural or synthetic materials, as long as the bitstream data is encoded on the nucleic acid sequence. In some embodiments, scaffolded nucleic acid nanostructures are also encapsulated in one or more layers of polymers for additional layers of addresses/metadata tags, and/or for long-term stability.

a. Scaffolded Nucleic Acid

The methods include assembling nucleic acid sequence containing bit-stream data into a nucleic acid nanostructure. Many known methods are available to make scaffolded nucleic acid, such as DNA origami structures. Exemplary methods include those described by Benson E et al (Benson E et al., *Nature* 523, 441-444 (2015)), Rothemund P W et al (Rothemund P W et al., *Nature.* 440, 297-302 (2006)), Douglas S M et al., (Douglas S M et al., *Nature* 459, 414-418 (2009)), Ke Y et al (Ke Y et al., Science 338: 1177 (2012)), Zhang F et al (Zhang F et al., *Nat. Nanotechnol.* 10, 779-784 (2015)), Dietz H et al (Dietz H et al., *Science,* 325, 725-730 (2009)), Liu et al (Liu et al. *Angew. Chem. Int. Ed.,* 50, pp. 264-267 (2011)), Zhao et al (Zhao et al., *Nano Lett.,* 11, pp. 2997-3002 (2011)), Woo et al (Woo et al., *Nat. Chem.* 3, pp. 620-627 (2011)), and Torring et al (Torring et al., *Chem. Soc. Rev.* 40, pp. 5636-5646 (2011)), which are incorporated here in the entirety by reference.

Typically, creating a NMO includes one or more of the steps of
(1) Designing the NMO;
(2) Labelling the NMO;
(3) Assembling the NMO; and
(4) Purifying the Assembled NMO.

b. Custom Design of Nucleic Acid Nanostructures

The nucleic acid nanostructure has a defined shape and size. Typically, one or more dimensions of the nanostructure are determined by the target sequence. The methods include designing nanostructures including the target nucleic acid sequence.

Nucleic acid nanostructures for use as NMOs can be geometrically simple, or geometrically complex, such as polyhedral three-dimensional structures of arbitrary geometry. Any methods for the manipulation, assortment or shaping of nucleic acids can be used to produce NMO nanostructures. Typically, the methods include methods for "shaping" or otherwise changing the conformation of nucleic acid, such as methods for DNA origami.

In some embodiments, nanostructures of nucleic acid target sequences are designed using methods that determine the single-stranded oligonucleotide staple sequences that can be combined with the target sequence to form a complete three-dimensional nucleic acid nanostructure of a desired form and size. Therefore, in some embodiments, the methods include the automated custom design of nucleic acid memory objects (NMOs) corresponding to a target nucleic acid sequence. For example, in some embodiments, a robust computational approach is used to generate DNA-based wireframe polyhedral structures of arbitrary scaffold sequence, symmetry and size. In particular embodiments, design of a NMO corresponding to the target nucleic acid sequence, includes providing information as geometric parameters corresponding to the desired form and dimensions of the NMO, which are used to generate the sequences of oligonucleotide "staples" that can hybridize to the target nucleic acid "scaffold" sequence to form the desired shape. Typically, the target nucleic acid is routed throughout the Eulerian circuit of the network defined by the wire-frame geometry of the nanostructure of the nanostructure.

Therefore, in some embodiments, a NMO is designed by a method including the steps of:

(1) Selecting a target structure, which may be from a predefined set of geometries, or may additionally include the steps of:
 (a) Determining the spatial coordinates of all vertices, the edge connectivities between vertices, and the faces to which vertices belong in the target structure;
 (b) Identifying the route of a single-stranded nucleic acid scaffold sequence that traces throughout the entire target structure, and
(2) Determining the nucleic acid sequence of the single-stranded nucleic acid scaffold and the nucleic acid sequence of corresponding staple strands.

A step-wise, top-down approach has been proven for generating DNA nanostructure origami objects of any regular or irregular wireframe polyhedron, with edges composed of a multiple of two number of helices (i.e., 2, 4, 6, etc.) and with edge lengths a multiple of 10.5 rounded down to the closest integer.

Typically, the route of the scaffold nucleic acid is identified by (i) Determining edges that form the spanning tree of the node-edge network (for example, using the Prim's Algorithm);
(ii) Bisecting each edge that does not form the spanning tree to form two split edges;
(iii) Determining an Eulerian circuit that passes twice along each edge of the spanning tree. The direction of the continuous scaffold sequence is reversed at the bisecting point of the node-edge network in a DX-anti-parallel crossover, and the Eulerian circuit defines the route of a single-stranded nucleic acid scaffold sequence that passes throughout the entire structure. In some embodiments, the spanning tree that is used to determine positions of the scaffold crossovers for the scaffold routing is a maximum breadth spanning tree. This is important in minimizing the number of staples per object, leading to a more stable/robust structure. Any spanning tree, however, will lead to a valid scaffold routing. In some embodiments, this method is implemented as a computational tool.

Given inputs of the geometry of the nanoparticle and the scaffold sequence (here encoding bit stream data) the program output is of the staple sequences necessary to fold the scaffold into the chosen nanoparticle. Staple strands are located at the vertices and edges of the route of the single-stranded nucleic acid scaffold sequence determined in (3). In some embodiments, these staple oligonucleotide sequences have nick positions where either a staple strand closes in on itself or where two staple strands come together, and the nick strands are positioned to be away from the center of the object ("outside").

Exemplary methods for the top-down design of nucleic acid nanostructures of arbitrary geometry are described in Venziano et al, *Science,* 352 (6293), 2016, the contents of which are incorporated by reference in entirety.

In other embodiments, the sequence of the NMO is designed manually, or using alternative computational sequence design procedures. Exemplary design strategies that can be incorporated into the methods for making and using NMOs include single-stranded tile-based DNA origami (Ke Y, et al., Science 2012); brick-like DNA origami, for example, including a single-stranded scaffold with helper strands (Rothemund, et al., and Douglas, et al.); and purely single-stranded DNA that folds onto itself in PX-origami, for example, using paranemic crossovers.

Alternative structured NMOs include bricks, bricks with holes or cavities, assembled using DNA duplexes packed on square or honeycomb lattices (Douglas et al., *Nature* 459, 414-418 (2009); Ke Y et al., Science 338: 1177 (2012)). Paranemic-crossover (PX)-origami in which the nanostructure is formed by folding a single long scaffold strand onto itself can alternatively be used, provided bait sequences are still included in a site-specific manner. Further diversity can be introduced such as using different edge types, including 6-, 8-, 10, or 12-helix bundle. Further topology such as ring structure is also useable for example a 6-helix bundle ring.

c. Assembling Nucleic Acid Nanostructures

The methods include assembly of the single-stranded nucleic acid scaffold and the corresponding staple sequences into a NMO nanostructure having the desired shape and size. In some embodiments, assembly is carried out by hybridization of the staples to the scaffold sequence. In other embodiments, NMOs include only of single-stranded DNA oligos. In further embodiments the NMOs include a single-stranded DNA molecule folded onto itself. Therefore, in some embodiments, the NMOs are assembled by DNA origami annealing reactions.

Typically, annealing can be carried out according to the specific parameters of the staple and/or scaffold sequences. For example, the oligonucleotide staples are mixed in the appropriate quantities in an appropriate reaction volume. In preferred embodiments, the staple strand mixes are added in an amount effective to maximize the yield and correct assembly of the nanostructure. For example, in some embodiments, the staple strand mixes are added in molar excess of the scaffold strand. In an exemplary embodiment, the staple strand mixes are added at a 10-20× molar excess of the scaffold strand. In some embodiments, the synthesized oligonucleotides staples with and without tag overhangs are mixed with the bit stream-encoded scaffold strand and annealed by slowly lowering the temperature (annealing) over the course of 1 to 48 hours. This process allows the staple strands to guide the folding of the scaffold into the final NMO. This is done either in separate wells and added to a pool of NMOs (as in FIGS. 3A-3D), or in a pool of oligonucleotides and scaffolds to generate a pool of NMOs. In FIGS. 3A-3D, an exemplary NMO is shown as a tetrahedron, representative of any memory block.

Figure 11:
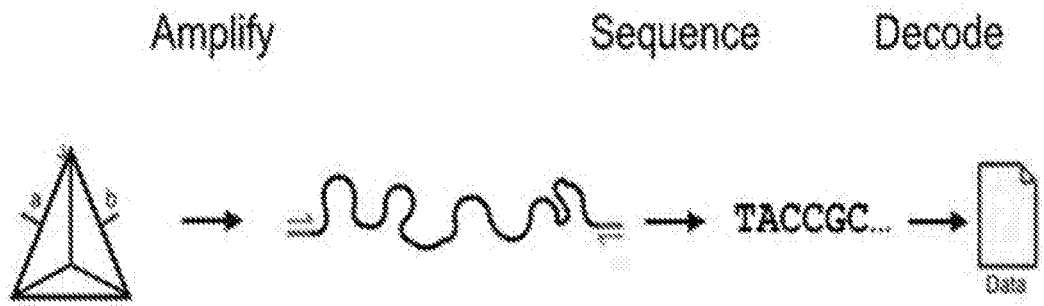
FIG. 11 is a schematic illustration depicting the workflow for the methods used to read out the selected NMO(s). Desired NMOs are first selected; NMOs are denatured, and the released single-strand nucleic acid scaffold encoding the information is amplified by virtue of master primer sequences flanking the DNA data sequence; the scaffold strand encoding the information is sequenced; and the nucleotide sequence is decoded into bit stream data. Alternatively, mass spectrometry or other analytical procedure may be used that does not require direct polymer-based sequencing to decode the information-bearing polymers, based on mass, charge, length, or other physicochemical properties. Tetrahedra are representative of any memory objects, including encapsulated nucleic acids or other information-bearing biological or synthetic polymers.
Figure 12:
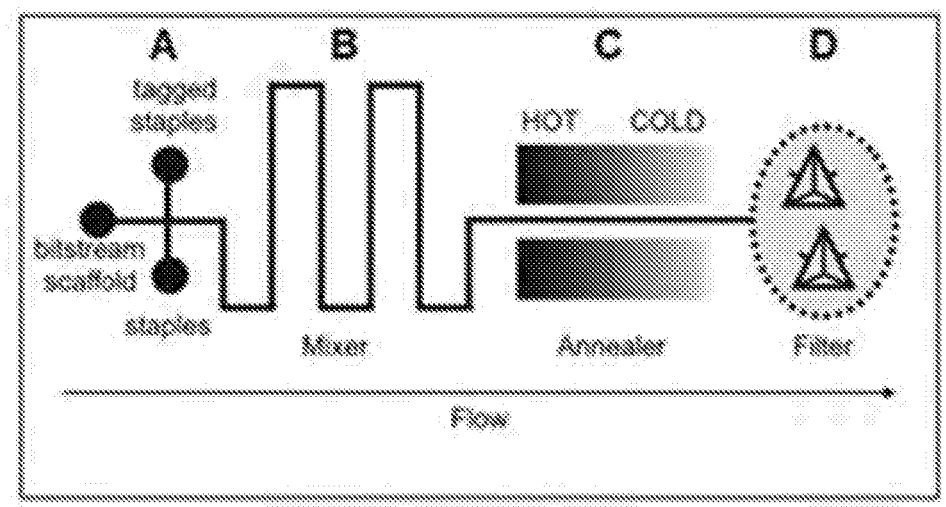
FIG. 12 is a schematic illustration depicting the workflow implemented within an exemplary microfluidic device allowing for the automated assembly and purification of a NMO. The scaffold and staples are offered as inputs to a mixing chamber ("mixer"), followed by an annealing chamber (annealer), followed by a dialysis or filtering chamber for purification of the NMO from staples (exchanger). In cases where a polymer, or other materials are used for memory encapsulation in particulate form, other upstream preparative devices may be interfaced, and bypass the need for annealing, for example.

Material usage for assembly can be minimized and assembly hastened by use of microfluidic automated assembly devices (FIGS. 11-12). For example, in certain embodiments, the oligonucleotide staples are added in one inlet, the bit stream encoded scaffold can be added in a second inlet, with the solution being mixed using methods known in the art, and the mix traveling through an annealing chamber, wherein the temperature steadily decreases over time or distance. The output port then contains the assembled NMO for further purification or storage. Similar strategies can be used based on digital droplet-based microfluidics on surfaces to mix and anneal solutions, and applied to purely single-stranded oligo-based NMOs or single-stranded scaffold origami in the absence of helper strands.

2. Labelling SMOs

One or more specific labels, such as nucleic acid sequence motifs, unique sequence identifiers, or "tags", are associated with the data encoded on a SMO. For example, in some embodiments, one or more labels is selected and then encoded into a nucleic acid sequence using a conversion method of the user's choice.

The methods include generation of unique identifying tags as metadata or keywords that are distinct and separate from the bitstream data that is otherwise protected from the metadata tags. In some embodiments, the data to be encoded will be tagged with features, for example an image of the sky being tagged as "blue" or a fragment of text being tagged as "Shakespeare", or will be tagged with cryptographic or avalanche hash values, for example through CRC32 or MD5 hashing algorithms, or will be tagged with classifying hashing algorithms, for example through perceptual, semantic, or spectral hashing, or through integers converted to sequence, or through sequence alone, or by a hash table stored separately. The bitstream data output from the classification will be converted to a nucleic acid sequence by means known to the art, including for example through base-4 conversion, or direct bit-wise to sequence. These sequences generated will then act as memory block identifiers used for sorting and otherwise manipulating the underlying memory block.

Typically, the label is a nucleic acid sequence motif, such as a barcode sequence. In some embodiments the label includes a mechanism of direct conversion, including, but not limited to, strings, integers, dates, times, events, genres, metadata, participants, hashes, or authors. In certain embodiments, tags enable direct sequence selection, with the user keeping an external library of addresses.

Nanostructuring the data blocks allows for a natural extension to spatial segregation of data based on input signals, associating related information into supra-block memory. The address space is multiplied by the number of tags in use. For example, the methods enable nucleotide addresses having 4 (k*n) bases, where n is the number of nucleotides of the address per tag and k is the number of tags. The number of tags per nanostructure can be determined by the user. Typically, each nanostructure has at least one tag, for example 2 or more tags, 3 or more tags, up to 10 tags, 20 tags, 100 tags or 1,000 tags. In some embodiments, each edge of a polyhedron has one tag, or more than one tag. In some embodiments SMOs have a number of tags that is directly proportional to the size of the polyhedron, or is dependent upon the shape of the polyhedron.

In some embodiments, when nanostructured nucleic acid objects are used as NMOs, the label is a nucleic acid sequence that is associated with a staple sequence in the form of an overhang "tag" sequence. Exemplary overhang sequences are between 4 and 60 nucleotides. In some embodiments, these overhang tag sequences are placed on the 5' end of any of the staples used to generate a wireframe DNA. In other embodiments, these overhang tag sequences are placed on the 3' end of any of the staples used to generate a wireframe DNA. In some embodiments, combinations of overhangs are employed to make logic AND/OR gates to self-assemble SMOs.

In certain embodiments parameters including the size, charge, conformation and sequence of an overhang tag is determined by one or more of user preference, location on the SMO, downstream purification techniques, or combinations. Typically, overhang tag sequences contain metadata for the scaffolded nucleic acid that carries the encoded message. For example, overhang tag sequences have address (es) for locating a particular block of data. In some embodiments, each overhang tag contains a plurality of functional elements such as addresses, as well as region(s) for hybridizing to other overhang tag sequences, or to bridging strands.

In some embodiments, the total maximal number of tags per individual NMO from 1 overhang is up to 2×(number of staples in the NMO). For example, one staple has one tag, or two tags; two staples have one tag, two tags, three tags, or four tags and so on. These tag sequences added to the staple sequences at user-defined locations, with the untagged staple strands are then synthesized individually or as a pool directly using any known methods.

In some embodiments, digital files are tagged with descriptive information relating to the tagged file. Examples of descriptive information that can be used to tag a file, include the author name(s), the date written, text relating to the content of the data, such as keywords or terms, bibliographic information, such as word or character number, page number, volume number, issue number, file format, file size, editorial or publication information and other data-base related information, such as accession or reference codes. Tagged digital files are subsequently converted to a numerical hash value, for example, using a cyclic redundancy check-16 (CRC-16) hash function. The value is then converted to a sequence by direct conversion via base 4.

In some embodiments, the tag is designed to change one or more of the interactions between the tag and the scaffold nucleic acid with which it interacts. In some embodiments the nucleic acid sequence of the tag is designed or manipulated by appending one or more sequences that alter the physical properties of the tag. Exemplary physical properties of the nucleic acid sequence that can be modified include the melting temperature or the nucleic acid. For example, in some embodiments, the melting temperature and length of the nucleic acid sequence is controlled such that ½ the total length, or more than ½ of the total length of the sequence is the hash value and the other half of the sequence is a "homo-typic" sequence including one type of nucleotide, or a randomly or non-randomly generated permutation of two types of nucleotides, or three types of nucleotide, or greater than three types of nucleotides. In an exemplary embodiment, the melting temperature and length of a DNA sequence is controlled such that ½ the length of the sequence is the hash value and the other half of the sequence is composed of nucleotides that make the GC content 50% and an 18-mer in length.

Other physical features of the tag that can be varied include the secondary structure of the nucleic acid, the ratio of one or more types of nucleotides relative to one or more of the other types of nucleotides, or the length, molecular weight, or electrochemical properties of the nucleic acid sequence.

In other embodiments, the tag sequence is a category with discrete values. Exemplary discrete values include any integer value, such as year, or collection of integer values, such as date. In other embodiments, the tag sequence encodes some continuous variable such as a shade of blue. In some embodiments the tag is partially used for key storage and partially used for value storage such that a value-key pair is stored on the tag, for example a tag with a "blue" hash also containing a "shade" hash. In some embodiments the continuous or discrete values which are nearby in information space are also nearby in sequence space with a low Hamming distance. Thus a sky-blue and light-blue would be nearer in sequence space than sky-blue and dark-blue.

In some embodiments, the pools contain different sets of tag overhangs for the same object, such that a single message is addressed with many times the number of allowed functional nick positions in the object itself. In some embodiments, the scaffold message is overlapped in sequence with multiple other scaffold messages to allow for bioinformatics assembly of long messages that extend beyond the size of the scaffold of the chosen geometries. In some embodiments, the scaffold message is overlapped in sequence with multiple other scaffold messages to allow for providing redundancy of encoded information for reduced error rates when decoded.

3. Purifying Assembled SMOs

The methods include purification of the assembled SMOs. Purification separates assembled structures from the substrates and buffers required during the assembly process. Typically, purification is carried out according to the physical characteristics of nanostructures, for example, the use of filters and/or chromatographic processes (FPLC, etc.) is carried out according to the size and shape of the nanostructures.

In an exemplary embodiment, SMOs are purified using filtration, such as by centrifugal filtration, or gravity filtration, or by diffusion such as through dialysis. In some embodiments, filtration is carried out using an Amicon Ultra-0.5 mL centrifugal filter (MWCO 100 kDa).

C. Storing Information as SMOs

The methods include storage of SMO structures. Purified SMOs can be placed into an appropriate buffer for storage, and/or subsequent structural analysis and validation.

In some embodiments the SMOs are stored in solution. In an exemplary embodiment, SMOs are stored in an aqueous solution. Suitable aqueous storage buffers include PBS, and TAE-$Mg^{2+}$. In other embodiments, SMOs are stored in oil, or an emulsion, or other hydrophobic solution. In some embodiments, the SMOs are dried or dehydrated, for example by lyophilization. In certain embodiments, the SMOs are dried and affixed to a solid support, such as filter paper.

Storage can be carried out at room temperature (i.e., 25° C.), 4° C., or below 4° C., for example, at −20° C., −40° C. or −80° C. In some embodiments, the NMOs are frozen, for example by immersion in liquid nitrogen.

In some embodiments, SMOs are stored at conditions for desired longevity. For example, the information stored in nucleic acid within NMOs can be maintained at high-fidelity for prolonged periods of time. For example, in some embodiments, NMOs are stored for up to a day, more than a day, up to a week, more than a week, up to a month, up to six months, up to a year, more than a year, up to 2 years, 3 years, 5 years, 10 years, more than 10 years, up to 20 years, or more than 20 years. Typically, very little energy required for maintenance (Zhimov, V et al., *Nature materials.* 15, 366-370 (2016)). Typically, NMOs maintain the fidelity of information encoded within the nanostructures or encapsulated for a period of time that is greater than tape-based storage having a life-time rating of 10-30 years.

Information has been encoded into DNA via an error-correction code (ECC), and DNA's information retention has been improved to an estimated ~2,000 years at 10° C. and ~2,000,000 years at −18° C. by the encapsulation of the DNA in silica (Grass, R N et al. *Angew. Chem. Int. Ed.* 54, 2552-2555 (2015)).

Figure 16:
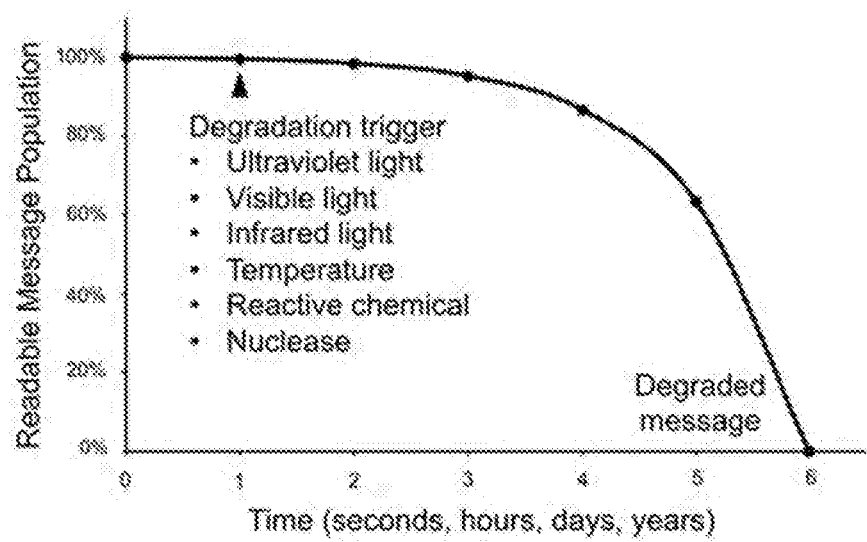
FIG. 16 is a line graph showing % Readable Message Population over Time. Degradation of NMOs is initiated at the point (▲) upon exposure to external switches such as the presence of light, heat, enzymes, chemical reactants, or air, to activate the timed degradation of the DNA, RNA, or other nucleic acid, resulting in a degraded message pool.

In some embodiments, the SMOs are preserved by chemical means, for example, encapsulation in silica ($SiO_2$). For example, in some embodiments, NMOs are preserved by chemical means, for example, encapsulation in silica (SiO2). Therefore, redundancy of data storage can be used to ensure that replicates of NMOs that may degrade over time in a random manner where nucleotide identity is lost can still be read out to reconstruct overall memory. Sequencing errors can also be eliminated by reading multiple copies of NMOs and using consensus sequence mapping. Degradation of nucleic acid memory objects upon exposure to external stimuli is depicted in FIG. 16.

D. Organizing Information as SMOs

The methods enable the organization of information contained within SMOs. Typically, organization of information is carried out by separating, associating or otherwise partitioning one piece or subset of information with or from another piece or subset. Therefore, in some embodiments, the methods organize information by association or separation of one or more SMOs. In some embodiments organization of information is achieved by physical manipulation of one or more SMOs within a pool of SMOs.

1. Association of SMO Superstructures

Figure 5A:
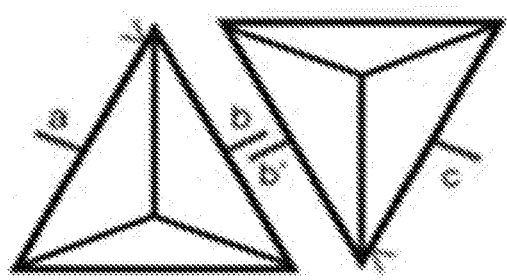
FIGS. 5A-5E are schematic illustrations of methods to superstructure nucleic acid memory objects (NMOs) to spatially segregate and associate memory blocks. Blocks can be associated by direct complementarity of their tag sequences (FIG. 5A), or by a "bridge" DNA oligonucleotide complementary to two tags (FIG. 5B), or by kissing loop (FIG. 5C), or other secondary structure interactions, including base pair end-stacking into associative memory block super-structure (FIG. 5D). The associative memory block super-structure can then be used for further selection, dissociation of the individual NMOs, or re-assortment of the data into different superstructures (FIG. 5E).
Figure 5B:
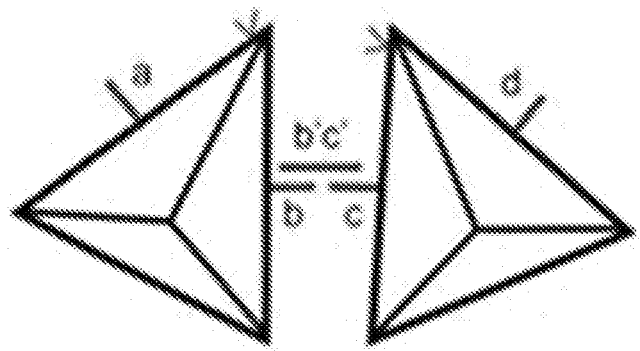
Figure 5C:
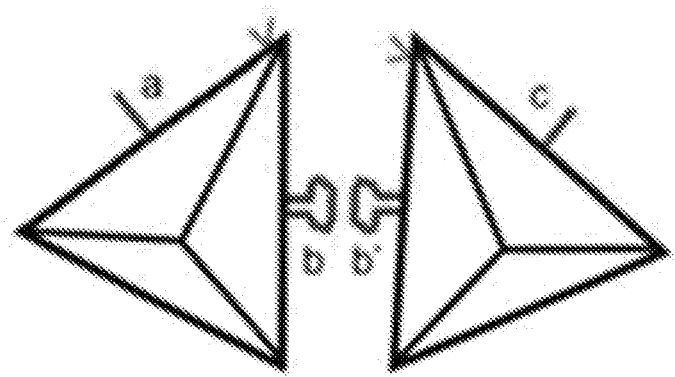
Figure 5D:
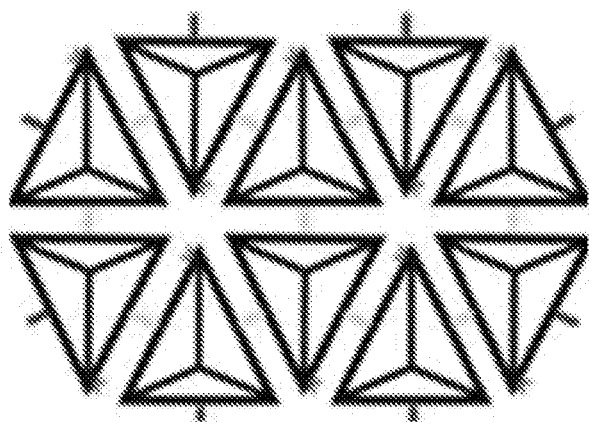
Figure 5E:
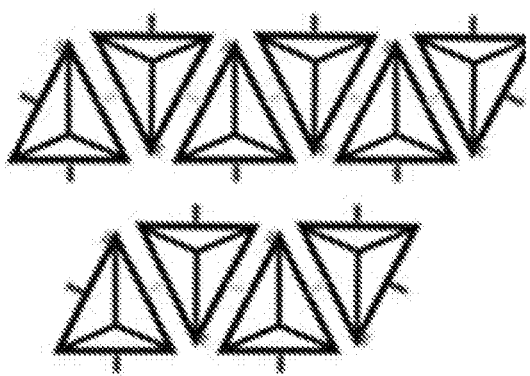

In some embodiments, the methods group or otherwise connect information by physically associating two or more SMOs to form SMO superstructures. Therefore, the methods allow association of larger sets of SMOs. An exemplary super-structure is shown in FIGS. 5D-5E, where 10 tetrahedra are associated together. In an exemplary embodiment, two tetrahedral memory objects are associated and four tetrahedral memory objects are brought together in a dimer and tetramer of SMOs in a complex, respectively, by way of two complementary overhangs per edge. Such association techniques are not limited to tetrahedra i.e. any nucleic acid memory object with a larger or smaller set of objects in the super-structure. Association through staple tags typically involves complementary tag sequences, bridging or splint sequences, kissing loops, or hybrid interconnecting staple strands, or hybrid interconnecting staple strands. In some embodiments, association occurs based on structural complementarity and non-specific base-stacking of DNA duplex ends, to form larger-scale 1D/2D/3D semi-crystalline or crystalline arrays in solution or on surfaces. Typically, buffer conditions and temperature are used to control the aggregation state of such non-specifically associated SMOs.

i. Complementary Tag Sequences

In some embodiments, SMO structures chosen for association by the user are assembled such that their tag overhangs of two objects to be associated are complementary in their nucleotide sequences. As the objects with the complementary sequences are brought together, the overhang sequences anneal and the objects will form larger superstructures. An exemplary complementary tag interaction between two NMOs is depicted in FIG. 5A.

ii. Bridging or Splint Sequences

In some embodiments, two objects are brought together with two non-complementary tag overhang sequences using a bridging or splint oligonucleotide, which contains complementary nucleotide sequence to the two overhang sequences. This allows for more dynamic associations, as the splint strand is added later after the folding of the individual objects. An exemplary bridging interaction between two NMOs is depicted in FIG. 5B.

iii. Interconnecting Staples

In further embodiments, two SMO structures are assembled using a hybrid staple that directly acts as a staple between two memory scaffolds, bringing the objects together directly during folding. In this case, the SMOs are stably bound to each other.

iv. Kissing Loops

In certain embodiments, two SMO structures are assembled using a kissing loop mechanism where complementary loops are present in two different memory objects and that directly connect two memory scaffolds, when the scaffolds are mixed together. This method brings the two objects together directly after folding. In this case, the SMOs are stably bound to each other. An exemplary kissing-loop interaction between two NMOs is depicted in FIG. 5C.

2. Dissociation of SMO Superstructures

The methods include dissociating SMO superstructures. Methods for dissociation of superstructure objects include multiple techniques, including but not limited to changing the pH, for example by increasing or decreasing pH, changing the salt concentration, increasing the temperature, toehold strand displacement, enzymatic release by restriction nucleases, nickases, helicases, resolvases, UV/light sensitive linkers, or any combinations thereof.

This has application in association of nucleic acid memory block structures, for example, in making a superstructure of all objects associated with the city Paris, by inserting sequences that would aggregate all objects tagged with the metadata addressing the city Paris. Dendritic DNA stars including arrays of single-stranded overhangs physically associated at a central covalent linkage or on a bead may also be used to aggregate SMOs in this manner.

Additionally, re-assortment of super-molecular memory structures is also feasible using nanostructured data. SMOs, which have been associated via splint strands, complementary tag overhangs, or kissing loop interactions can be dissociated via a variety of techniques, including by changing the pH, lowering the salt, increasing the temperature, toe-hold strand displacement, enzymatic release by restriction nucleases, nickases, helicases, resolvases, or any combination thereof. Re-association of the SMOs then allows for a modification in the structures of the controlled aggregates.

In the context of associative memory, this allows the re-association of new combinations of data-encoded scaffolds. For example, this allows for disassembling the superstructure representing SMOs displaying metadata tags encoding the city Paris and re-associating a new SMO superstructure associating all NMOs displaying metadata tags encoding for paintings from the late $19^{th}$ century.

Figure 2:
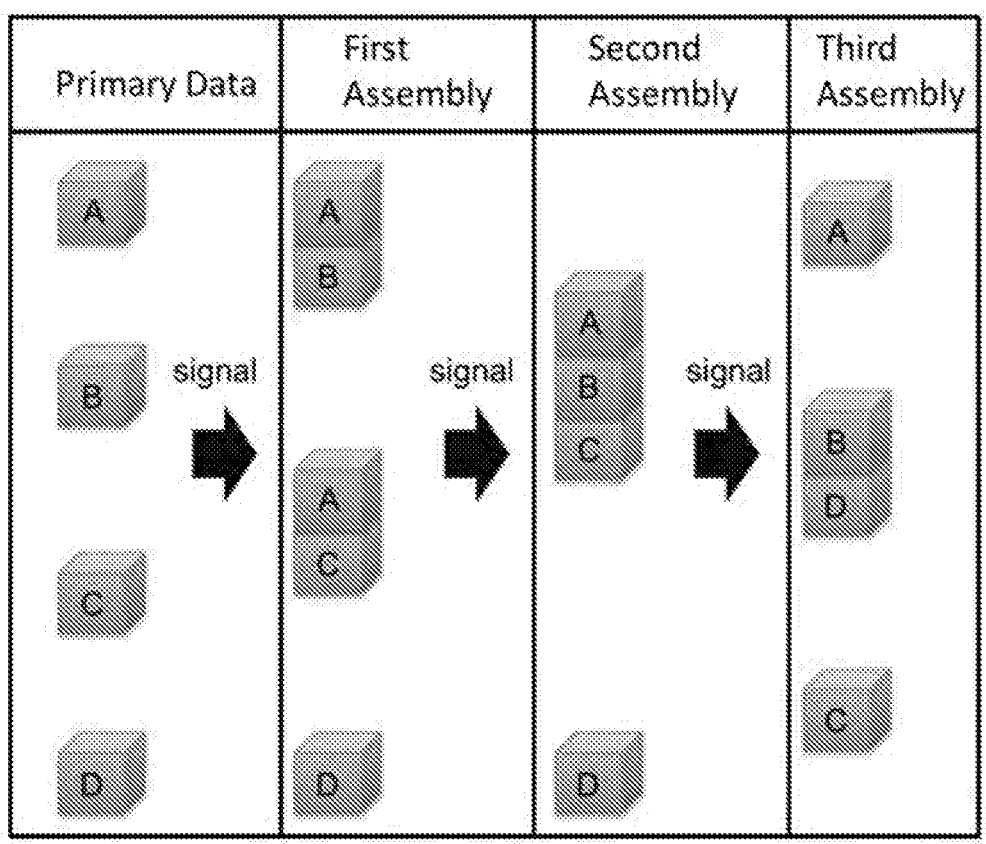
FIG. 2 is a schematic chart depicting the associative nanostructured data framework amongst a pool of biopolymer memory objects. Generalized memory objects, shown as cubes, (A-D) can be maintained as separate, individual structures, or assembled into larger superstructures of AB, AC and D, respectively through a first signal event. The cuboid structures can reassemble and be re-sorted into differently-organized larger super-structures of ABC through a second signaling event and can be re-assorted to change geometries to expose internal blocks through a third signaling event, respectively, which may also be actuated extrinsically/externally through microfluidic or other mixing mediated by fluidics or solid-state manipulation of sub-pools of SMOs.
Figure 3A:
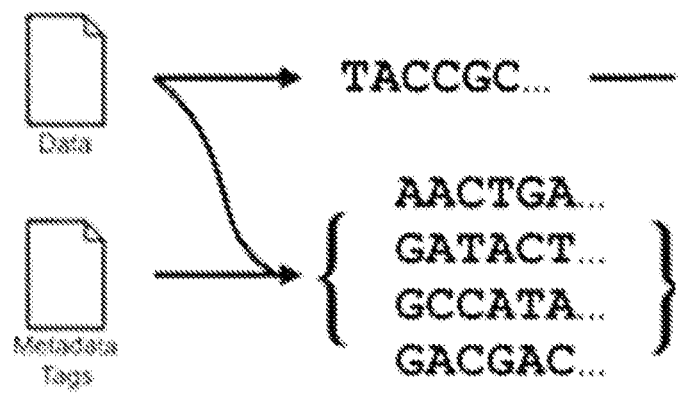
FIGS. 3A-3D are schematic diagrams, each depicted a step in the method to assemble a pool of nucleic acid memory objects. Information in the form of bit stream data is encoded into the scaffold strand of a nucleic acid origami object, which may be synthesized using template-free DNA synthesis using, for example, TDT polymerase, solid-state DNA synthesis, bacterial synthesis, PCR-based enzymatic synthesis, or another approach, multiply addressed with metadata tag overhang sequences on the staple strands (FIG. 3A); the scaffold strand including two address tags (*) at each end of the scaffold, and the staple strands where overhang tags are used to encode multiple addresses (A and B) to the folded data are synthesized (FIG. 3B); the single-strand nucleic acid memory scaffold is combined with the staple oligonucleotides to fold into a DNA origami object (FIG. 3C); and adding the folded, multiply addressed DNA origami object to a memory pool (FIG. 3D).
Figure 3B:
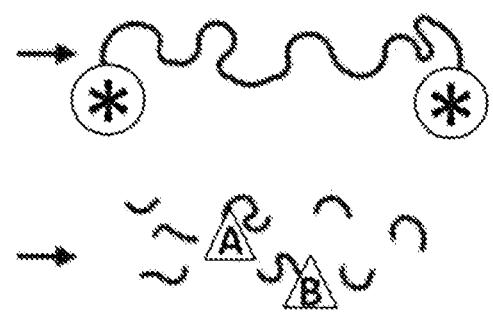
Figure 3C:
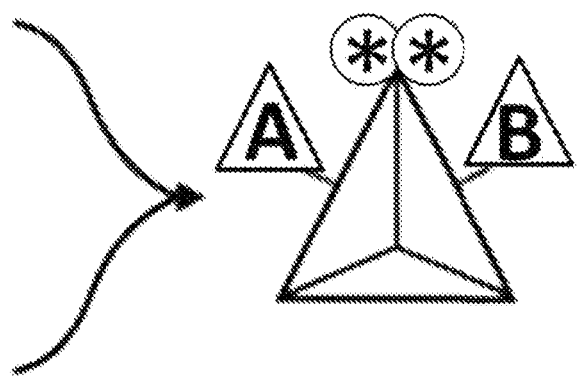
Figure 3D:
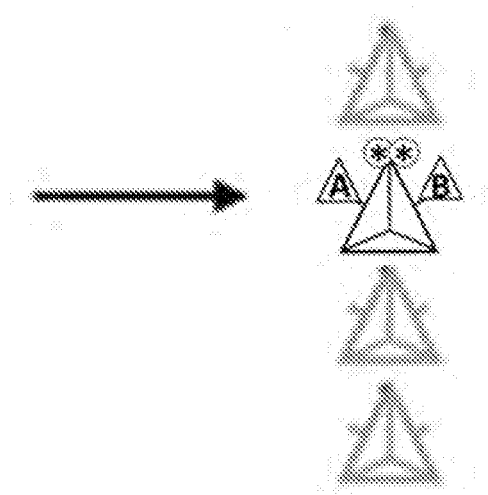
Figure 4A:
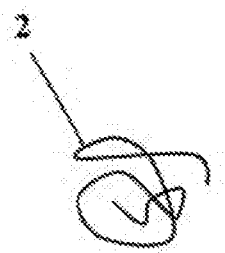
FIGS. 4A-4D are schematic illustrations of encapsulated sequence-controlled biopolymers of any arbitrary forms into discrete SMOs for data storage.
Figure 4B:
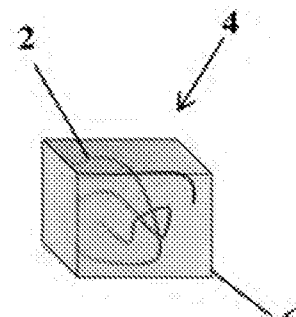
Figure 4C:
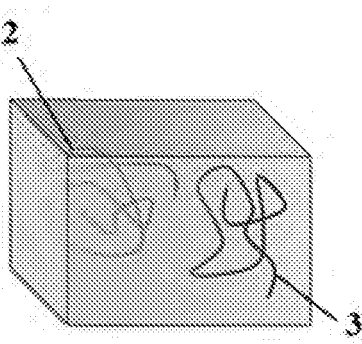
Figure 4D:
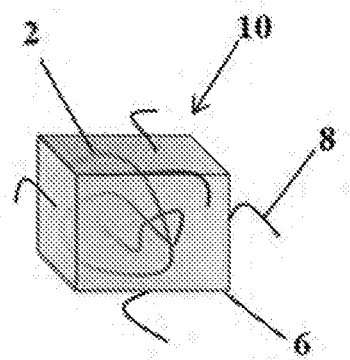
Figure 4E:
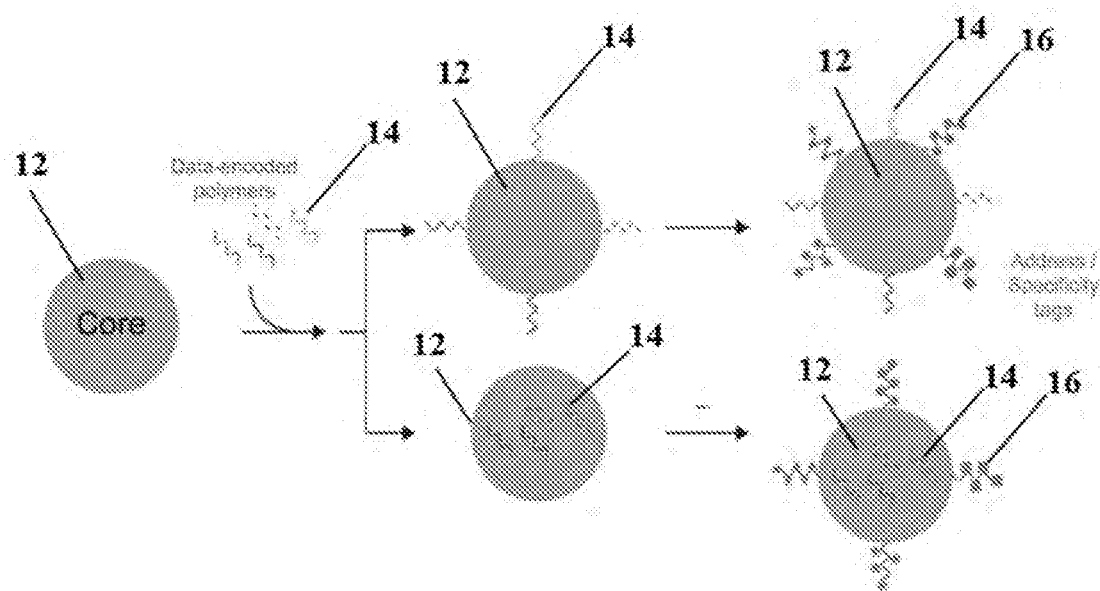
FIG. 4E is a schematic illustration showing the workflow of multiplexed attachment and encapsulation of data-encoded polymers and modification of the molecular core (12) for downstream molecular logic operations and data selection. Multiple data-encoded polymers are attached or absorbed by a molecular core. The molecular core is then functionalized with addressing/specificity tags (14, and 16) for multiplexed computation and selection.

Tags from functionalized staple strands can be modified with a new addressing system, and the nanostructures can be refolded with the new set of tagged staples. This allows for a dynamic addressing system that does not require resynthesis of all the data. Dissociation can also be used to move SMOs from one to another memory block based on extrinsic signals or cues described above. A schematic chart depicting the associative nanostructured data framework amongst a pool of nucleic acid memory objects is depicted in FIG. 2.

E. Access of Information within SMOs

The methods include the step of accessing information. For example, information stored within nucleic acid sequences can be accessed by selecting one or more SMOs, for example, selecting a subset of SMOs or SMO superstructures. Typically, selection of SMOs is carried out using methods that selectively capture or remove one or more sequence tags associated with one or more SMOs or subsets of SMOs. Therefore, the methods provide random access of information. In some embodiments, selection is based on SMO geometry, SMO size, SMO sequence, or combinations. In some embodiments, nucleic acids and/or nucleic acid structures are bound to a solid phase for use in the selection and purification of SMOs. For example, nucleic acids can be hybridized onto beads, such as AMPure XL SPRI beads.

1. Selection of Geometry

Figure 7A:
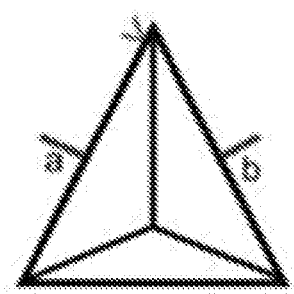
Figure 7B:
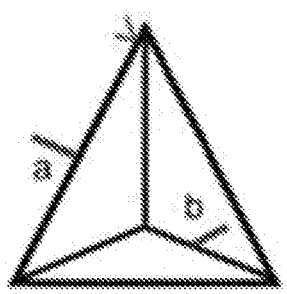

In some embodiments, when nanostructured nucleic acid objects are used as NMOs, the methods include selecting the geometry of nanostructured NMOs. Therefore, in some embodiments, NMOs having certain geometry are selected from a pool of NMOs having different geometry (FIGS. 7A-7C). For example, in some embodiments, geometry determines the position and/or accessibility of one or more tags. In some embodiments, NMOs having defined tags in certain orientations on the NMO allow for the specific capture of only those NMOs. In certain embodiments, one or more NMOs or NMO superstructures with specific sequences and geometries satisfying the specific geometric placement of complementary strands on a complementary or receiving object are selected.

For example, as shown in FIGS. 7A-7C, a nanostructured NMO displaying sequences a and b on different geometric locations, such as on two edges. These sequences would be complementary to two overhangs on a complementary geometric DNA nanostructure, displaying a' and b' at positions ideal for selecting the NMO. Typically, the larger nanostructure is part of a surface, or bound to a surface or solid support by chemical, hybridization, or protein interaction. In this way, a NMO is specifically selected based not just on sequence of the tagged overhang, but also on the geometry of the NMO.

2. Selection Based on Sequence

The methods include selecting one or more components of the sequence of SMOs. A mechanism to selectively retrieve only desired portions of a pool (i.e., random access) is implemented by selecting the desired sequence tag of the SMOs of interest. Methods of capturing desired DNA sequence tag are known in the art.

In some embodiments, the desired sequence tags are captured via nucleic acid hybridization, in which "bait" sequences are used to select the tag regions of the SMOs. In some embodiments, the "bait' sequences are nucleotide sequences complementary to the desired sequence tag. In some embodiments, the "bait" sequences are DNA molecules. In other embodiments, the "bait" sequences are RNA molecules. In some embodiments, hybridization capture is an in-solution approach. In preferred embodiments, hybridization capture is a solid-phase (immobilized) approach.

Figure 6:
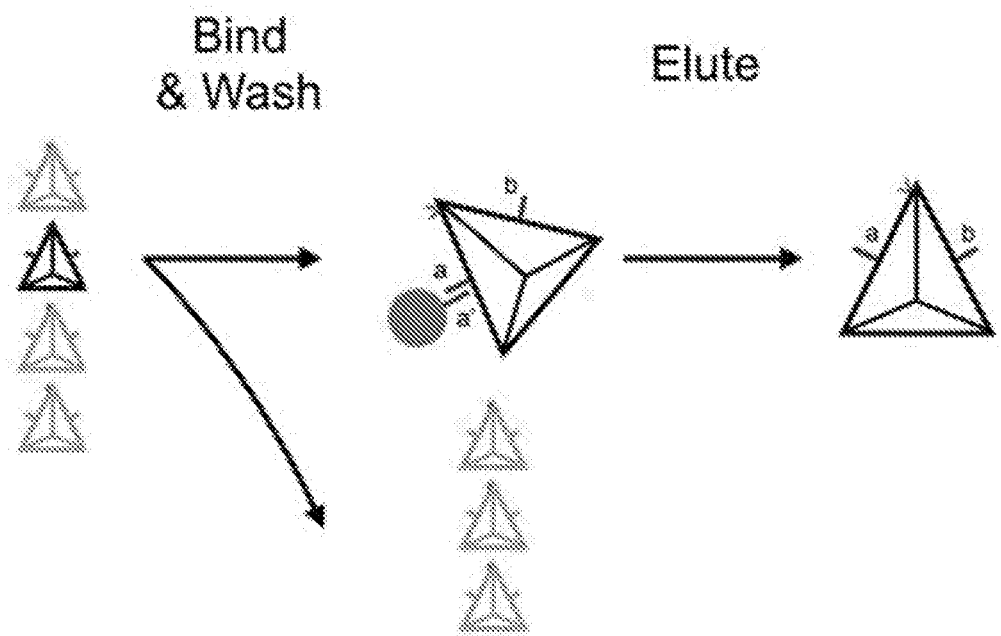
FIG. 6 is a schematic illustration providing a general overview of methods used to retrieve specific NMOs using complementary single-strand DNA sequences to the tags of the specified block(s). An exemplary method of NMO purification and selection is based on stationary phase complementary strands to tag(s) on the NMO: a single NMO is captured from a pool of NMOs captured using a capture support with sequences complementary to a (a'), and; captured NMOs having overhang sequence a are then released from the support. Tetrahedra are representative of any NMOs including encapsulated nucleic acids.

An exemplary method of retrieving NMO structures of interest from a pool of NMOs in shown in FIGS. 6A-6C. For example, in some embodiments a target SMO in a pool of SMOs, can be retrieved using tag overhang sequences. In some embodiments, short single-strand oligonucleotides are synthesized with sequences complementary to the sequence of the tag overhang of the SMOs of interest using known methods. Typically, these sequences are synthesized with a label that is used for capturing these oligonucleotides on a stationary phase, for example a biotin 5' label. The labeled nucleotides are attached to a stationary support. Exemplary stationary supports include streptavidin-coated beads or streptavidin-coated surfaces. When biotin is used, biotin-oligonucleotide captured nucleic acids are incubated with the streptavidin support to allow for binding (hereafter "capture support"). Unbound sequences are removed from the sample, for example, by washing.

In an exemplary embodiment, specific capture is achieved by annealing the SMO complementary overhang sequence to the capture support. Methods for specific capture of SMOs by annealing include mixing a pool of SMOs with a capture support and annealing, for example, by incubating at temperatures from 4° C. up to the melting temperature of the SMOs (approximately 55° C.), and then cooling to allow annealing. Washing the unbound fraction from the capture support using mild conditions to remove nonspecific binding, such as with slight heating or lowered salt allows for specific capture and subsequent purification of the SMO of interest away from the pool.

In some embodiments, the capture sequence is complementary to the key-value pair such that a target address and corresponding memory block will be captured and those target addresses with low Hamming distances and corresponding memory blocks will also be captured. Methods of increasing or decreasing this background of memory blocks with similar address tags can be, for example but not limited to, based on temperature, pH, capture time, changes in salt. For example, an NMO with a "sky-blue" tag could be captured by a selection on a "light-blue" complementary capture support given the specific conditions of the capture.

The captured SMO is released from the capture support by any mechanisms known in the art. The non-limiting methods include changing the pH, lowering the salt, increasing the temperature, toe-hold strand displacement, enzymatic release by restriction nucleases, nickases, helicases, resolvases, or any combination thereof.

In further embodiments, splint strands can be generated that would include part of the sequence complementary to the tag overhang being targeted, and a second part of the splint sequence complementary to the capture sequence on the capture support, as described for superstructures in FIGS. 5A-5C.

In some embodiments, capturing of SMOs takes place in minimized volumes, for example, using microfluidic devices in bulk or on surfaces. In some embodiments a microfluidic device includes of a surface or bead-based oligonucleotide support, with sequences complementary to the tag overhang sequences of one or more SMOs. The inlet port provides an aliquot of the pooled memory objects, leading to a stationary phase capture region, allowing for segregation of capture and flow-through objects. In this manner, flow-through (i.e., unbound) objects are captured separately from the captured objects (FIGS. 13A-13G). Prior to manipulation and capture SMOs are stored in a dry state in paper, or other solid support matrix, for long-term storage prior to rehydration and manipulation prior to sequencing-based readout.

3. Re-Organization and Re-Addressing of SMOs

SMOs constructed and tagged according to the described methods can be organized by addition of one or more functionalized groups associated with the tags within the staple strands forming the SMOs. In some embodiments, the selection criteria used to access and purify one or more pieces or subsets of information is altered or modified to enable the re-characterization of one or more pieces of information within a pool of SMOs. For example, re-characterization of data can be achieved by modification of the functionalization groups associated with the staples. Modification of the staple sequences can be carried out by biochemical means, for example, by association or dissociation of one or more functionalization groups with the same staple tag. Therefore, in some embodiments, information is characterized or re-characterized using nucleic acid nanostructures in the folded-state. In other embodiments, information is characterized or re-characterized by refolding the nanostructures with the new set of tagged staples. When nanostructures are refolded using one or more differently-tagged staples, new sequences can be incorporated into the staples associated with the nanostructures. Therefore, the methods include "re-addressing" the nanostructures using functionalized staple strands can be modified with a new addressing system. The methods allow for a dynamic addressing system that does not require re-synthesis of all the data.

4. Boolean Logic

In some embodiments, Boolean logic of AND, OR, and NOT are applied to SMOs using the tag overhang sequences as described in FIGS. 8A-8E, FIGS. 9A-9C, and FIGS. 10A-10B. These logic applications are complementary. In some embodiments, these logic applications are applied once. In other embodiments, the same logic application is applied multiple times, for example, 2, 3, 4, 5, 6, 7, 8, 9, 10, 20, 30, 40, 50, 100 times, or more than 100 times. An exemplary multiple applications of the same logic is a AND b AND c AND d AND e, etc. In some embodiments, these logic applications are used in any desired order or combination to generate large sets of logical computations. An exemplary combination is a AND b, followed by NOT c. In some embodiments, these logic applications are used in any desired order or combination multiple times, for example, 2, 3, 4, 5, 6, 7, 8, 9, 10, 20, 30, 40, 50, 100 times, or more than 100 times.

i. AND Logic

In some embodiments, AND logic is applied in the selection and purification of a SMO with two or more overhang tag sequences (FIGS. 8A-8E). A SMO or set of SMOs is purified from a pool of SMOs when the targeted SMOs are able to be separated using AND logic. For example, a SMO or set of SMOs of interest are purified in multiple rounds, first using a capture support specific to one overhang of interest (i.e., capturing all SMOs with the overhang sequence a). Unbound NMOs are then washed away, leaving the bound SMOs attached to the capture support, as described in FIGS. 5A-5C. Captured SMOs are then released from the support by changing the pH, lowering the salt, increasing the temperature, toe-hold strand displacement, enzymatic release by restriction nucleases, nickases, helicases, resolvases, UV/light sensitive linkers, or any combination thereof. The pool of released SMOs from this first round are then applied to a second round of purification with a second, distinct set of capture sequences bound to a support. The SMOs are then captured on the second capture support with a distinct capture sequence (i.e., capturing all SMOs of the released pool having an overhang sequence b) and unbound SMOs are washed away as in FIGS. 6A-6C. The bound SMO(s) are then released from the support by changing the pH, lowering the salt, increasing the temperature, toe-hold strand displacement, enzymatic release by restriction nucleases, nickases, helicases, resolvases, with UV or light, or any combination thereof. This yields SMOs with overhang sequences a AND b. In some embodiments, this AND logic purification process is repeated twice, three times, four times, five time, up to ten times, or more than ten times. In some embodiments, this AND logic purification process is repeated for the number of instances of tags on a given object (2×(number of staples)).

Exemplary Procedures for Sorting of NMOs Using AND Logic

In exemplary embodiments, AND logic could be demonstrated using the limited pool described in Example 1. For example, Tags appended to nucleic acid memory objects can include encoded information describing one or more pieces of information or text that can be used to identify a memory object, such as the title, genre, speaker, other active participants, the author, the date it was first performed, a random message index, the act and scene of the play, any important context, etc.

In exemplary embodiments, data encoded by each group of memory objects includes: (1) specific text from a specific literary work, and (2) metadata used for tagging for the specific text, which is common to each group and different for each of the three groups of memory objects. Exemplary literary works include "HAMLET", "WAITING FOR GODOT" and "THE CRUCIBLE". Further levels of selectivity amongst each pool can be demonstrated, for example, by selecting a specific subset from the same pool. In exemplary embodiments, the pool of NMOs including text from "HAMLET" includes two or more differently-labelled pieces of data, for example, two separate pieces of text from the same play. In some exemplary embodiments, data corresponding to text from each of two acts of the play HAMLET are distinguished as "ACT 1" and "ACT 2" by different labels.

In exemplary embodiments, AND logic is demonstrated by selecting a specific piece of text from a pool of the 3 different groups of NMOs. First, messages from one group of objects will be purified by a bead-based selection using a biotinylated oligonucleotide complementary to the sequence encoding the "HAMLET" address. This biotinylated capture oligonucleotide will be affixed to streptavidin-coated magnet beads. The NMO pool will be selected on by annealing the objects to the functionalized beads under appropriate conditions for optimal annealing. Exemplary conditions include a temperature of 30-37° C. with bead-oligonucleotides in excess in a buffer including 1×TAE+100 mM NaCl, +12 mM $MgCl_2$ under constant agitation for 30 minutes and then pelleted by a magnet and subsequently washed. The objects purified with the "HAMLET" address will be released via toehold strand displacement, where an oligonucleotide sequence complementary to the "HAMLET" capture sequence with an additional 8-nucleotide complementary toehold will be incubated with the bound beads at 37° C. for 2 hours. The released objects, competed off by the toehold strand will be added to a second set of functionalized beads with overhang oligonucleotides with a sequence complementary to the "ACT 1" address. Again the pool of NMOs having the HAMLET address will be selected on, for example, by incubation for 30 minutes at 30-37° C. under constant agitation. The magnetic beads will be pelleted with a magnet and washed. The bound fraction of the bead will be isolated using appropriate conditions for isolation. Exemplary conditions for release include exposure to 10 µL of $H_2O$, at a temperature of 65° C. Each step of the selection will typically be collected, and amplified by PCR using the universal primers surrounding the bitstream sequence. This experiment will additionally be carried out in the presence of a large background of M13 genomic DNA scaffolded tetrahedra with random 16-mer overhangs to simulate the same selection in the context of a very large memory pool. In this way, the use of AND logic for memory selection from a pool could be demonstrated.

ii. OR logic

In some embodiments, OR logic is applied in the selection and purification of a SMOSMO with one or more overhang tag sequences (FIGS. 9A-9C). A SMO or set of SMOs is purified from a pool of SMOs when the targeted SMOs are able to be separated using OR logic. For example, a SMO or set of SMOs of interest are purified in a single round, where instead of a single capture sequence being attached to the capture support, a set of sequences are bound to the support. The capture support then has the ability to capture multiple tag overhangs in the same round of purification. Therefore, a SMO can be captured that would contain an overhang of sequence a OR an overhang of sequence e using capture support with sequences complementary to a (a') and e (e'), with SMOs containing neither being washed off the capture support. The bound SMO(s) are then released from the support by changing the pH, lowering the salt, increasing the temperature, toe-hold strand displacement, enzymatic cleavage by restriction nucleases, or any combinations thereof.

Experimental procedures for sorting and selecting data from a pool of SMOs using OR logic are demonstrated in the Examples.

iii. NOT Logic

In some embodiments, NOT logic is applied in the selection and purification of a SMO with one or more overhang tag sequences (FIGS. 10A-10B). A SMO or set of SMO structures is purified from a pool of SMOs when the targeted SMOs are able to be separated using NOT logic. For example, a SMO or set of SMO structures of interest are purified in a single round, where instead of the target SMO(s) being bound to the capture support, the target SMO(s) are those washed off from the capture support. Therefore, SMOs having overhang tag sequences of a are captured on the capture support using the capture sequence complementary to a (a'). Unbound objects from this capture support are all those objects which do not contain the a overhang, thus NOT a.

Experimental procedures for sorting and selecting data from a pool of SMOs using NOT logic are demonstrated in the Examples F. Retrieval of Information from SMOs The methods include retrieving the information stored within sequence controlled polymers. For example, in some embodiments the methods include retrieving the information stored within nucleic acid nanostructures. Retrieval of information typically includes reversal of bit stream data, for encoding the information.

1. Retrieval of Information from NMOs

In some embodiments, Methods for dissociation of NMOs to their single-strand components include denaturation of NMOs. NMOs can be denatured by changes in pH, or temperature. In an exemplary embodiment, NMOs are denatured by melting (FIGS. 11A-11D). The released single-strand scaffold containing the message is purified and amplified by virtue of master primer sequences flanking the DNA data sequence. The nucleotide sequence is read out via any known sequencing methods. In some embodiments, PCR is used to amplify the final selected message. In some embodiments PCR is achieved using a set of primers that are specific to the NMO of interest. In some embodiments, PCR is carried out using a set of "master primers" that are tested to be orthogonal to encoded data. Typically, the data pool is specifically selected to narrow down the pool to only messages that satisfy the user request. When all data within NMOs is surrounded by a single set of master primers, only a single PCR reaction is necessary in the workflow. In some embodiments, barcode sequences are generated on the surface of nanoparticle and/or microparticle scaffolds using a DNA synthesizer. The barcode-modified scaffolds capture the requested encoded NMOs from the data pool. In some embodiments, barcode sequences generated on chip arrays capture the requested NMOs from the data pool for retrieval and subsequent PCR amplification.

i. Sequencing Methods

Any known DNA sequencing methods can be used. In some embodiments, the nucleotide sequence is read out via sequencing methods including Sanger sequencing (Sanger F et al., *Proc. Natl. Acad. Sci. U.S.A.* 74 (12): 5463-7(1977)).

In some embodiments, the nucleotide sequence is read out via Maxam & Gilbert sequencing (Maxam A M et al., *Proc. Nat. Acad. Sci. USA* 74, 560-564 (1977)), or any other chemical methods. In other embodiments, sequencing is done by PYROSEQUENCING™. In further embodiments, the nucleotide sequence is read out by single molecule sequencing using exonuclease.

In some embodiments, sequencing is done by next generation sequencing. Some exemplary technologies include ILLUMINA®, Roche 454 sequencing, Ion torrent: Proton/PGM sequencing, SOLiD sequencing. Some exemplary commercial providers of next generation sequencing are Pacific Biosciences, ILLUMINA®, Oxford Nanopore Technologies.

ii. Error Correction

DNA synthesis generates errors in the nucleotide sequence, with the error rates on the order of 1% per nucleotide. Furthermore, long-term storage of NMOs will compromise data integrity. In some embodiments, errors are reduced by increase data redundancy, by means of storing NMOs, or by replicating NMOs periodically.

iii. Data Redundancy

A key aspect of DNA storage is to devise appropriate encoding schemes that tolerate errors by adding redundancy.

In some embodiments, errors are tolerated by adding redundancy at the stage of encoding. For example, the encoding proposed by Goldman et al., where the input DNA nucleotides are split into overlapping segments to provide multiple fold redundancy for each segment (Goldman N et al., *Nature*, 494:77-80 (2013)). In some embodiments, the encoding redundancy is incorporated as proposed by Bornholt J et al. (Bornholt, J et al., 21*th ACM International Conference on Architectural Support for Programming Languages and Operating Systems.* (2016)) using exclusive, or of two payloads to form a third strand.

iv. Replication of NMOs

For long term storage of data via NMOs, deamination is the highest source of information loss in ancient DNA and has the lowest energy barrier (Zhimov V et al., *Nat Mater.* 23; 15(4):366-70 (2016)). To combat information loss in practical memory or storage systems, error-correction codes are widely used (Kim C et al., *IEEE Trans. Consum. Electron.* 61, 206-214 (2015)). Fortunately, nucleic acid is easy to copy, which decreases the ECC overhead and thus makes error correction a primary factor for data integrity. In some embodiments, nucleic acid encoding format of information are replicated into numerous physical copies of itself with high fidelity and low cost.

2. Retrieval of Information from Other Sequence Controlled Polymers

The methods include retrieving the information stored within sequence controlled polymers. For example, in some embodiments the methods include retrieving the information stored within nucleic acid nanostructures. Retrieval of information typically includes reversal of bit stream data, for encoding the information.

III. Databases

The methods can include the creation of databases. Databases can be used to enable or assist subsequent analysis of the same or different samples. For example, databases can be used to assist the analysis of one or more similar types of samples having similar or different levels of heterogeneity.

For example, the methods can include a step of developing a database of information. Information databases can be initiated, developed and maintained in any format known in the art, for example by employing a data system such as a digital computer. In some embodiments, information for populating a database can be accumulated by including a sufficiently large number of samples, for example, by creating a library of nucleic acid nanostructures, and/or encapsulated nucleic acid units.

Typically, databases include at least two different pieces of data, such as bit stream data, or sequences or tags that can be used to identify bit stream data, or subsets of bit stream data. In some embodiments, databases include nucleic acid sequences and/or corresponding barcodes for each piece of bit stream data in a pool, for example, corresponding to each SMO in a pool, or a library of SMOs. In some embodiments, each tag or barcode in a database corresponds to one or more sequences or other features of bit stream data. Databases populated with binary bar codes depicting the sequences of different bit stream data, such as a library of SMOs produced according to the described methods, can be developed. Databases can store binary sequence bar codes corresponding to one or more different pools of bit stream data. For example, a database can include of tens, hundreds, thousands of more non-contiguous nucleic acid sequences.

A. Applications

1. Databases

In some embodiments, the generation of a multiply-addressed pool of SMOs will act as a database for the long-term storage of information. Multiple indices on data will allow for highly specific extraction of information based on search terms used. Therefore, in some embodiments, the database is searched using search terms based on nucleic acid sequences complementary to the tags of the SMOs. In some embodiments, the tag is encoded by a known scheme direct to text, dates, or other type castings such that no external database is needed to extract SMOs based on metadata. This direct conversion of metadata to capture sequence can be used to mine data contained within the solution-database of SMOs as deeply as allowed by the number of allowed tags on a given geometry. Common database queries can be used against a system, such as PUT, GET, Delete, AND, and OR. Thus a database of all book titles, encoded on the bit stream-encoded scaffold sequence of a SMO can be indexed with call number, author, length, genre, publication date. The book title can then be extracted out after the pool of all book titles has been probed to capture the specific title of interest. Using associative memory would allow for specific aggregation of records satisfying a set of criteria generated by the user and when given the proper signal. For example, all book titles by Shakespeare could be associated to a superstructure. Examples of usefulness include, but are not limited to, library records (card catalogs), hospital records, insurance records, financial records, experimental catalogs, court proceedings, and government documentation.

2. Filesystems

In some embodiments, the methods include the creation of a filesystem. The Filesystem can be used to enable or assist in the assortment of documents that can be extracted as needed based on tag metadata. In this application, the data stored as bit stream encoded scaffold sequences act as computer files, wherein the decoded data contains digital files that can be converted and decoded on a computer as required by the user. Metadata tags of the encoded data are used as a method for filing the information in a geometric position, associating the computer files based on metadata, and extracting the information as required. As such, data stored within the SMO pool operates as a filesystem commonly used in a computer operating system.

3. Message Passing

In some embodiments, the methods include the creation of a system to exchange information in a "hidden" method. For example, in some embodiments, a NMO is hidden in a pool of junk DNA, and the hidden message can be extracted using a set of keys complementary to the addresses of the object containing the correct message.

B. Programmed Destruction of SMOs

Methods of programmed destruction of bitstream-encoding SMOs are also described. In some forms, this destruction is triggered by an external stimulus to allow on-demand destruction of the SMOs (FIGS. 16A-16C).

In some embodiments, the methods include programmed destruction of bitstream-encoding NMOs based on one or more properties of the nucleic acids within the NMO. Triggerable elements that induce degradation of the NMOs can cause degradation to any components of the NMOs, for example, the length of nucleic acids encoding data, any associated overhang sequences, or any encapsulating agents. Therefore, in some embodiments, programmed destruction of data-encoding NMOs involves the destruction of nucleic acid encoding data, and/or destruction of any addresses/tags to scramble data so that the original data is no longer retrievable. In further embodiments, external switches, such as the presence of light, heat, enzymes, chemical reactants, or air, activate the timed degradation of the DNA, resulting in an unreadable message pool in a specific amount of time.

1. Triggerable Elements

Triggerable elements can be sensitive to triggering stimuli such as light, heat or ultrasound. Exemplary heat triggerable elements include gold particles, which are sensitive to near-infrared (NIR) light.

i. UV, Visible and Near-Infrared (NIR) Light Triggering

In some embodiments, a tube, marble-like object, paper-like object, or other container store DNA-encoded messages that are sensitive to an external signal that will degrade in a specific segment of time after the introduction of the signal. Ibis signal can be of types such as ultraviolet, visible, or infrared light, chemical reactive species, nucleic acids that are unstable, or nucleases that are otherwise inhibited except under such environmental signals. For example, one external signal is the use of ultraviolet light interacting with a photo-cleavable tag on either the primers used to read the message, the message itself, or the single-strand tags used for message selection. Thus, upon exposing the message DNA sequence to light, the NMO becomes unusable in a specified reaction time. FIG. 16 depicts how these signals can initiate the process of message degradation that ultimately leads to the inability to extract the message from the DNA.

ii. Ultrasound

In some embodiments the triggerable elements are elements that cause degradation of SMOs in response to ultrasound. In some embodiments the triggerable elements include Ultrasound Cleavable Bonds. See, for example, Xuan, Langmuir, 2012, 28, 16463-16468 Ultrasound cleavable bonds can also be introduced for chemical disruption of the NMOs.

iii. Enzymatic Triggering

In some embodiments the triggerable elements are elements that cause degradation of SMOs in response to ultrasound. For example, nucleases that are otherwise inhibited except under certain external environmental signals can be used as a trigger for degradation of the nucleic acids within NMOs. In one particular embodiment, aptazymes that degrade the nucleic acid at programmed sites on programmed time-scales with programmed environmental cues (pH, salt, etc.). Other enzymes that are specific for degrading the encapsulating agents, such as proteases, lipase, or any glycoside hydrolase enzymes are also suitable. In some embodiments, proteases are used as a trigger for degradation of the encoded polypeptides encapsulated within SMOs.

iv. Magnetic Triggering

In some embodiments, the triggerable elements are elements that cause structural changes, and/or degradation in response to magnetic triggering. Exemplary triggerable elements that cause degradation of SMOs in response to magnetic triggering are super-paramagnetic nanoparticles.

IV. Compositions

The compositions described below include materials, compounds, and components that can be used for the disclosed methods. Various exemplary combinations, subsets, interactions, groups, etc. of these materials are described in more detail above. However, it will be appreciated that each of the other various individual and collective combinations and permutations of these compounds that are not described in detail are nonetheless specifically contemplated and disclosed herein. For example, if one or more nucleic acid nanostructures are described and a number of substitutions of one or more of the structural or sequence parameters are discussed, each and every combination and permutation of the structural or sequence parameters possible are specifically contemplated unless specifically indicated to the contrary.

These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Nucleic Acid Memory Objects

1. Nucleic Acid Samples

Nucleic acids for use in the described methods can be synthesized or natural nucleic acids. In some embodiments, the nucleic acid sequences including the format of information are not naturally occurring nucleic acid sequences. In some embodiments, the nucleic acid sequences including the format of information are synthetic nucleic acid sequences. In some embodiments, the nucleic acid nanostructures are not genomic nucleic acid of a virus. In some embodiments, the nucleic acid nanostructures are virus-like particles.

In some embodiments, bit-stream data is encoded within a nucleic acid scaffold sequence, for example a synthesized nucleic acid sequence. Typically, bit-stream data is "broken-up" into any size, for example, up to 1,000,000 nucleotides, or more than 1,000,000 nucleotides, for example, fragments can range from 500-50,000 bases, or more, per scaffold (in the digital storage field this is conceptually synonymous with "page" or "block"). The bit stream-encoded DNA sequence is synthesized by any known strategy, and is amplified or purified using a variety of known techniques (i.e., asymmetric PCR, bead-based purification and separation).

Although only one of the strands will be used for folding the objects, the reverse complement of the bit stream-encoding strand is used as an alternative for all applications. The bit stream data is retrievably encoded on a single-stranded long DNA scaffold.

Numerous other sources of nucleic acid samples are known or can be developed and any can be used with the described method. In some embodiments, nucleic acids used in the described methods are naturally occurring nucleic acids. Examples of suitable nucleic acid samples for use with in the described methods include genomic samples, RNA samples, cDNA samples, nucleic acid libraries (including cDNA and genomic libraries), whole cell samples, environmental samples, culture samples, tissue samples, bodily fluids, and biopsy samples.

Nucleic acid fragments are segments of larger nucleic molecules. Nucleic acid fragments, as used in the described method, generally refer to nucleic acid molecules that have been cleaved. A nucleic acid sample that has been incubated with a nucleic acid cleaving reagent is referred to as a digested sample. A nucleic acid sample that has been digested using a restriction enzyme is referred to as a digested sample.

In certain embodiments, the nucleic acid sample is a fragment or part of genomic DNA, such as human genomic DNA. Human genomic DNA is available from multiple commercial sources (e.g., Coriell #NA23248). Therefore, nucleic acid samples can be genomic DNA, such as human genomic DNA, or any digested or cleaved sample thereof. Generally, an amount of nucleic acids between 375 bp and 1,000,000 bp is used per nucleic acid nanostructure.

2. Nucleic Acid Nanostructures

The basic technique for creating nucleic acid (e.g., DNA) origami of various shapes involves folding a long single stranded polynucleotide, referred to as a "scaffold strand", into a desired shape or structure using a number of small "staple strands" as glue to hold the scaffold in place. Several variants of geometries can be used for construction of NMOs. For example, in some embodiments. NMOs from purely shorter single stranded staples can be assembled, or NMOs including purely a single stranded scaffold folded onto itself, any of which can take on diverse geometries/architectures including wireframe or bricklike objects.

i. Staple Strands

The number of staple strands will depend upon the size of the scaffold strand and the complexity of the shape or structure. For example, for relatively short scaffold strands (e.g., about 50 to 1,500 base in length) and/or simple structures the number of staple strands are small (e.g., about 5, 10, 50 or more). For longer scaffold strands (e.g., greater than 1,500 bases) and/or more complex structures, the number of staple strands are several hundred to thousands (e.g., 50, 100, 300, 600, 1,000 or more helper strands).

Typically, Staple strands include between 10 and 600 nucleotides, for example, 14-600 nucleotides.

In scaffolded DNA origami, a long single-stranded DNA is associated with complementary short single-stranded oligonucleotides that bring two distant sequence-space parts of the long strand together to fold into a defined shape Historically, folding of DNA nanostructures has relied on tedious per-object design without generalized scaffold sequence choice.

A robust computational-experimental approach is used to generate DNA-based wireframe polyhedral structures of arbitrary scaffold sequence, symmetry and size. These DNA origami objects have several important properties that render them useful for DNA-based memory storage, including 1) arbitrary numbers of faces or edges that are programmed to present outward-facing ssDNA tags that act as either handles to physically associate with other memory blocks or act as barcodes on these memory blocks for bead-based or other physical extraction/purification; 2) they do not associate or aggregate with one another non-specifically because they have an absence of free duplex ends, unlike brick-like origami; 3) they are porous so that small molecules and other singles-stranded nucleic acids as well as restriction enzymes and polymerases may diffusive through these memory blocks even when assembled into supramolecular memory blocks; 4) they remain stably folded under moderate ionic strengths; 5) unlike unpaired single-stranded DNA that associates non-specifically with itself and other strands of partial base complementarity, these DNA nanostructure origami sequester single-stranded DNA in a tightly associated, stable form that renders biochemical purification and transport practical.

ii. Geometric Shapes of NMOs

NMOs are nucleic acid assemblies of any arbitrary geometric shapes. NMOs can be of two-dimensional shapes, for example plates, or any other 2-D shape of arbitrary sizes and shapes. In some embodiments, the NMOs are simple DX-tiles, with two DNA duplexes connected by staples. DNA double crossover (DX) motifs are examples of small tiles (~4 nm×~16 nm) that have been programmed to produce 2D crystals (Winfree E et al. *Nature.* 394:539-544(1998)); often these tiles contain pattern-forming features when more than a single tile constitutes the crystallographic repeat. In some embodiments, NMOs are 2-D crystalline arrays by parallel double helical domains with sticky ends on each connection site (Winfree E et al., Nature. 6; 394(6693):539-44 (1998)). In some embodiments, NMOs are 2-D crystalline arrays by parallel double helical domains, held together by crossovers (Rothemund P W K et al., *PLoS Biol.* 2:2041-2053 (2004)). In some embodiments, NMOs are 2-D crystalline arrays by an origami tile whose helix axes propagate in orthogonal directions (Yan H et al., *Science.* 301:1882-1884 (2003)).

In some embodiments, NMOs are wireframe nucleic acid (e.g., DNA) assemblies of a uniform polyhedron that has regular polygons as faces and is isogonal. In some embodiments, NMOs are wireframe nucleic acid (e.g., DNA) assemblies of an irregular polyhedron that has unequal polygons as faces. In some embodiments, NMOs are wireframe nucleic acid assemblies of a convex polyhedron. In some further embodiments, NMOs are wireframe nucleic acid assemblies of a concave polyhedron. In some further embodiments, NMOs are brick-like square or honeycomb lattices of nucleic acid duplexes in cubes, rods, ribbons or other rectilinear geometries. The corrugated ends of these structures are used to form complementary shapes that can self-assemble via non-specific base-stacking. Some exemplary superstructures of NMOs include Platonic, Archimedean, Johnson, Catalan, and other polyhedral. In some embodiments, Platonic polyhedron are with multiple faces, for example, 4 face (tetrahedron), 6 faces (cube or hexahedron), 8 face (octahedron), 12 faces (dodecahedron), 20 faces (icosahedron). In some embodiments, NMOs are toroidal polyhedra and other geometries with holes. In some embodiments, NMOs are wireframe nucleic acid assemblies of any arbitrary geometric shapes. In some embodiments, NMOs are wireframe nucleic acid assemblies of non-spherical topologies. Some exemplary topologies include nested cube, nested octahedron, torus, and double torus.

In preferred embodiments, a set of tags to be associated with the data encoded on a NMO are selected and then encoded into a nucleic acid (DNA or locked nucleic acids or RNA, etc.) sequence using a conversion method of the user's choice. In some embodiments, it also includes a mechanism of direct conversion from, including but not limited to strings, integers, dates, events, genres, metadata, participants, or authors. In further embodiments, this additionally includes direct sequence selection, with the user keeping an external library of addresses.

B. Sequence Controlled Polymer Encapsulation

Single- and/or double-stranded DNA or any other sequence-controlled polymer that encodes bitstreams of information can be encapsulated to generate SMOs. These encapsulated acid sequence-controlled polymer units can also have one or more surface-based molecular identifier (address tag) for physical selection and manipulation. Typically, the encapsulated acid sequence-controlled polymer units are designed for reversibility and recovery of the intact encapsulated sequence-controlled polymer, thus allowing for sequencing and readout of the encoded message.

The encapsulated memory objects typically include one or more address tags coupled to the exterior of the coating. Address tags can be are directly or indirectly. Address tag-functionalized particles are pooled and stored for downstream data selection and information retrieval. In further embodiments, the address tags on the surface of the SMO-containing particles are used to select data using a complementary strand to isolate the desired data from the data pool. The encoded SMOs are released from the particles using a buffered oxide etch. The SMOs can then be processed for decoding and readout.

1. Sequence Controlled Polymers to be Encapsulated

Sequence controlled polymers encoded with bitstream information to be encapsulated can take any arbitrary form, for example, a linear or branched polypeptide, a linear or branched carbohydrate, a protein, a glycosylated polypeptide, a linear nucleic acid sequence, a two-dimensional nucleic acid object or a three-dimensional nucleic acid object. In some forms, the linear nucleic acids encoding a bit stream of information are base-paired double stranded. In other forms, the linear nucleic acids consist of a long continuous single-stranded nucleic acid polymer or many such polymers. In further forms, sequence controlled polymers encapsulated within the same particle are a mixture of any one or more of a linear, or non-linear single or double stranded nucleic acid molecule, a polypeptide, a carbohydrate, a protein, or a glycosylated polypeptide. For example, is some embodiments, one or more single-stranded nucleic acids and one or more scaffolded nucleic acid nanostructure are encapsulated within the same particle.

2. Encapsulating Agents

In some forms, sequence controlled polymers are packaged into discrete SMOs via encapsulation. For example, in some forms, nucleic acids are packaged into discrete NMOs via encapsulation. Suitable encapsulating agents include gel-based beads, protein viral packages, micelles, mineralized structures, siliconized structures, or polymer packaging.

In some forms, the encapsulating agents are viral capsids or a functional part, derivative and/or analogue thereof. In some forms, the NMOs are viral like particles, with nucleic acid content enveloped by protein content on the surface. Viral capsids can be derived from retroviruses, human papilloma viruses, M13 viruses, adeno viruses adeno-associated viruses, for example, adenovirus 16. In preferred forms, viral capsids used for encapsulating NMOs do not interfere with the overhang tags i.e. overhang tags are accessible for purification purposes.

In some forms, the encapsulating agents are lipids forming micelles, or liposomes surrounding the nucleic acid encoding a format of information. In some forms, micelles, or liposomes are formed from one or more lipids, which can be neutral, anionic, or cationic at physiologic pH. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but not limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids in the micelles, or the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylanmonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl] cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), $diC_{14}$-amidine, N-ferf-butyl-N'-tetradecyl-3-tetradecylamino-propionamide, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxylethyl)-2,3-dioleoyloxy-1,4-butanedianmonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids may be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine).

In some forms, the encapsulating agents are natural or synthetic polymers. Representative natural polymers are proteins, such as zein, serum albumin, gelatin, collagen, and polysaccharides, such as cellulose, dextrans, and alginic acid. Representative synthetic polymers include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, poly[lactide-co-glycolide], polyanhydrides, polyorthoesters blends and copolymers thereof. Specific examples of these polymers include cellulose acetate, cellulose propionate, cellulose acetate butyrate, cellulose acetate phthalate, carboxymethyl cellulose, cellulose triacetate, cellulose sulphate, poly(methyl methacrylate), (poly(ethyl methacrylate), poly(butyl methacrylate), Poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), poly(vinyl acetate), poly (vinyl chloride), polystyrene and polyvinylpyrrolidone, polyurethane, polylactides, poly(butyric acid), poly(valeric acid), poly[lactide-co-glycolide], polyanhydrides, polyorthoesters, poly(fumaric acid), and poly(maleic acid).

In some forms, the encapsulating agents are mineralized, for example, calcium phosphate mineralization of alginate beads, or polysaccharides. In other forms, the encapsulating agents are siliconized. In one embodiment, the nucleic acid is packaged in a mineral structure, but has on its surface single-stranded nucleic acids that act as the address used for association with other NMOs, or selection by Boolean logic.

In some embodiments, the encapsulating agents are metal oxide particles. Exemplary metal oxide encapsulating agents include silicon dioxide ($SiO_2$) and titanium dioxide ($TiO_2$), that can be mesoporous, compact, or structured. In some embodiments, the DNA is adsorbed on the surface of a modified metal oxide particle then coated with polyelectrolytes, for example poly(diallyldimethylammonium chloride), poly(acrylamide-co-diallyldimethylammonium chloride), and poly(allylamine hydrochloride).

3. Address Tags

In some embodiments, the address tags are directly synthesized on to the encapsulated memory objects. In one embodiment, NMO-containing particles that have surfaces coated with 9-O-dimethoxytrityl (DMT)-triethylene glycol, 1-[(2-cyanoethyl)-(N, N-diisopropyl)]-phosphoramidite. When a DNA synthesizer is used to generate the address tags, modified silica particles are used directly as the solid-phase support for the DNA synthesizer. In other embodiments, the address tags are synthesized separately and are attached on the surface of NMO-containing particles using chemical conjugation. For example, in some embodiments, address tags are conjugated to memory objects wherein the conjugation chemistry involves biotin-avidin recognition pairs, N-hydroxysuccinimide (NHS) coupling, 1-ethyl-3-(3-dimethylaminopropyl) carbodiimide (EDC) coupling, succinimidyl 4-(N-maleimidomethyl)cyclohexane-1-carboxylate (SMCC)-mediated coupling, sulfo-SMCC coupling, copper-catalyzed azide-alkyne cycloaddition (CuAAC), strain-promoted azide-alkyne cycloaddition (SPAAC), or combinations of these. Address tag-functionalized particles are pooled and stored for downstream data selection and information retrieval. In further embodiments, the address tags on the surface of the SMO-containing silica particles are used to select data using a complementary strand to isolate the desired data from the data pool. The encoded SMOs are released from the silica particles using a buffered oxide etch. The SMOs can then be processed for decoding and readout.

In addition to nucleic acid overhangs, other purification tags can be incorporated into the overhang nucleic acid sequence in any SMOs for purification (i.e. data retrieval). In some forms, the overhang contains one or more purification tags. In some forms, the overhang contains purification tags for affinity purification. In some forms, the overhang contains one or more sites for conjugation to a nucleic acid, no non-nucleic acid molecule. For example, the overhang tag can be conjugated to a protein, or non-protein molecule, for example, to enable affinity-binding of the SMOs. Exemplary proteins for conjugating to overhang tags include biotin and antibodies, or antigen-binding fragments of antibodies. Purification of antibody-tagged SMOs can be achieved, for example, via interactions with antigens, and or protein A, G, A/G or L.

Further exemplary affinity tags are peptides, nucleic acids, lipids, saccharides, or polysaccharides. For example, overhang contains saccharides such as mannose molecules, then mannose-binding lectin can be used for selectively retrieve mannose-containing SMOs, and vice versa. Other overhang tags allow further interaction with other affinity tags, for example, any specific interaction with magnetic particles allows purification by magnetic interactions.

4. Nucleic Acid Overhang Tag

In some embodiments, the overhang sequences are between 4 and 60 nucleotides, depending on user preference and downstream purification techniques. In preferred embodiments, the overhang sequences are between 4 and 25 nucleotides. In some embodiments, the overhang sequences contain 4, 5, 6, 7, 8, 9, 10, 11, 12, 13, 14, 15, 16, 17, 18, 19, 20, 21, 22, 23, 24, 25, 30, 35, 40, 45, 50 nucleotides in length.

In some embodiments, these overhang tag sequences are placed on the 5' end of any of the staples used to generate a wireframe nucleic acid. In other embodiments, these overhang tag sequences are placed on the 3' end of any of the staples used to generate a wireframe nucleic acid.

In some embodiments, overhang tag sequences contain metadata for the scaffolded nucleic acid, or the encapsulated nucleic acid that carries the encoded message. For example, overhang tag sequences have address(es) for locating a particular block of data. In some further embodiments, each overhang tag contains a plurality of functional elements such as addresses, as well as region(s) for hybridizing to other overhang tag sequences, or to bridging strands. These tag sequences added to the staple sequences at user-defined locations, with the untagged staple strands are then synthesized individually or as a pool directly using any known methods.

5. Modifications to Nucleotides

In some embodiments, one or more of the nucleotides of the address tags of SMOs are modified nucleotides. In some embodiments, one or more of the nucleotides of the scaffolded nucleic acid sequences of NMOs are modified nucleotides. In some embodiments, the nucleotides of the encapsulated nucleic acid sequences of NMOs are modified. In some embodiments, one or more of the nucleotides of the nucleic acid staple sequences are modified nucleotides. In some embodiments, the nucleotides of the DNA tag sequences are modified for further diversification of addresses associated with SMOs. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2-2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and (acp3)w, 2,6-diaminopurine. Nucleic acid molecules may also be modified at the base moiety (e.g. at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

Locked nucleic acid (LNA) is a family of conformationally locked nucleotide analogues which, amongst other benefits, imposes truly unprecedented affinity and very high nuclease resistance to DNA and RNA oligonucleotides (Wahlestedt C, et al., *Proc. Natl Acad. Sci. USA*, 975633-5638 (2000); Braasch, D A, et al., *Chem. Biol.* 81-7 (2001): Kurreck J. et al., *Nucleic Acids Res.* 301911-1918 (2002)). In some embodiments, the scaffolded DNAs are synthetic RNA-like high affinity nucleotide analogue, locked nucleic acids. In some embodiments, the staple strands are synthetic locked nucleic acids.

Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen, et al., Science 254, 1497-1500 (1991)). It is chemically stable and resistant to hydrolytic (enzymatic) cleavage. In some embodiments, the scaffolded DNAs are PNAs. In some embodiments, the staple strands are PNAs.

In some embodiments, a combination of PNAs, DNAs, and/or LNAs is used for the nucleic acids encoding the format of information in an NMO. In other embodiments, a combination of PNAs, DNAs, and/or LNAs is used for the staple strands, overhang sequences, or any nucleic acid component of the SMOs.

V. Devices, Data Structures and Computer Control

Described are data structures used in, generated by, or generated from, the described method. Data structures generally are any form of data, information, and/or objects collected, organized, stored, and/or embodied in a composition or medium. For example, the nucleotide sequence associated with a nucleic acid nanostructure labeled with a specific sequence tag, or set of sequences stored in electronic form, such as in RAM or on a storage disk, is a type of data structure. The described method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be described herein.

The methods and general approach towards molecular data storage and computation can be carried out using a computer-based system. In some embodiments, one or all of the method steps are carried out following an input to a computer. For example, data to be encoded can include any digital files and folders from a computer. The digital files are encoded and/or converted to a molecular memory code (e.g., nucleotides, amino acids, polymers, atoms, surfaces. The code is written to the physical memory block used to store the data. The stored data is associated with a set of address codes to identify the memory block. In some embodiments, assembly of the memory blocks is implemented through one or more automated processes, for example, as controlled by a computer. The addresses affixed to the memory block (such that they can be used for subsequent reading, manipulation, selection, and computation, including physical tags, electrostatic or magnetic properties, chemical properties, or optical properties) are recorded in one or more databases or files written to the computer. In some embodiments, physical placement of the memory blocks with addresses within a pool of other memory blocks for storage and computation can be implemented through one or more automated processes, for example, as controlled by a computer. In some embodiments, physical separation based on the physical properties, with some memory blocks satisfying the selection criteria and others not, and sorting are implemented through one or more automated processes, for example, as controlled by a computer. Many cycles of this and other selection criteria can be automated or centrally controlled, for example, to take place in parallel or in series. The selection and computation on these tags is recorded in one or more files or databases recorded by the computer. In some embodiments, physical purification and isolation of selected memory block(s) of interest from the pool is implemented through one or more automated processes, for example, as controlled by a computer. In some embodiments, the sorted memory block(s) are read out and decoded to digital format by one or more automated or centrally controlled processes, to enable automated retrieval of data from the pool.

A. Devices

In some embodiments one or more of the apparatus are connected together to facilitate continuous or intermittent flow throughput the apparatus, as a single system. In some embodiments, the assembly of memory objects from the component parts is implemented with an automated device, or multiple inter-connected devices that combine to produce a system. An exemplary device or system is a microfluidic device or system. In some embodiments, the mixing of bitstream encoded polymers with one or more address tags and optionally one or more encapsulating agents is implemented with a microfluidic system. In some embodiments.

Microfluidics can be used either in traditional 2-phase droplet form or electro-wetting on dielectric (EWOD) form (Nelson and Kim, *Journal of Adhesion Science and Technology*. 26 1747-1771 (2012)) to combine, separate, and otherwise manipulate specific pools of the preceding memory objects for either computation or processing or memory storage/retrieval.

In some embodiments memory storage and retrieval or computation of memory objects are carried out using automated systems.

Memory read-out can either be performed using on-chip nanopore-based single-molecule sequencing for DNA/RNA, or PCR-based amplification and sequencing for optical approaches, or other analytical chemical approaches including mass spectrometry, which exploit molecular or nanoparticle charge, size, mass, etc. to read out the information-content or molecular composition of the nanoparticles; affinity or other specific recognition tags as we've used are also applicable to this workflow. The described methods for the assembly of nucleic acid memory objects can be implemented within a single device. For example, in some embodiments, the assembly of nucleic acid memory objects is achieved using a device including one or more of (a) an inlet, for example, to facilitate the in-flow of one or more components of the nucleic acid memory object from an external source;

(b) apparatus for mixing the constituent components, such as a vortex, a shaker, a stir bar, turbulent flow coil, etc.;

(c) apparatus for annealing the constituent components to form an assembled nucleic acid memory object, such as a controllable heat source, a PCR machine, etc.; and (d) apparatus for purifying the assembled nucleic acid memory object, for example, by affinity chromatography, High Pressure Liquid Chromatography, filtration, etc.

The present invention will be further understood by reference to the following non-limiting examples.

EXAMPLES

Example 1: Design and Organization of Bitstream Data Implemented as Nucleic Acid Memory Objects Methods and Materials Nanostructure Design and Bitstream Data To demonstrate the application of nanostructured nucleic acid to store, organize and selectively access bitstream data, 6 lines from 4 different plays were placed into 6 separate UTF-8 text files on a digital computer. UTF-8 is a variable-length character encoding system, capable of encoding all possible characters, or code points, defined by Unicode format LZMA (Lempel-Ziv-Markov chain algorithm) compression was then applied to 5 of these text files to obtain 5 different compressed files, respectively. In a second implementation, 2 of the initial text files were encrypted by AES (Advanced Encryption Standard) with 128-bit block length using CBC (cipher block chaining) mode to obtain two different encrypted bitstreams. Each of these compressed or encrypted bitstreams were then converted to a DNA sequence with direct encoding of 0 coded to "A" or "C", chosen randomly, and 1 coded to "T" or "G", chosen randomly, with bias in each case against greater than 4 homo-nucleotide repeats. These DNA sequences had a universal end of file (EOF) 20-mer barcode sequence appended to each of them. Additionally, new implementations include prepending the sequence with a file signature sequence for bioinformatics file information handling, and encrypted messages have the encryption initiation vector ("salt") encoded directly as the first 16 nucleotides (chosen randomly, but following sequence rules against repetitions). A slack space of random nucleotides was then appended after the EOF barcode to bring the sequence to the nearest scaffold structure size, matching the size of the chosen object. In five exemplary NMOs the objects were octahedra of two different edge lengths and 2 duplexes per edge. The first octahedral structure included a scaffold of 1,008 nucleotides for an octahedron of edge length 42, used to encode lines from each of three literary texts "*The Crucible*", "*Waiting for Godot*", and "*Hamlet*", respectively. The second octahedral structure included a scaffold of 1,248 nucleotides for an octahedron of edge length 52, for encoding a line from each of two literary texts "*Romeo and Juliet*", and a second line from "*Hamlet*"). In another exemplary NMO, the object was a reinforced cube (2,124 nucleotides that encoded a third line from "*Hamlet*"). Universal primer sequences were then prepended and appended to these DNA sequences to allow for amplification of messages and asymmetric Polymerase chain reaction (APCR). The National Center for Biotechnology Information (NCBI) program suite "BLASTN" with word-length 7 was used to identify any repeat sequences and the sequences were changed if needed by flipping the base but maintaining the underlying binary digit.

The sequences between the universal primers were exclusively applied to the computational scaffold routing method with octahedron or reinforced cube geometries and the defined edge length, as described above. The octahedron was either of edge-length 42 base pairs from vertex to vertex (#1, "Hamlet"—message 1, #2, "Waiting for Godot", and #3, "Crucible"), or 52 base pairs (#4, "Hamlet"-message 2), respectively. The staple sequences with outward-facing nick positions were outputted from the routing method. 6-8 tags were generated for each line of text to provide metadata for the encoded message. These tags included encoded information that described the title, genre, speaker, other active participants, the author, the date it was first performed, a random message index, the act and scene of the play, and any important context (e.g. "tree" in "*Waiting for Godot*", referenced in the particular conversation for which the line is taken).

The messages and the metadata used for tagging for each of the three octahedron structures with edge-length 42 base pairs from vertex to vertex were as follows.

Memory object #1:
  Message: "I'm like that. Either I forget right away or I never forget."
  Metadata used for tagging: Waiting for Godot. Estragon. Act II U6. Samuel Beckett. Jan. 5, 1953.
Memory object #2:
  Message: "The answer is in your memory and you need no help to give it to me. Why did you dismiss Abigail Williams?"
  Metadata used for tagging: The Crucible. Danforth. Act III. Arthur Miller. Jan. 22, 1953. To Elizabeth. About Abigail. Proctor present.
Memory object #3:
  Message: "Tis in my memory lock'd, And you yourself shall keep the key of it."
  Metadata used for tagging: Hamlet. Ophelia. Act I, Scene III. Shakespeare. 1599. To Laertes
Memory object #4:
  Message: "There are more things in Heaven and Earth, Horatio, than are dreamt of in your philosophy."
  Metadata used for tagging: Hamlet. Hamlet. Act I, Scene V. Shakespeare. 1599. To Horatio Direct text to DNA coding was used for addressing using one ASCII character to three nucleotides. Additional implementation of barcode addressing are carried out using 16-bit cyclic redundancy code (CRC16) hash function conversions of text to hash integer to DNA base-4 code. These generated sequences were then placed on the 3' end of the selected staples, with nicks close to the center of the edge of the structures. The scaffold (provided as double-stranded DNA (dsDNA) in the form of a GBLOCK®) and staples were then ordered and commercially prepared by Integrated DNA Technologies, Inc. The dsDNA was amplified by a high-fidelity enzyme (PHUSION®, NEB) and gel purified, and was also cloned to a pUC19 vector using flanking PstI cut sites. The dsDNA was then amplified to single-strand DNA (ssDNA) using asymmetric PCR for each message and gel purified. Sanger sequencing (GeneWiz, Inc.) using the reverse primer was carried out to verify the sequence of the product, as well as the recovery of the encoded message. The scaffold strands of these bitstream DNA were mixed with their respective staples in 1×TAE+12 mM $MgCl_2$, and slowly annealed over 18 hours from 95° C. to 25° C. in individual tubes per NMO. The individual NMOs were tested for assembly using gel mobility shift assays on 2% agarose and visualized under UV light with SYBR Safe DNA stain. The NMOs were then pooled into a single tube, making a memory pool of NMOs.

Results

The efficacy of sorting and accessing the bitstream data encoded within nucleic acid nanostructures was demonstrated using standard Boolean logic operations, (including NOT logic; OR logic; AND logic) to select and organize distinct subgroups of data blocks from the pool of four different blocks.

Boolean NOT Logic

Figure 10:
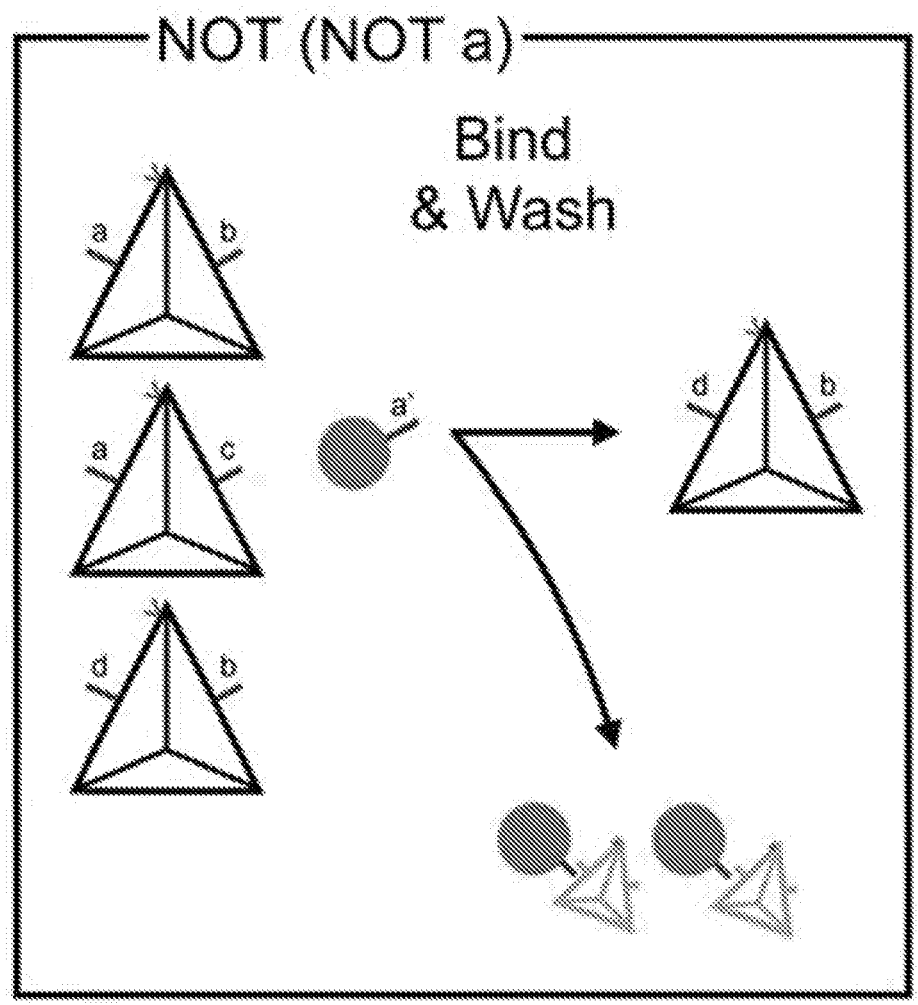
FIG. 10 is a schematic illustration depicting the workflow for the method used to compute a NOT logic operation on the NMO pool. (a pool of differently addressed NMOs is depicted; NMOs having overhang tag sequences of a are captured on the capture support using the capture sequence complementary to a (a') and thus unbound objects from this capture support are all those objects which do not contain the a overhang, thus NOT a. Tetrahedra are representative of any memory objects, including encapsulated nucleic acids or other information-bearing biological or synthetic polymers.

Sorting and accessing specific bitstream data from the pool of NMOs by applying NOT logic to the pool was tested as follows. A biotinylated oligonucleotide was purchased having the reverse complement sequence to the sequence tag encoding the title "HAMLET". The oligonucleotide was affixed to streptavidin coated magnetic beads and the unbound oligonucleotides were washed away. 15 μL of a pool of two NMO octahedra (1 encoding a line from *Waiting for Godot* and 1 encoding a line from *Hamlet*) at 100 nM NMO concentration total was added to functionalized beads and incubated at 37° C. with bead-oligonucleotides in excess in 1×TAE+100 mM NaCl+12 mM $MgCl_2$ under constant agitation for 30 minutes. The beads were then collected by a magnet. The unbound fraction was collected (representing the NOT "HAMLET" population). The bound fraction was washed four times with buffer and re-pelleted after each wash. The beads were finally brought up in 10 μL $H_2O$ and heated at 65° C., then pelleted and the supernatant was collected (representing the unfolded NMO containing the scaffold sequence encoding the bound fraction of the HAMLET selection). 5 μL of the two fractions were separately amplified using the universal surrounding primers, gel purified, and Sanger sequenced with forward and reverse primers. The sequencing from the NOT "HAMLET" fraction matched identically the sequence expected from the *Waiting for Godot* line, while the sequence of the scaffold of the NMO that was captured by the "HAMLET" oligonucleotide matched identically the sequence expected from the *Hamlet* line of the memory pool. Therefore, memory selections have been shown to be feasible, including NOT logic. A schematic representation of the use of NOT logic to sort and access information from a pool of NMOs is depicted in FIG. 10.

Additional Logic

Sorting and accessing specific bitstream data from the pool of NMOs by applying additional logic to the pool was demonstrated by use of the AES-encrypted bitstream data encoding for the message from The Crucible. The message was folded with 2 overhang sequences calculated from the CRC16 hash of "Title: The Crucible" and "Author: Arthur Miller", respectively. The exemplary object was an octahedron of length 42 base pairs from vertex to vertex. The object was either alone in a tube or mixed with 1:1,000 or 1:10$^6$ molar equivalents less than tetrahedra of length 63 base pairs from vertex to vertex. The tetrahedra of length 63 base pairs from vertex to vertex were also formed by the same method of staples and slow annealing, and had two overhang tags of 18 nucleotides that were random in sequence (IDT). The scaffold of the tetrahedron was flanked on the 5' and 3' ends with precisely the same sequence as the Crucible block. This effectively (1) hid the Crucible memory block in a mix of other memory blocks and (2) simulated the extraction of 1 memory block from a mix of memory blocks similar to pulling a kilobyte of information from 1 megabyte pool or 1 gigabyte pool of data.

Boolean OR Logic

Data selections were tested on the Crucible memory block. Two oligonucleotides were synthesized (IDT) to be complementary to the two overhangs of the Crucible block. Additionally, 8 nucleotides with 50% GC content were added followed by a 3' biotin group. 10 µL of 500 µM oligonucleotide capture strands were incubated at 37° C. with 150 µL of streptavidin magnetic beads with periodic mixing for 30 minutes. The beads were extracted by magnets and washed 4 times with 150 µL of 20 mM HEPES-NaOH pH 7.6, 200 mM NaCl, 12 mM MgCl$_2$ ("buffer W"), by pelleting and resuspension. 150 µL of 15 nM NMO was then added to either the bead pool labeled with the complementary strand of tag 1, or the bead pool labeled with the complementary strand of tag 2. The NMO was annealed to the bead by placing in a thermocycler programmed to anneal from 40° C. to 25° C. over 1 hour. The bead-NMO solution was then washed in buffer W 4 times at 150 µL each, with pelleting and resuspension between each wash. 10 µL of 200 µM release strand was then added to each pool, the release strand being given by the sequence complementary to the capture sequence including the 8 nucleotides unpaired to the NMO address. The thermocycler was set to anneal from 40 C to 25 C in 0.5 C increments over the course of 30 minutes, followed by a melting step of 25 C to 40 C in 0.5 C increments over the course of 30 minutes. This has the effect of releasing the NMO without disrupting the structure. The beads were subsequently pelleted and the supernatant was taken for further analysis including with gel based analysis, PCR amplification, and qPCR quantitation.

Figure 9:
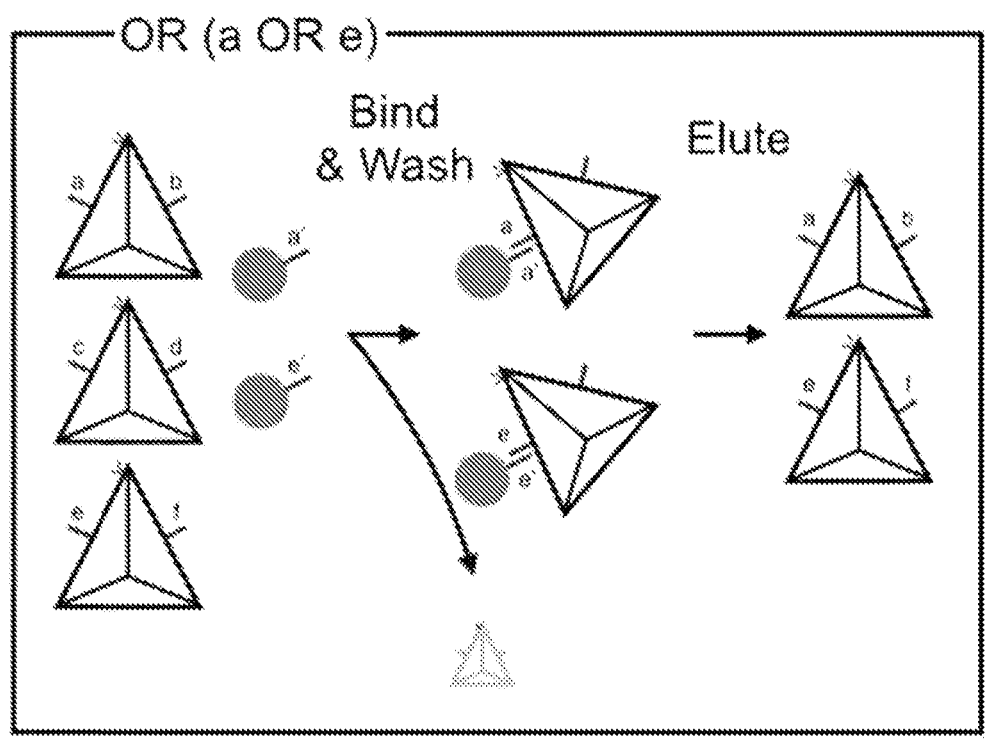
FIG. 9 is a schematic illustration depicting the workflow for the method used to compute an OR logic operation on the NMO pool. A pool of differently addressed NMOs is depicted; NMOs containing an overhang of sequence a OR an overhang of sequence e are captured using capture support with sequences complementary to a (a') and e (e'), with NMOs containing neither being washed off the capture support; captured NMOs having an overhang of sequence a OR an overhang of sequence e are then released from the support. Tetrahedra are representative of any memory objects, including encapsulated nucleic acids or other information-bearing biological or synthetic polymers.

OR logic was tested on the Crucible NMO. The capture oligonucleotides were mixed 1:1 and added together simultaneously to streptavidin labeled magnetic beads. The beads were washed as before, and incubated and annealed to the Crucible NMO as before. Again, the beads were washed after annealing. The NMO was released by the addition of both release strands simultaneously and cycled as described above. The released NMO was taken for further analysis including with gel based analysis, PCR amplification, and qPCR quantitation. A schematic representation of the use of OR logic to sort and access information from a pool of NMOs is depicted in FIG. 9.

Boolean AND Logic

AND logic was tested on the Crucible NMO. The biotinylated capture oligonucleotide 1 was affixed to the streptavidin magnetic beads in the same method as above and separately biotinylated capture oligonucleotide 2 was affixed to a different pool of streptavidin magnetic beads. The NMO was incubated with the bead pool 1, after washing, and was subsequently washed and released using the 8-nucleotide toe-hold thermal-cycling as above in 150 µL. The released NMOs were separated from the magnetic beads by a strong magnet. The released fraction was then incubated with the capture oligonucleotide bead 2 pool and annealed. The beads were again washed 4 times in 150 µL buffer W and released by incubation and thermocycling in the presence of the release strand 2 through toe-hold mediated release in 150 µL. The beads were again pelleted and the supernatant was collected for gel analysis, PCR amplification, and qPCR quantitation.

For gel analysis, 20 µL of the released NMO was mixed with 4 µL 6× loading dye (NEB) and ran on a 1% agarose gel containing 12 mM MgCl$_2$ in 1×Tris-Acetate-EDTA buffer cast with 1× SybrSafe (ThermoFisher) and visualized under blue light. For PCR analysis, 0.4 µL of the 150 µL supernatant from any of the experiments was used as a template with 200 µM forward and reverse universal primers, 200 µM dNTPs, 1χ HF Phusion buffer, and 0.01 µL/µL reaction mix Phusion enzyme and thermocycled 25 times. 8 µL of the amplified product was ran on a 1% agarose gel for visualization against a template control. For qPCR analysis, the NMO supernatant was added without dilution or in a 1:100 dilution to 20 µL reactions of the Phusion enzyme and buffer in the presence of 2× SybrGreen I and cycled with detection using a ThermoFisher QS6. Amplification allows for detection of relative amounts of template and thus a relative measure for the amounts captured. This could be achieved similarly with digital qPCR.

Besides Sanger sequencing as a readout, the purified NMOs could be amplified and indexed per experiment and then sequenced using next generation sequencing on the Illumina MiSeq platform or by affixing the sequence with the amplification target SMRTBell sequence for PacBio sequencing or affixed with the targeting sequence for the Oxford nanopore sequencer. Irrespective of the sequencing method used, the messages is assembled using known bioinformatics methodology. The DNA sequence is searched for the EOF (end of file) barcode, and all DNA after and including that sequence will be removed. Additionally, the DNA sequence of the master forward primer will be removed, a file type identifier, if present, will guide file-type computational processing, and any additional file-specific extraneous sequences will be removed for decoding including the encryption salt as needed, ultimately leaving just the encoded bitstream. The message will then be decoded using reverse coding to 0s and 1s, and then decompressed or decrypted as indicated by the file type identifier. It is to be noted that the password for encryption can be distinct per use, or distinct per memory block, or can be distinct per user, and so on. Thus the password and salt can offer added security to clients with the synthesis and NMO assembler intermediaries not knowing the unencrypted files. As the CRC16 and similar hashes are cryptographic and irreversible, these offer added security to the client protecting their data. A schematic representation of the use of AND logic to sort and access information from a pool of NMOs is depicted in FIG. 8.

Example 2: Design of Nucleic Acid Memory Object Superstructures

Methods

Figure 18A:
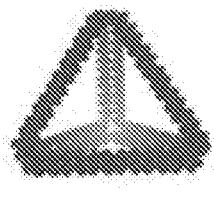
FIGS. 18A-18F shows example outcomes from NMO super-structuring.
Figure 18B:
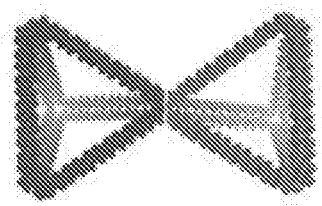
Figure 18C:
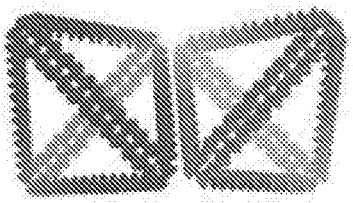
Figure 18D:
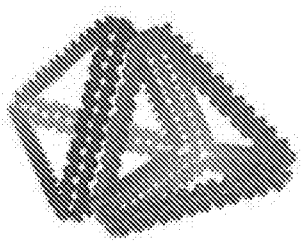
Figure 18E:
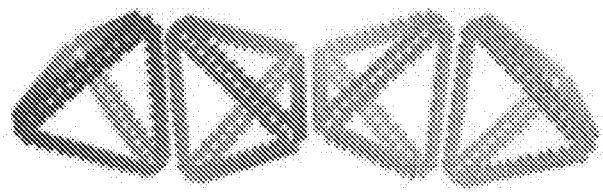
Figure 18F:
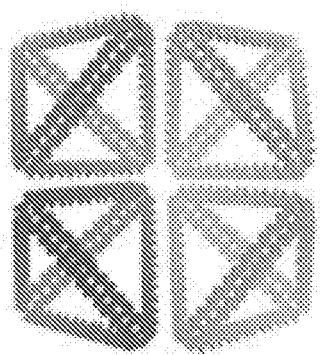

Super-structuring by complementary overhangs was tested using two tetrahedra. 3' single-strand DNA overhangs off two different staple nicks on the same edge of a tetrahedron with edge-length 63 nucleotides were generated, with a scaffold of a sequence amplified from M13 phage genomic DNA. Sequences complementary to the two overhangs on the first tetrahedron (tet-A) were generated and placed as 3' single-strand DNA overhangs of two different nicks on the same edge of a second tetrahedron, with a scaffold also amplified from M13 genomic DNA (tet-B). These two structures with complementary overhangs were separately folded and purified, and then pooled and slowly annealed over two hours from 43° C. to 25° C. Verification of superstructuring was done via gel shift mobility assay on 2% agarose and visualized under UV light with SYBR Safe DNA stain. The gel showed a shift indicative of quantitative dimer formation. This same exact procedure is used for superstructuring NMOs by use of complementary strands per edge. Further, a series of 4 tetrahedra were structured such that two overhangs per edge were made complementary to a second tetrahedron, which had opposite to that edge a second set of two overhangs complementary to a second dimer-set. Thus 2 tetrahedra dimers were annealed to each other to form a tetramer of tetrahedra (depicted in FIGS. 18B-18D). The same scaffold sequence was used to forma set of tetrahedral of the same scaffold but with different addresses that had curvature to the superstructure that caused the 4 tetrahedra to close back to itself. Thus NMOs can be assembled to be in elongated or closed superstructures dependent on the exposed addresses.

Results

To demonstrate NMO superstructuring, NMOs were brought together at their vertices, along their edges, or at their faces using overhang addressing. Exemplary tetrahedra were demonstrated as coming together in larger superstructures by a Gel mobility shift assays indicating superstructuring as compared to monomer NMOs, dimer NMOs, and tetramer NMOs, respectively. Extended tetramers were addressed to come together along the edges via complementarity, as determined by transmission electron microscopy showing the extended configuration. The same tetrahedra, but with different addresses, were observed as forming different compact configurations.

Example 3: Paper Storage of Nucleic Acid Memory Object Structures

Methods

Storage of NMOs on paper as a medium for long-term preservation was tested. Whatman paper type 42 was cut to mm scale (typically 2 mm×5 mm) and saturated with 15 μL 1×TAE+12 mM $MgCl_2$+1% PEG 8000 w/v. The paper was then dried under vacuum in the presence of desiccant. 15 μL of 40 nM DNA nanostructures (tetrahedra with edge-length 63 nucleotides) was then added to the paper and dried under vacuum. After at least 14 hours at room temperature the paper was transferred to a separate tube and washed with 15 μL folding buffer, and the solution was separated from the paper by centrifugation. Gel mobility shift assays indicated structural stability. Likewise, NMOs can be stored for long lengths of time and resuspended as needed.

Results

NMOs were dried and stored to paper that was pretreated with 1% Polyethylene glycol 8000 before exposed to NMOs. The NMOs transferred to the paper were later rehydrated, and were still present in assembled form, as indicated by a Gel-shift assay. Exemplary paper tabs containing dried NMOs were stored within a single Eppendorf tube.

Example 4: Metal Oxide Storage of Nucleic Acid Memory Object Structures

Experiments to demonstrate the packaging and accessibility of nucleic acids by encapsulation or coating in a non-nucleic acid polymer were carried out. Briefly, nucleic acids were encased within a polymer, addressed with one or more tags (depicted in FIGS. 4A-4D and FIGS. 17A-17D).

Methods and Materials

Preparation of Silica particles Silica particles were prepared by mixing 800 μL of 25% w/w ammonium hydroxide, 800 μL of tetraethoxysilane, and 500 μL of distilled water in 18 mL of water. The mixture was shaken on a platform orbital shaker at 500 rpm for 6 hours at room temperature. The mixture was then centrifuged at 9,000 g for 20 minutes at room temperature and the supernatant was discarded. The silica pellets were re-dispersed in solution by adding a total of 20 mL of isopropanol then sonicating for 1 minute at room temperature and vortexing for 5 seconds to get a homogenous colloidal solution. The mixture was again centrifuged at 9,000 g for 20 minutes at room temperature and the supertanant was again discarded. The pellet was re-dispersed in solution by adding a total of 4 mL of isopropanol, sonicating for 1 minute, and vortexing for 5 seconds until a homogenous dispersion is again achieved.

Modification of Silica Particles to Facilitate Adsorption of DNA Particles The silica particles were immediately modified by taking a 1 mL aliquot of the silica particles and adding 10 μL of 50% w/w N-trimethoxylsilylpropyl-N,N,N-trimethylammonium (TMAPS) chloride in methanol. The mixture was shaken on a platform orbital shaker at 500 rpm for 12 hours at room temperature. The mixture was then centrifuged at 21,500 g for 4 minutes discarding the supernatant. The modified silica pellets were suspended with 1 mL of isopropanol, sonicated for 1 minute, and vortexed for 5 seconds to achieve a homogenous solution. The mixture was again centrifuged at 21,500 g for 4 minutes and the supernatant was again discarded. The same washing procedure was repeated twice to remove residual TMAPS in solution.

Encapsulation of DNA particles

Figure 17A:
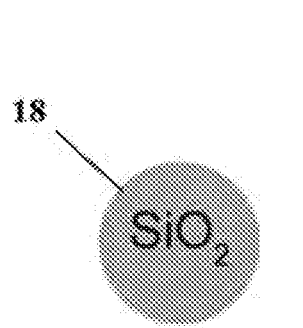
FIGS. 17A-17D are schematic illustrations of the silica encapsulation of polymer memory blocks.
Figure 17B:
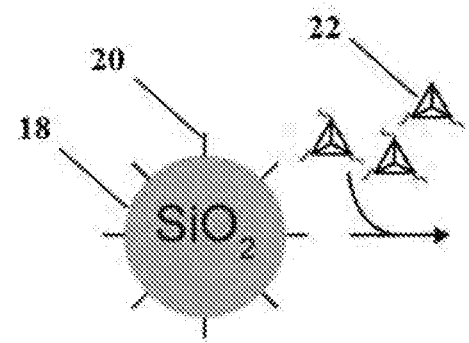
Figure 17C:
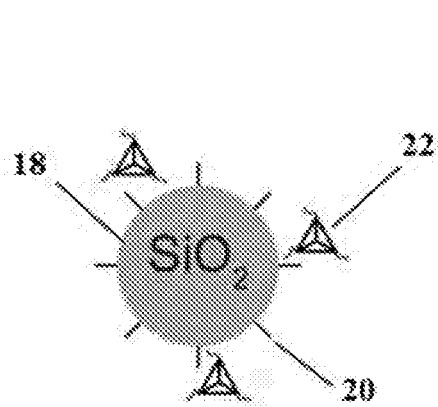
Figure 17D:
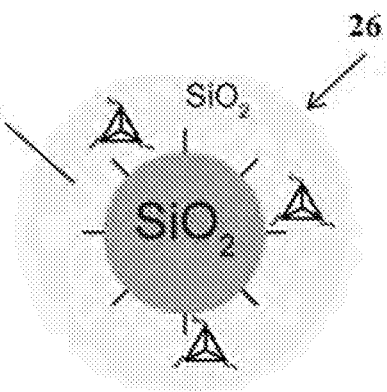

A double-crossover (DX) tile modified with Cy3 and Cy5 energy transfer pair as a readout was encapsulated by adding 320 μL of 50 μg $mL^{-1}$ Cy3 and Cy5-modified DX tile to 700 μL of water and 35 μL of functionalized silica particles (FIG. 17D). The mixture was shaken on a microtube revolver for 3 minutes at room temperature then centrifuged at 21,500 g for 4 minutes discarding the supernatant. The silica pellets were then suspended with 1 mL of DNAse-free water, sonicated for 1 minute at room temperature, and vortexed for 5 seconds. The mixture was then centrifuged at 21,500 g for 4 minutes discarding the supernatant. The silica pellets were re-suspended with 500 μL of DNAse-free water, sonicated for 1 minute at room temperature, and vortexed for 5 seconds. To this mixture, a volume of 0.5 μL TMAPS was added and mixed by vortexing for 5 seconds. An additional 0.5 μL of TEOS was then added. The mixture was shaken on a microtube revolver for 4 hours at room temperature then 4 μL of TEOS was added. The mixture was further shaken on a microtube revolver for 4 days. The mixture was centrifuged at 21,500 g for 4 minutes discarding the supernatant. The silica-encapsulated DX tile pellet was re-suspended with 500 μL of DNAse-free water, sonicated for 1 minute at room temperature, and vortexed for 5 seconds. The mixture was again centrifuged at 21,500 g for 4 minutes discarding the supernatant. The pellet was re-suspended with 100 μL of DNAse-free water, sonicated for 1 minute at room temperature, and vortexed for 5 seconds. The DX-tile is finally encapsulated. Schematic illustrations of the silica encapsulation of nucleic acid memory blocks are depicted in FIGS. 17A-17D.

The encapsulated particles were drop casted on paper to test the protective particles of silica with DNA. A volume of 10 μL was dropped on paper and was allowed to dry in ambient temperature. A volume of 10 μL of DNA denaturants (0.1 M HCl, 0.1 M NaOH, and DNAse) was then added and allowed to dry again at room temperature.

Results

The surface of the silica particles was modified to allow adsorption of DNA memory objects, such that the modified silica particles act as a scaffold for the nucleic acid memory blocks to bind onto.

Figure 17E:
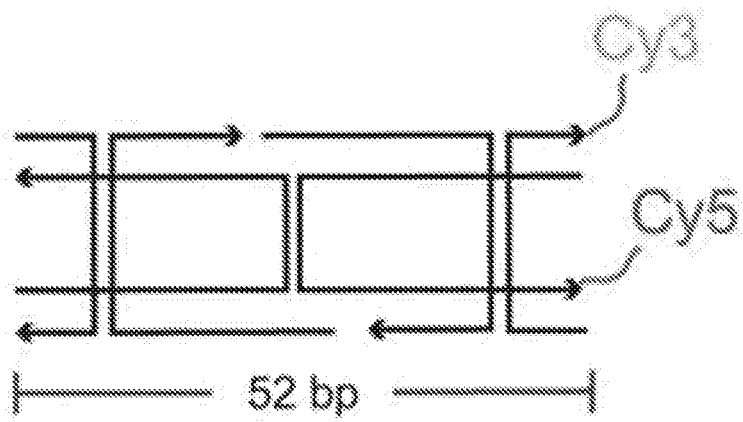
FIG. 17E is a schematic of an exemplary DNA assembly (a double-crossover or DX tile) containing Cy3 and Cy5 energy transfer pair as a readout for monitoring the structure of the DX tile.

The nucleic acid memory blocks are first adsorbed to the surface-modified silica particles, then a secondary silica shell is appended onto the silica with the nucleic acid memory blocks adsorbed. A schematic of an exemplar DNA assembly (a double-crossover or DX tile) containing Cy3 and Cy5 energy transfer pair as a readout for monitoring the structure of the DX tile is provided in FIG. 17E. This shell provides environmental protection for the nucleic acid memory blocks.

Figure 17F:
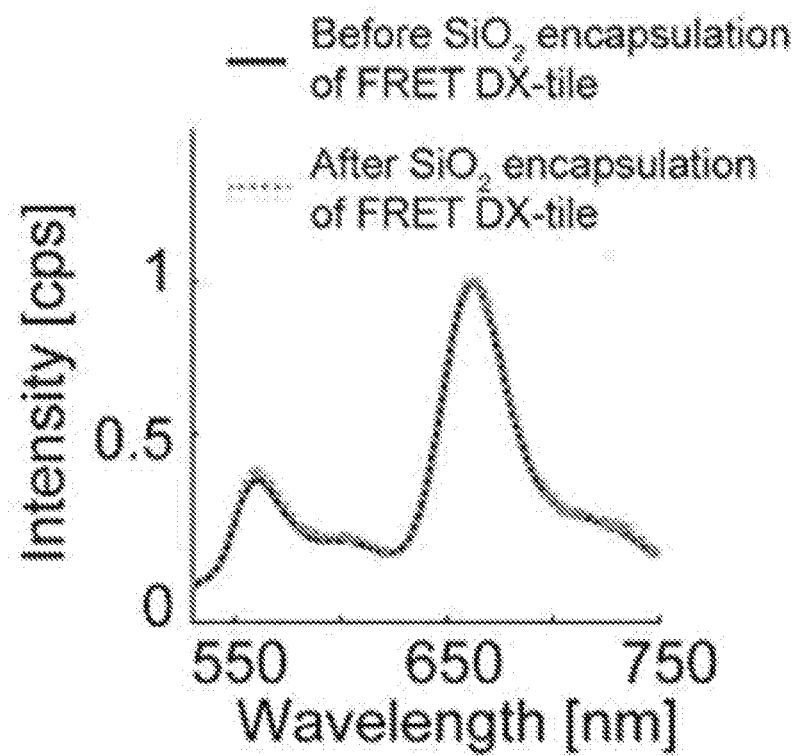
FIG. 17F is a graph showing Intensity (cps) over Wavelength (nm) corresponding to the emission spectra of the DX tile prior to the encapsulation process (-), and the emission spectra of the DX tile upon completion of the encapsulation step (--), respectively.

Assessment of the encapsulated particles was carried out by comparing silica-encapsulated particles with non-encapsulated nanoparticles under UV illumination filtering only Cy5 fluorescence using a longpass filter. No change in the emission spectra of the DX tile upon completion of the encapsulation step showing that the encapsulation process does not perturb the structure of the DX tile (see FIG. 17F).

To assess protection of DNA memory objects by the silica encapsulation process, silica-encapsulated DX tiles were absorbed onto a strip of paper and exposed to 0.1 M NaOH, 0.1 M HCl, and DNAse. The silica-coated paper was excited at 400 nm and the emission was selected using a 650 nm longpass filter.

Example 5: Microfluidic Device for Automated Assembly of Nucleic Acid Memory Object Structures Methods and Materials A system for the automated assembly of nucleic acid memory objects was designed and assembled to include the device 3D printed to a size of 10 cm by 4 cm, with 3 input ports, a mixer and annealer over a copper plate, and 3 output ports, with one foot of the copper plate in 80° C. water bath and the other foot of the copper plate in ice water.

The input port was connected to a fluid pump and the output was connected to a fraction collector tube, with the fluid flow passing first from the reagents, including bitstream scaffold nucleic acid, tagged staple strands and staples, into the mixer, then from into and through the annealer into a fraction collector. Within the annealer the fluid passes from high temperature to a low temperature. Fractions were collected and purified by filtration.

Figure 13:
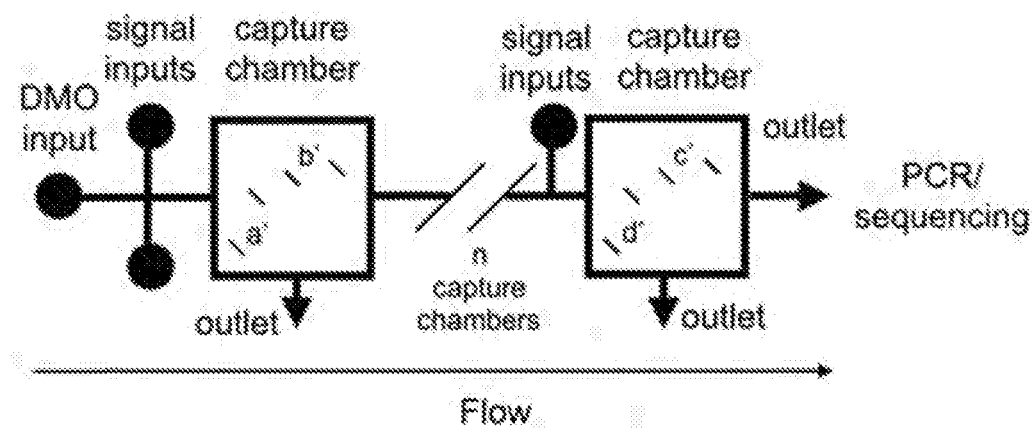
FIG. 13 is a schematic illustration depicting the workflow implemented within an exemplary microfluidic device allowing for the rapid purification of the nanostructure NMOs, including the ability to "daisy-chain" the devices for complex logic gating. Multiple out-ports on the capture chamber allow for AND/OR/NOT logic implementation at the microfluidic level. A memory pool of NMOs; exemplary signal input for selection of the target NMOs based on their tag overhangs; an exemplary capture chamber for capturing, washing, and elution for selecting based on the input signal (s); unlimited number of signal input and capture chambers for executing the selection; further exemplary signal input for selection of the target NMOs based on their tag overhangs; further exemplary capture chamber for capturing, washing, and elution for selecting based on the input signal (s); the final output where the scaffold sequence encoding desired information is amplified, sequences and decoded. Electro-wetting-based droplet manipulation devices such as the Mondrian may be used to perform these controlled mixing and splitting operations in a rapid and controlled manner that is also fully automated.
Figure 15A:
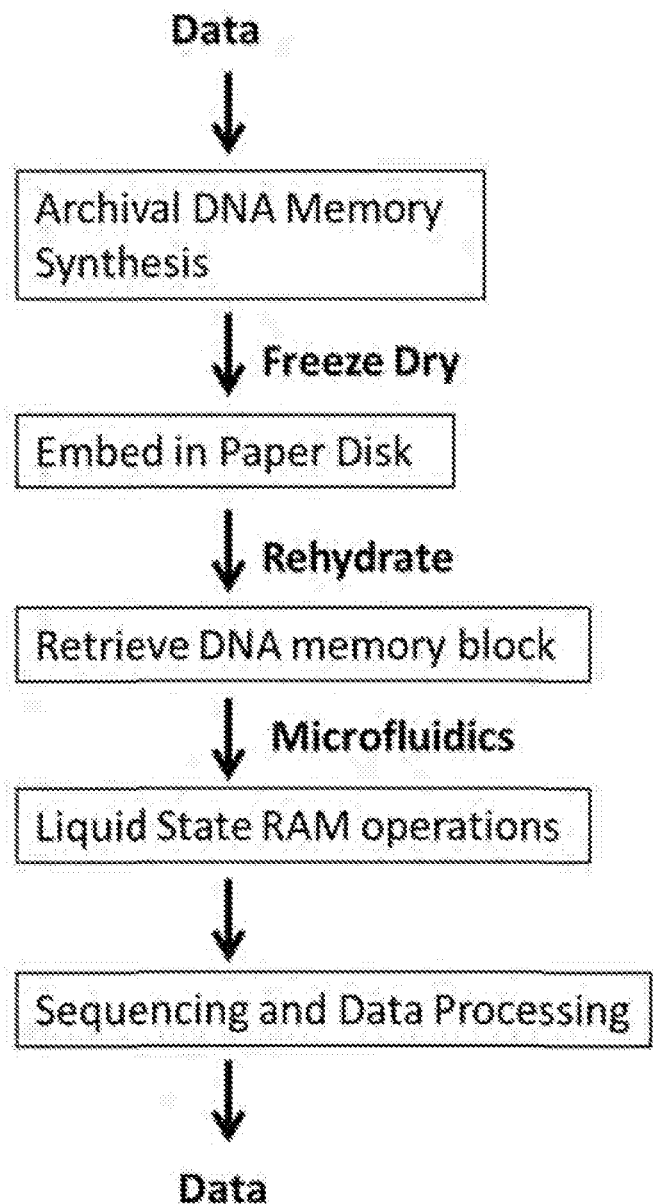
FIGS. 15A and 15B are flow charts.
Figure 15B:
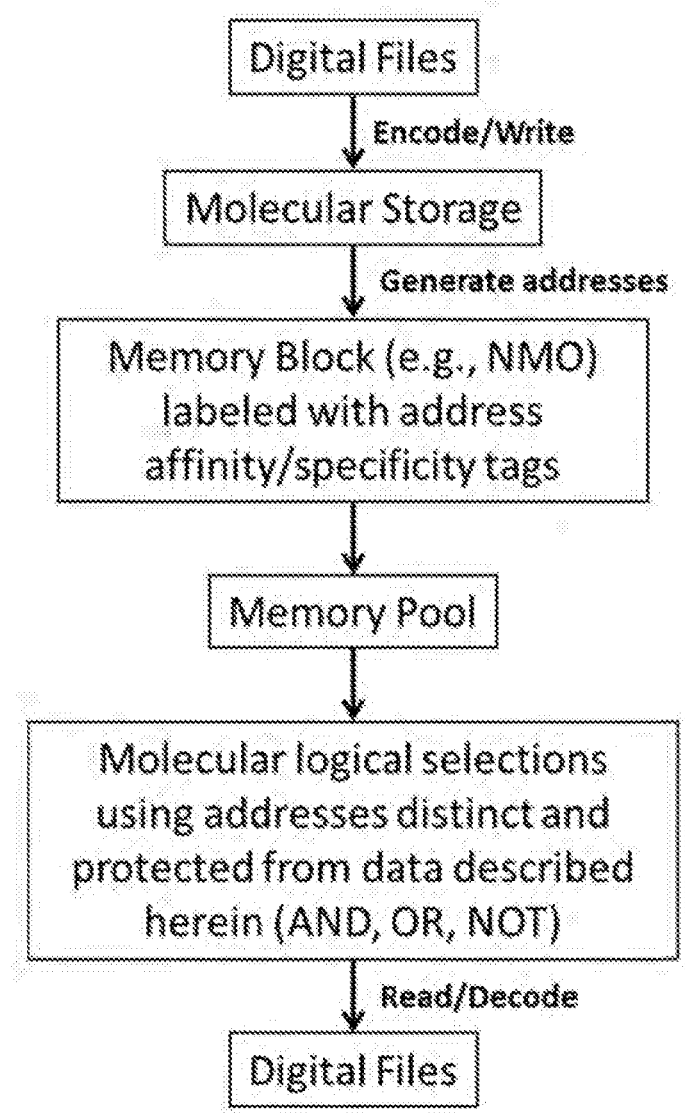

The DNA nanoparticles annealing reaction in the auto-assembler was realized in 1.2 mL reaction volume with ssDNA scaffold at a concentration of 80 nM and a 15× excess of staple strands in Tris-Acetate EDTA-MgCl$_2$ buffer (40 mM Tris, 20 mM acetic acid, 2 mM EDTA, 12 mM MgCl$_2$, pH 8.0). Before injection of the sample the device was washed with 4 mL of folding buffer at a flow rate of 100 μL/min. For the sample injection, the flow rate was maintained at 10 μL/min through the auto-assembler channel using a Gilson, Inc. MINIPULS® 3 peristaltic pump. The temperature gradient in the auto-assembler was created by connecting one of the extremity of the copper plate (Denaturation area) to an 80° C. water bath and the collecting extremity of the copper plate to a cold water bath kept at 4° C. Sample collection was regularly monitored using a nanodrop. A schematic representation of the automated system is depicted in FIG. 12. The exemplary work-flow for implementation of automated systems within exemplary microfluidic devices are also depicted in FIGS. 13, 14 and 15.

Output from the auto-assembler was tested by gel on a 1% agarose gel supplemented with 12 mM MgCl$_2$.

Results

The resulting nanostructure assemblies were assessed by gel electrophoresis. The folding of assembled objects was determined by visual observation of gel bands in each lane of the gel corresponding to scaffold nucleic acid alone, scaffold mixed at room temperature with staples, scaffold and staples mixed and annealed over 3 hours in a thermal cycler, and scaffold and staples mixed and annealed over 3 hours on the auto-assembler.

Gel-shift assays were used to test folding. Lanes corresponding to the scaffold and staples mixed and annealed over 3 hours in a thermal cycler were of equal position and intensity to those in the gel lane corresponding to the scaffold and staples mixed and annealed over 3 hours on the auto-assembler. The experiment demonstrated the efficacy of the auto-assembly system is at least as efficient as assembly using a thermal cycler.

We claim:

1. A method of storing desired media as a sequence-controlled polymer memory object, comprising
    (a) assembling a memory object from a sequence-controlled polymer encoding the desired media, wherein the memory object comprises
        i. the sequence-controlled polymer;
        ii. one or more address tags; and
        iii. optionally an encapsulating agent,
    wherein the encapsulating agent coats or encapsulates the sequence-controlled polymer, and
    wherein the one or more address tags are present at the surface of the memory object, and
    wherein the address tags are not embedded within the sequence-controlled polymer; and
    (b) storing the memory object.

2. The method of claim 1, wherein the sequence-controlled polymer is a sequence of molecules selected from the group consisting of naturally occurring nucleic acids, non-naturally occurring nucleic acids, naturally occurring amino acids, non-naturally occurring amino acids, peptidomimetics, carbohydrates, block co-polymers, and combinations thereof.

3. The method of claim 2, wherein the sequence-controlled polymer is a nucleic acid sequence, and wherein assembling the memory object in step (a) further comprises folding the nucleic acid sequence into a nanostructure having a 3D polyhedral or 2D polygon geometric shape.

4. The method of claim 1, wherein assembling the memory object in step (a) further comprises
   i. rendering a desired media into a binary format, and
   ii. converting the binary format to a sequence controlled polymer.

5. The method of claim 1, further comprising the step of
   (c) contacting a first memory object with a second, or further memory object to form a memory object superstructure,
   wherein the superstructure comprises two or more memory objects physically connected by specific or non-specific aggregation or association.

6. The method of claim 1 wherein the address tags comprise oligonucleotide sequences complementary to one or more address tags of a different memory object.

7. The method of claim 1, wherein two or more memory objects are organized into superstructures for storage via complementarity of the nucleotide sequences from the one or more address tags, or to a bridging oligonucleotide.

8. The method of claim 1, wherein the encapsulating agent is selected from the group consisting of a natural polymer, a synthetic polymer, and combinations thereof.

9. The method of claim 1, wherein the encapsulating agent is selected from the group consisting of proteins, polysaccharides, lipids, nucleic acids, and combinations thereof.

10. The method of claim 3, wherein assembling the memory object in step (a) further comprises designing a nucleic acid nanostructure based on a desired 3D polyhedral or 2D polygon geometric shape.

11. The method of claim 10, wherein the nucleic acid nanostructure comprises a single strand of nucleic acid that forms a scaffold sequence that is routed throughout the entire structure, and one or more custom staple strands that fold the scaffold sequence into a user-defined shape.

12. The method of claim 10, wherein the nucleic acid nanostructure comprises a continuous single strand of DNA/RNA that folds onto itself using anti-parallel or parallel crossovers, or some combination of each, or alternatively consisting of purely shorter strands of DNA/RNA, or some mixture or combination of these types of self-assembled nucleic acids.

13. The method of claim 11 wherein the staple strands comprise from 14 to 1,000 nucleotides, inclusive.

14. The method of claim 1, wherein the desired media is provided within a single-stranded nucleic acid sequence comprising approximately 100 to 1,000,000 nucleotides, inclusive.

15. The method of claim 10, wherein one or more staple strands include address tags at the 5' end, at the 3' end, or at both the 5' end and at the 3' end.

16. The method of claim 1, wherein the address tags comprise one or more overhang oligonucleotide sequences.

17. The method of claim 16, wherein the overhang oligonucleotide sequence encodes information.

18. The method of claim 10, wherein designing a nucleic acid nanostructure comprises scaffold routing, staple strand selection, designing of address tags associated with staple strands,
   wherein the staple strands have nicks as part of the formation of the nanostructure where the 5' end of the staple meets the 3' end of itself or another staple, and
   wherein the address tags are added at end of the staple strands.

19. The method of claim 18, wherein the nucleic acid nanostructure is designed to have the geometric shape of any regular or irregular polyhedron.

20. The method of claim 18, wherein the geometric shape is selected from the group consisting of a Platonic polyhedron, Archimedean polyhedron, a Johnson polyhedron, a Catalan solid, helical lattice structures, square lattice structures, honeycomb lattice structures, brick-like cubes, brick-like rectangles, and objects of arbitrary wireframe geometry.

21. The method of claim 1, further comprising the step of
   (d) retrieving the desired media.

22. The method of claim 21, wherein retrieving the desired media in step
   (d) comprises isolating one or more memory objects from a pool of memory objects.

23. The method of claim 22, wherein selection is determined by the sequence of one or more address tags on the memory object, the shape of the memory object, affinity to a functionalized group bound to the memory object, or combinations thereof.

24. The method of claim 23, further comprising the step of modifying the isolated nucleic acid memory object by addition of one or more different address tags.

25. The method of claim 24, wherein addition of one or more different address tags includes refolding, or re-organizing the memory object with one or oligonucleotides including the different address tags.

26. The method of claim 25, wherein one or more memory objects are isolated from a pool of memory objects using Boolean logic.

27. The method of claim 26, wherein Boolean NOT logic is used to delete one or more memory objects from a data pool.

28. The method of claim 1, further comprising the step of
   (e) accessing the desired media.

29. The method of claim 28 wherein accessing information in step (e) comprises
   i. selecting target address tags using oligonucleotide sequences that are complimentary to the target address tags;
   ii. acquiring the sequence of the sequence-controlled polymer encoding the desired media;
   iii. converting the acquired sequence to bit sequences, and
   iv. converting the bit sequences to the original format of the desired media.

30. A sequence-controlled polymer memory object, comprising
   (a) one or more sequence-controlled polymers,
   wherein the sequence-controlled polymer encodes a desired media in bit-stream format, and
   (b) one or more address labels
   wherein the one or more address labels are not embedded within the sequence-controlled polymer.

31. The memory object of claim 30, wherein the sequence-controlled polymer is a single stranded nucleic acid, and
   wherein the nucleic acid is folded into a three-dimensional polyhedral nano structure comprising two nucleic acid helices that are joined by either anti-parallel or parallel crossovers spanning each edge of the structure,
   wherein the three-dimensional polyhedral structure is formed from single stranded nucleic acid staple sequences hybridized to the single stranded nucleic acid including bit-stream data, wherein the single stranded nucleic acid including bit-stream data is routed through the Eulerian cycle of the network defined by the vertices and lines of the polyhedral structure, wherein the nanostructure comprises at least one edge including a double stranded or single-stranded crossover, wherein the location of the double strand crossover is determined by the spanning tree of the polyhedral structure, wherein the staple sequences are hybridized to the vertices, edges and double strand crossovers of the single stranded nucleic acid including bit-stream data to define the shape of the nanostructure, and wherein one or more of the staple sequences comprises one or more address label sequences.

32. The memory object of claim 30 further comprising one or more encapsulating agents, wherein the encapsulating agent coats or encapsulates the sequence-controlled polymer.

33. The memory object of claim 32, wherein the encapsulating agent includes one or more address label sequences, and wherein the one or more address labels are located at the outer surface of the memory object.

34. The memory object of claim 32, wherein the one or more encapsulating agents are selected from the group consisting of natural polymers and synthetic polymers, or combinations thereof.

35. The memory object of claim 32, wherein one or more encapsulating agents are selected from the group consisting of proteins, polysaccharides, lipids, nucleic acids, or any derivatives thereof.

36. The memory object of claim 31, wherein the staple sequences comprise from 14 to 1,000 nucleotides, inclusive.

37. The memory object of claim 31, wherein the single-stranded nucleic acid sequence comprises approximately 100 to 1,000,000 nucleotides, inclusive.

38. The memory object of claim 31, wherein one or more staple sequences include one or more address label sequences at the 5' end, at the 3' end, or at both the 5' end and at the 3' end.

39. The memory object of claim 30, wherein the one or more address label sequences comprise one or more overhang oligonucleotide sequences.

40. The memory object of claim 30, wherein the one or more address label sequences comprise oligonucleotide sequences complementary to one or more address label sequences attached to a different memory object.

41. The memory object of claim 30, further comprising one or more additional memory objects bound thereto.

42. The method of claim 1, wherein storing the memory object in step (b) further comprises one or more of dehydrating, lyophilizing, or freezing the memory object.

43. The method of claim 42, wherein storing the memory object in step (b) further comprises one or more of rehydrating or thawing the memory object for processing.

44. The method of claim 1, wherein storing the memory objects comprises storage in a matrix selected from the group consisting of cellulose, paper, Microfluidics, bulk 3D solution, on surfaces using electrical forces, on surfaces using magnetic forces, and combinations thereof.

45. The method of claim 1, wherein storing the memory object in step (b) further comprises digitally processing droplets containing nucleic acid memory objects.

46. The method or composition of claim 1 wherein the memory object is composed of DNA, RNA, locked nucleic acid (LNA), peptide nucleic acid (PNA), or an analogue, derivative, or modified nucleotide thereof, or a combination thereof.

47. The method or composition of claim 46 wherein the nucleic acid sequence is single stranded or double stranded.

48. A method of automating the assembly of the memory object of claim 30 comprising using a device with flow, the device comprising (a) means for flowing in the constituent components of the memory object, (b) means for mixing the constituent components, wherein the means for mixing is operatively connected to the means for flowing, (c) means for annealing the constituent components to form an assembled memory object, wherein the means for annealing is operatively connected to the means for mixing, and (d) means for purifying the assembled memory object, wherein the means for purifying is operatively connected to the means for annealing.

* * * * *